United States Patent
Nakamura et al.

(10) Patent No.: US 8,642,626 B2
(45) Date of Patent: Feb. 4, 2014

(54) ETHINYL-PYRAZOLE DERIVATIVE

(75) Inventors: Toshio Nakamura, Toshima-ku (JP); Kazunari Sakagami, Toshima-ku (JP); Kazuhide Konishi, Toshima-ku (JP); Kanako Yamamoto, Toshima-ku (JP); Seiji Masuda, Toshima-ku (JP); Yohei Matsuda, Toshima-ku (JP); Kumiko Okada, Toshima-ku (JP); Tsuyoshi Shibata, Toshima-ku (JP); Hiroshi Ohta, Toshima-ku (JP); Akito Yasuhara, Toshima-ku (JP); Hiroshi Kawamoto, Toshima-ku (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/812,437

(22) PCT Filed: Jul. 29, 2011

(86) PCT No.: PCT/JP2011/067394
§ 371 (c)(1),
(2), (4) Date: Jan. 25, 2013

(87) PCT Pub. No.: WO2012/015024
PCT Pub. Date: Feb. 2, 2012

(65) Prior Publication Data
US 2013/0123500 A1 May 16, 2013

(30) Foreign Application Priority Data
Jul. 29, 2010 (JP) ................................. 2010-170732

(51) Int. Cl.
*A61K 31/4439* (2006.01)
*A61K 31/415* (2006.01)
*C07D 231/12* (2006.01)
*C07D 231/20* (2006.01)
*C07D 231/38* (2006.01)
*C07D 403/06* (2006.01)
*C07D 401/06* (2006.01)

(52) U.S. Cl.
USPC ........... 514/341; 514/406; 514/407; 544/331; 544/405; 544/371; 546/275.4; 548/377.1; 548/366.1; 548/371.4

(58) Field of Classification Search
USPC ............ 514/406, 407, 341; 548/377.1, 376.1, 548/375.1, 366.1, 371.4; 546/275.4, 276.1; 544/331, 405, 371
See application file for complete search history.

(56) References Cited

FOREIGN PATENT DOCUMENTS

| WO | 01/29011 A2 | 4/2001 |
|---|---|---|
| WO | 01/29012 A2 | 4/2001 |
| WO | 02/46166 A1 | 6/2002 |
| WO | 2005/123703 A2 | 12/2005 |
| WO | 2006/099972 A1 | 9/2006 |
| WO | 2009/024491 A1 | 2/2009 |
| WO | 2010/063487 A1 | 6/2010 |

OTHER PUBLICATIONS

"Autism," [retrieved on May 14, 2008]. Retrieved online via Internet, URL: http://www.nlm.nih.gov/medlineplus/autism.html.*
"Anxiety," [retrieved on May 14, 2008]. Retrieved online via Internet, URL: http://www.nlm.nih.gov/medlineplus/anxiety.html.*
Andrzej Pilc, et al., "Mood disorders: Regulation by metabotropic glutmate receptors", Biochemical Pharmacology, 2008, pp. 997-1006, vol. 75.
Guy A. Higgins, et al., "Pharmacological manipulation of mGlu2 receptors influences cognitive performance in the rodent", Neuropharmacology, 2004, pp. 907-917, vol. 46.

* cited by examiner

*Primary Examiner* — Kristin Vajda
(74) *Attorney, Agent, or Firm* — Sughrue Mion, PLLC

(57) ABSTRACT

Provided is a novel compound represented by formula [I] or a pharmaceutically acceptable salt thereof having antagonistic activity against group II metabolism-type glutamic acid (m-Glu) receptors. The compound or pharmaceutically acceptable salt thereof is useful as a prophylactic or therapeutic agent for diseases such as new mood disorders (depressive and bipolar disorders), anxiety disorders (generalized anxiety disorder, panic disorder, obsessive-compulsive disorder, social anxiety disorder, post-traumatic stress disorder, specific phobias, and acute stress disorder), schizophrenia, Alzheimer's disease, cognitive dysfunction, dementia, drug dependence, convulsions, tremors, pain, sleep disorders, and the like.

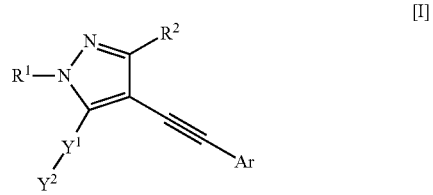

5 Claims, No Drawings

ETHINYL-PYRAZOLE DERIVATIVE

CROSS REFERENCE TO RELATED APPLICATIONS

This application is a National Stage of International Application No. PCT/JP2011/067394 filed Jul. 29, 2011, claiming priority based on Japanese Patent Application No. 2010-170732 filed Jul. 29, 2010, the contents of all of which are incorporated herein by reference in their entirety.

TECHNICAL FIELD

The present invention relates to: a novel compound having an antagonistic effect on group II metabotropic glutamate (mGlu) receptors, or a pharmaceutically acceptable salt thereof; and an agent for preventing or treating diseases such as mood disorder (depressive disorder, bipolar disorder, etc.), anxiety disorder (generalized anxiety disorder, panic disorder, obsessive-compulsive disorder, social anxiety disorder, posttraumatic stress disorder, specific phobic disorder, acute stress disorder, etc.), schizophrenia, Alzheimer's disease, cognitive impairment, dementia, drug dependence, convulsion, tremor, pain, and sleep disorder, which comprises, as an active ingredient, the above-mentioned compound or a pharmaceutically acceptable salt thereof.

BACKGROUND ART

Glutamic acid has been known as a main excitatory neurotransmitter that regulates high-order functions such as memory and learning in the central nervous system of mammals. Glutamate receptors are broadly classified into two types of receptors, namely, ionotropic glutamate (iGlu) receptors, and metabotropic glutamate (mGlu) receptors that are G-protein coupled receptors (GPCR). The iGlu receptors are classified into three types of receptors based on their agonist specificity; namely, N-methyl-D-aspartate (NMDA) receptors, α-amino-3-hydroxy-5-methyl-4-isoxazolepropionic acid (AMPA) receptors, and kainic acid receptors. On the other hand, the mGlu receptors include 8 subtypes (mGlu 1-8), and they are classified into group I (mGlu1 and mGlu5), group II (mGlu2 and mGlu3), and group III (mGlu4, mGlu6, mGlu7, and mGlu8), based on conjugate communication system and pharmacological properties. The group II and group III mGlu receptors are mainly expressed in the nerve ending in the form of an autoreceptor or a hetero receptor. These mGlu receptors suppress adenylate cyclase via a Gi protein and regulate specific $K^+$ or $Ca^{2+}$ channel activity.

In recent years, it has been reported that a glutamic acid concentration is changed in the cerebrospinal fluid and plasma of psychiatric patients suffering from mood disorder, anxiety disorder, schizophrenia and the like. It has been suggested that abnormity in the nerve functions of glutamic acid be associated with psychiatric diseases. An antagonist of group II mGlu receptor, among glutamate receptors, exhibits an antidepressive action and/or an anxiolytic action in various animal models (Non Patent Literature 1). Thus, it has been suggested that the group II mGlu receptor antagonist be likely to act as a novel antidepressive and/or anxiolytic agent. Moreover, it has also been suggested that the group II mGlu receptor antagonist exhibit the effect of a cognitive function enhancing agent (for dementia and Alzheimer's disease) (Non Patent Literature 2).

Recently, Patent Literatures 1 to 3 have reported a compound having an antagonistic effect on the group II mGlu receptor and having an ethynyl structure. However, these patent literatures neither disclose nor suggest a compound having an ethynyl-pyrazole skeleton.

CITATION LIST

Patent Literature

Patent Literature 1: WO2001/029011
Patent Literature 2: WO2001/029012
Patent Literature 3: WO2006/099972

Non Patent Literature

Non Patent Literature 1: Biochemical Pharmacology, 2008, 75, 997-1006
Non Patent Literature 2: Neuropharmacology, 2004, 46, 907-917

SUMMARY OF INVENTION

Technical Problem

It is an object of the present invention to discover a novel compound that is antagonistic to group II mGlu receptors, and to provide a useful agent for preventing or treating diseases such as mood disorder (depressive disorder, bipolar disorder, etc.), anxiety disorder (generalized anxiety disorder, panic disorder, obsessive-compulsive disorder, social anxiety disorder, posttraumatic stress disorder, specific phobic disorder, acute stress disorder, etc.), schizophrenia, Alzheimer's disease, cognitive impairment, dementia, drug dependence, convulsion, tremor, pain, and sleep disorder.

Solution to Problem

The present inventors have found that the aforementioned problem can be solved by a compound represented by the following formula (I) or a pharmaceutically acceptable salt thereof, thereby completing the present invention.

Specifically, the present invention relates to the following (1) to (6): (1) a compound represented by the formula [I], or a pharmaceutically acceptable salt thereof:

[Formula 1]

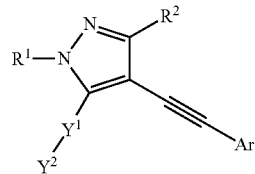

wherein
$R^1$ represents a hydrogen atom or a $C_{1-6}$ alkyl group (wherein the $C_{1-6}$ alkyl group may be substituted with 1 to 3 halogen atoms),
$R^2$ represents a hydrogen atom or a $C_{1-6}$ alkyl group (wherein the $C_{1-6}$ alkyl group may be substituted with 1 to 3 halogen atoms),
Ar represents a phenyl group or a heteroaryl group (wherein the phenyl group or the heteroaryl group may be substituted with 1 to 3 substituents selected from the group consisting of —$SO_2NR^aR^b$, —$SO_2R^c$, —$NR^dSO_2R^e$, a $C_{1-6}$ alkyl group, an amino group, and a halogen atom), $R^a$ and $R^b$, which may be the same or different, each represent a hydrogen atom or a $C_{1-6}$ alkyl group (wherein the $C_{1-6}$ alkyl group may be substituted with one or two substituents selected from the group consisting of an amino group, a $C_{1-6}$ alkylamino group, a di-$C_{1-6}$ alkylamino group, and a hydroxyl group) or $R^a$ and $R^b$ may form a saturated or unsaturated 5- or 6-membered ring, which is formed together with a nitrogen atom to which they bind, and which may further contain one or more nitrogen atoms, oxygen atoms or sulfur atoms, $R^c$ represents a hydroxyl group, a $C_{1-6}$ alkyl group, or a $C_{1-6}$ alkoxy group, $R^d$ represents a hydrogen atom or a $C_{1-6}$ alkyl group, $R^e$ represents a $C_{1-6}$ alkyl group or an amino group, $Y^1$ represents —$(CH_2)_{n1}$—, —$(CH_2)_{n2}$—$NR^f$—$(CH_2)_{n3}$—, —$(CH_2)_{n4}$—O—$(CH_2)_{n5}$—, —$(CH_2)_{n6}$—NHC(=O)—$(CH_2)_{n7}$—, —$(CH_2)_{n8}$—C(=O)NH—$(CH_2)_{n9}$—, ethynylene, piperazin-1,4-yl, phenylene, or heteroarylene, $R^f$ represents a hydrogen atom or a $C_{1-6}$ alkyl group, n1 to n5 each represent an integer from 0 to 6, provided that the sum of n2 and n3 is 6 or less, and the sum of n4 and n5 is 6 or less, n6 to n9 represent an integer from 0 to 5, provided that the sum of n6 and n7 is 5 or less, and the sum of n8 and n9 is 5 or less, $Y^2$ represents an aryl group, a heteroaryl group, a partially saturated condensed polycyclic heteroaryl group {wherein the aryl group, heteroaryl group, or partially saturated condensed polycyclic heteroaryl group may be substituted with 1 to 3 substituents selected from the group consisting of $C_{1-6}$ alkyl group, $C_{3-6}$ cycloalkyl group, a $C_{1-6}$ alkoxy group (wherein the $C_{1-6}$ alkyl group, $C_{3-6}$ cycloalkyl group or $C_{1-6}$ alkoxy group may be substituted with 1 to 3 halogen atoms), a cyano group, and a halogen atom} or a $C_{3-6}$ cycloalkyl group;

(2) the compound or a pharmaceutically acceptable salt thereof according to (1) above, which is represented by the formula [I]:
wherein
Ar represents a phenyl group or a 6-membered heteroaryl group (wherein the phenyl group or the 6-membered heteroaryl group may be substituted with 1 to 3 substituents selected from the group consisting of —$SO_2NR^aR^b$, —$SO_2R^c$, —$NR^dSO_2R^e$, a $C_{1-6}$ alkyl group, an amino group, and a halogen atom, and $R_a$, $R_b$, $R_c$, $R_d$ and $R_e$ are as defined in (1));

(3) the compound or a pharmaceutically acceptable salt thereof according to (1) or (2) above: wherein $Y^1$ represents —$(CH_2)_{n1}$—, —$(CH_2)_{n2}$—$NR^f$—$(CH_2)_{n3}$—, —$(CH_2)_{n4}$—O—$(CH_2)_{n5}$—, —$(CH_2)_{n6}$—NHC(=O)—$(CH_2)_{n7}$—, —$(CH_2)_{n8}$—C(=O)NH—$(CH_2)_{n9}$—, ethynylene, piperazin-1,4-yl, phenylene, pyridylene, or 5-membered heteroarylene (wherein $R^f$ and n1 to n9 are as defined in (1)), $Y^2$ represents a phenyl group, a naphthyl group, a pyridyl group, a quinolinyl group, a partially saturated condensed polycyclic heteroaryl group {wherein the phenyl group, naphthyl group, pyridyl group, quinolinyl group, or partially saturated condensed polycyclic heteroaryl group may be substituted with 1 to 3 substituents selected from the group consisting of a $C_{1-6}$ alkyl group, a $C_{3-6}$ cycloalkyl group, a $C_{1-6}$ alkoxy group (wherein the $C_{1-6}$ alkyl group, $C_{3-6}$ cycloalkyl group, or $C_{1-6}$ alkoxy group may be substituted with 1 to 3 halogen atoms), a cyano group, and a halogen atom} or a $C_{3-6}$ cycloalkyl group;

(4) a medicament comprising, as an active ingredient, the compound or a pharmaceutically acceptable salt thereof according to any one of (1) to (3) above;

(5) the medicament according to (4) above, which is a group II metabotropic glutamate receptor antagonist; and (6) an agent for preventing or treating mood disorder, anxiety disorder, schizophrenia, Alzheimer's disease, cognitive impairment, dementia, drug dependence, convulsion, tremor, pain, or sleep disorder, which comprises, as an active ingredient, the compound or a pharmaceutically acceptable salt thereof according to any one of (1) to (3) above.

Advantageous Effects of Invention

The present inventors have found that the compound of the present invention and a pharmaceutically acceptable salt thereof have a strong antagonistic effect on group II mGlu receptors.

DESCRIPTION OF EMBODIMENTS

Hereinafter, the present invention will be described in more detail.

The terms used in the present specification will be described below.

The "halogen atom" means a fluorine atom, a chlorine atom, a bromine atom, or an iodine atom.

The "$C_{1-6}$ alkyl group" means a linear or branched alkyl group containing 1 to 6 carbon atoms. Examples of such a $C_{1-6}$ alkyl group include a methyl group, an ethyl group, a propyl group, a butyl group, a pentyl group, a hexyl group, an isopropyl group, an isobutyl group, a tert-butyl group, a sec-butyl group, an isopentyl group, a neopentyl group, a tert-pentyl group, and a 1,2-dimethylpropyl group.

The "$C_{1-6}$ alkoxy group" means a linear or branched alkoxy group containing 1 to 6 carbon atoms. Examples of such a $C_{1-6}$ alkoxy group include a methoxy group, an ethoxy group, a propoxy group, a butoxy group, a pentyloxy group, a hexyloxy group, an isopropoxy group, an isobutoxy group, a tert-butoxy group, a sec-butoxy group, an isopentyloxy group, a neopentyloxy group, a tert-pentyloxy group, and a 1,2-dimethylpropoxy group.

The "$C_{1-6}$ alkylamino group" means an amino group substituted with one $C_{1-6}$ alkyl group. Examples of such a mono-$C_{1-6}$ alkylamino group include a methylamino group, an ethylamino group, a propylamino group, a butylamino group, a pentylamino group, a hexylamino group, an isopropylamino group, an isobutylamino group, a tert-butylamino group, a sec-butylamino group, an isopentylamino group, a neopentylamino group, a tert-pentylamino group, and a 1,2-dimethylpropylamino group.

The "di-$C_{1-6}$ alkylamino group" means an amino group substituted with two independent $C_{1-6}$ alkyl groups. Examples of such a di-$C_{1-6}$ alkylamino group include a dimethylamino group, a diethylamino group, a dipropylamino group, a dibutylamino group, a dipentylamino group, a dihexylamino group, a diisopropylamino group, a diisobutylamino group, a di-tert-butylamino group, a di-sec-butylamino group, a di-isopentylamino group, a di-neopentylamino group, a di-tert-pentylamino group, a di-1,2-dimethylpropylamino group, an ethylmethylamino group, an isopropylmethylamino group, and an isobutylisopropylamino group.

The "$C_{3-6}$ cycloalkyl group" means a cycloalkyl group containing 3 to 6 carbon atoms. Examples of such a $C_{3-6}$ cycloalkyl group include a cyclopropyl group, a cyclobutyl group, a cyclopentyl group, and a cyclohexyl group.

The "aryl group" means a mono- to tetracyclic aromatic carbocyclic group containing 6 to 18 carbon atoms. Examples of such an aryl group include a phenyl group, a naphthyl group, an anthryl group, a phenanthryl group, a tetracenyl group, and a pyrenyl group.

The "heteroaryl group" means a monocyclic or condensed-ring aromatic heterocyclic group. Examples of such a heteroaryl group include a pyridyl group, a pyridazinyl group, a pyrimidinyl group, a pyrazinyl group, a thienyl group, a pyrrolyl group, a thiazolyl group, an isothiazolyl group, pyrazolyl group, an imidazolyl group, a furyl group, an oxazolyl group, an isoxazolyl group, an oxadiazolyl group, a 1,3,4-thiadiazolyl group, a 1,2,3-triazolyl group, a 1,2,4-triazolyl group, a tetrazolyl group, a quinolyl group, an isoquinolyl group, a naphthyridinyl group, a quinazolinyl group, a benzofuranyl group, a benzothienyl group, an indolyl group, a benzoxazolyl group, a benzisoxazolyl group, a 1H-indazolyl group, a 2H-indazolyl group, a benzimidazolyl group, a benzoxadiazolyl group, a benzothiadiazolyl group, an indolizinyl group, a benzofurazanyl group, a thienopyridyl group, a pyrazolopyridyl group, an imidazopyridyl group, an imidazopyrazinyl group, a pyrazolopyrimidinyl group, a triazolopyrimidinyl group, a thienothienyl group, and an imidazothiazolyl group.

The "6-membered heteroaryl group" means a 6-membered ring aromatic heterocyclic group. Examples of such a 6-membered heteroaryl group include a pyridyl group, a pyridazinyl group, a pyrimidinyl group, and a pyrazinyl group.

The "5-membered heteroaryl group" means a 5-membered ring aromatic heterocyclic group. Examples of such a 5-membered heteroaryl group include a thienyl group, a pyrrolyl group, a thiazolyl group, an isothiazolyl group, a pyrazolyl group, an imidazolyl group, a furyl group, an oxazolyl group, an isoxazolyl group, an oxadiazolyl group, a 1,3,4-thiadiazolyl group, a 1,2,3-triazolyl group, a 1,2,4-triazolyl group, and a tetrazolyl group.

The "partially saturated condensed polycyclic heteroaryl group" means a condensed polycyclic aromatic heterocyclic group having a single ring in which a portion of a bond constituting the ring is saturated. This group may be substituted with 1 to 3 oxo groups. Examples of such a partially saturated condensed polycyclic heteroaryl group include an isoindolin-2-yl group, a 2,3-dihydro-1H-benzo[f]isoindol-2-yl group, an isoindolin-1,3-dion-2-yl group, a 1H-benzo[f]isoindol-1,3(2H)-dion-2-yl group, a 1,2,3,4-tetrahydroisoquinolin-2-yl group, and a 2,3,4,5-tetrahydro-1H-benzo[d]azepin-3-yl group.

Examples of the "saturated or unsaturated 5- or 6-membered ring, which is formed together with a nitrogen atom to which they bind, and which may further contain one or more nitrogen atoms, oxygen atoms or sulfur atoms" include a pyrrolidino group, a piperidino group, a piperazino group, a morpholino group, a thiomorpholino group, and a 1,2,3,6-tetrahydropyridin-1-yl group.

A preferred embodiment of the compound of the present invention is as follows.

As a preferred combination of $Y^1$ and $Y^2$, $Y^1$ represents —$(CH_2)_2$—, —$CH_2$—NH—, —NH—$CH_2$—, —$CH_2$—O—, —$CH_2$—$CH_2$—O—, —O—$CH_2$—, phenylene, or 5-membered heteroarylene, $Y^2$ represents a phenyl group or a pyridyl group {wherein the phenyl group or the pyridyl group may be substituted with 1 to 3 substituents selected from the group consisting of a $C_{1-6}$ alkyl group, a $C_{3-6}$ cycloalkyl group, a $C_{1-6}$ alkoxy group (wherein the $C_{1-6}$ alkyl group, $C_{3-6}$ cycloalkyl group, or $C_{1-6}$ alkoxy group may be substituted with 1 to 3 halogen atoms), a cyano group, and a halogen atom}, or $Y^1$ represents a bond, $Y^2$ represents a phenyl group, a pyridyl group, an isoindolin-2-yl group, or a 2,3-dihydro-1H-benzo[f]isoindol-2-yl group {wherein the phenyl group, pyridyl group, isoindolin-2-yl group, or 2,3-dihydro-1H-benzo[f]isoindol-2-yl group may be substituted with 1 to 3 substituents selected from the group consisting of a $C_{1-6}$ alkyl group, a $C_{3-6}$ cycloalkyl group, a $C_{1-6}$ alkoxy group (wherein the $C_{1-6}$ alkyl group, $C_{3-6}$ cycloalkyl group, or $C_{1-6}$ alkoxy group may be substituted with 1 to 3 halogen atoms), a cyano group, and a halogen atom}.

The compound of the present invention may include stereoisomers such as a tautomer and a geometric isomer, and optical isomers. The present invention includes these isomers. In addition, the present invention also includes various types of hydrates, solvates and crystalline polymorphic forms of the compound of the present invention and the salt thereof. Moreover, compound [I] of the present invention may be labeled with an isotope (for example, with D, $^3H$, $^{13}C$, $^{14}C$, $^{15}N$, $^{31}P$, $^{32}P$, $^{35}S$, $^{18}F$, $^{125}I$, etc.).

The term "pharmaceutically acceptable salt" is used in the present invention to mean a salt that is acceptable as an agent. Examples of such a pharmaceutically acceptable salt include: salts formed with acids such as acetic acid, propionic acid, butyric acid, formic acid, trifluoroacetic acid, maleic acid, tartaric acid, citric acid, stearic acid, succinic acid, ethyl succinate, malonic acid, lactobionic acid, gluconic acid, glucopeptonic acid, benzoic acid, methanesulfonic acid, ethanesulfonic acid, 2-hydroxyethanesulfonic acid, benzenesulfonic acid, paratoluenesulfonic acid (tosic acid), lauryl sulfate, malic acid, aspartic acid, glutamic acid, adipic acid, cysteine, N-acetyl cysteine, hydrochloric acid, hydrobromic acid, phosphoric acid, sulfuric acid, hydriodic acid, nicotinic acid, oxalic acid, picric acid, thiocyanic acid, undecanoic acid, an acrylic acid polymer, and a carboxy vinyl polymer; salts formed with inorganic bases, such as lithium salts, sodium salts, potassium salts, and calcium salts; salts formed with organic amines such as morpholine and piperidine; and salts formed with amino acids.

Compound [I] of the present invention or a pharmaceutically acceptable salt thereof can be processed into a pharmaceutical preparation, directly or together with pharmaceutically acceptable carriers, according to a known method. Examples of such a carrier include various types of organic or inorganic carrier substances that are commonly used as pharmaceutical materials. Specific examples of a carrier used for solid preparations include excipients (e.g. lactose, saccharose, D-mannitol, starch, corn starch, crystalline cellulose, and light anhydrous silicic acid), lubricants (e.g. magnesium stearate, calcium stearate, talc, and colloidal silica), binders (e.g. crystalline cellulose, saccharose, D-mannitol, dextrin, hydroxypropyl cellulose, hydroxypropylmethyl cellulose, polyvinyl pyrrolidone, starch, sucrose, gelatin, methyl cellulose, and carboxymethyl cellulose sodium), and disintegrators (e.g. starch, carboxymethyl cellulose, carboxymethyl cellulose calcium, croscarmellose sodium, carboxymethyl starch sodium, and low-substituted hydroxypropyl cellulose). Specific examples of a carrier used for liquid preparations include solvents (e.g. water for injection, alcohol, propylene glycol, macrogol, sesame oil, and corn oil), solubilizers (e.g. polyethylene glycol, propylene glycol, D-mannitol, benzyl benzoate, ethanol, trisaminomethane, cholesterol, triethanolamine, sodium carbonate, and sodium citrate), suspending agents (e.g. surfactants such as stearyl triethanolamine, sodium lauryl sulfate, laurylaminopropionic acid, lecithin, benzalkonium chloride, benzethonium chloride and glyceryl monostearate, or hydrophilic polymers such as polyvinyl alcohol, polyvinyl pyrrolidone, carboxymethyl cellulose sodium, methyl cellulose, hydroxymethyl cellulose and hydroxypropyl cellulose), isotonizing agents (e.g. glucose, D-sorbitol, sodium chloride, glycerin, and D-mannitol), buffering agents (e.g. phosphate, acetate, carbonate, and citrate), and soothing agents (e.g. benzyl alcohol). Moreover, when a pharmaceutical preparation is produced, the following agents may be used, as necessary: antiseptics (e.g. paraoxybenzoic acid esters, chlorobutanol, benzyl alcohol, phenethyl alcohol, dehydroacetic acid, and sorbic acid), antioxidants (e.g. sulfite and ascorbic acid), coloring agents, sweeteners, adsorbents, wetting agents, etc.

Compound [I] of the present invention or a pharmaceutically acceptable salt thereof can be administered orally or parenterally (e.g. intravenous administration, local administration, and rectal administration). Examples of the dosage form include a tablet (including a sugar-coated tablet and a film-coated tablet), a powder, a granule, a dust formulation, a troche, a capsule (including a soft capsule), a liquid agent, an injection (e.g. a subcutaneous injection, an intravenous injection, an intramuscular injection, and an intraperitoneal injection), an external agent (e.g. a transnasal preparation, a transdermal preparation, an ointment, and a cream), a suppository (e.g. a rectal suppository and a vaginal suppository), a sustained-release preparation (e.g. a sustained-release microcapsule), a pellet, and an eye drop. All of these preparations can be produced by a commonly used formulation technique (e.g. the method described in the Japanese Pharmacopoeia 15$^{th}$ Edition).

The applied dosage of compound [I] of the present invention or a pharmaceutically acceptable salt thereof can be selected, as appropriate, depending on administration target, administration route, disease, and the age, body weight and symptoms of a patient. For example, when an adult patient is treated by administration of the present compound or a salt thereof, the applied dose is 1 to 2000 mg per day, and this dose is administered once or divided over several administrations per day.

When the group II mGlu receptor antagonist is used as an active ingredient for medicaments, it can be used not only for humans, but also for other animals other than humans (a cat, a dog, a bovine, a chicken, fish, etc.).

The compound of the present invention and a pharmaceutically acceptable salt thereof can be synthesized, for example, by methods as described below. However, the method for producing the compound of the present invention is not limited thereto.

Examples of the "inactive solvent" include: aromatic solvents such as benzene, toluene, xylene, and pyridine; hydrocarbon solvents such as hexane, pentane, and cyclohexane; halogenated hydrocarbon solvents such as dichloromethane, chloroform, 1,2-dichloroethane, and carbon tetrachloride; ether solvents such as tetrahydrofuran, diethyl ether, 1,2-dimethoxyethane, and 1,4-dioxane; ester solvents such as ethyl acetate and ethyl formate; alcohol solvents such as methanol, ethanol, isopropyl alcohol, tert-butyl alcohol, and ethylene glycol; ketone solvents such as acetone and methyl ethyl ketone; amide solvents such as N,N-dimethylformamide, N-methylpyrrolidone, and N,N-dimethylacetamide; sulfoxide solvents such as dimethyl sulfoxide; nitrile solvents such as acetonitrile and propionitrile; water; and homogeneous and heterogeneous mixed solvents thereof. These inactive solvents are selected, as appropriate, depending on various types of reaction conditions that are known to a person skilled in the art.

Examples of the "base" include: hydrides of alkaline metals or alkaline-earth metals, such as lithium hydride, sodium hydride, potassium hydride, and calcium hydride; amides of alkaline metals or alkaline-earth metals, such as lithium amide, sodium amide, lithium diisopropyl amide, lithium dicyclohexyl amide, lithium hexamethyl disilazide, sodium hexamethyl disilazide, and potassium hexamethyl disilazide; lower alkoxides of alkaline metals or alkaline-earth metals, such as sodium methoxide, sodium ethoxide, and potassium tert-butoxide; alkyl lithium such as butyl lithium, sec-butyl lithium, tert-butyl lithium, and methyl lithium; hydroxides of alkaline metals or alkaline-earth metals, such as sodium hydroxide, potassium hydroxide, lithium hydroxide, and barium hydroxide; carbonates of alkaline metals or alkaline-earth metals, such as sodium carbonate, potassium carbonate, and cesium carbonate; hydrogencarbonates of alkaline metals or alkaline-earth metals, such as sodium hydrogencarbonate and potassium hydrogencarbonate; amines such as triethylamine, N-methylmorpholine, N,N-diisopropylethylamine, 1,8-diazadicyclo[5.4.0]undec-7-ene (DBU), 1,5-diazadicyclo[4.3.0]non-5-ene (DBN), and N,N-dimethylaniline; quaternary ammonium salts such as tetra-n-butylammonium fluoride and benzyltrimethylammonium hydroxide; and basic heterocyclic compounds such as pyridine, imidazole, and 2,6-lutidine. These bases are selected, as appropriate, depending on various types of reaction conditions that are known to a person skilled in the art.

Examples of the "acid" include: inorganic acid such as hydrochloric acid, hydrobromic acid, sulfuric acid, nitric acid, and phosphoric acid; and organic acids such as p-toluenesulfonic acid, methanesulfonic acid, trifluoroacetic acid, formic acid, and acetic acid. These acids are selected, as appropriate, depending on various types of reaction conditions that are known to a person skilled in the art.

[Production Method 1]

Compound [I] of the present invention can be produced by the following method.

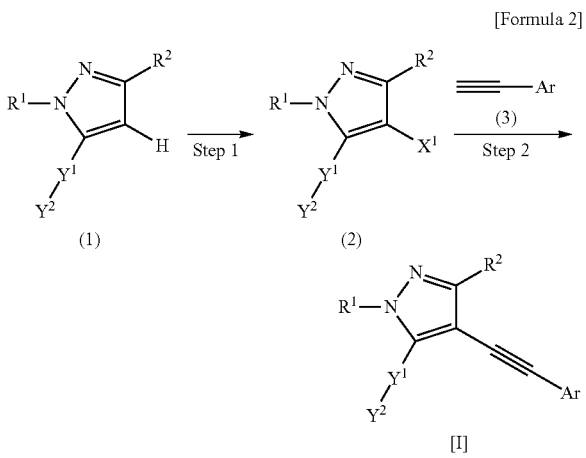

In the above formula, $X^1$ represents a chlorine atom, a bromine atom, or an iodine atom, and Ar, $R^1$, $R^2$, $Y^1$ and $Y^2$ are defined as above.

Step 1: Compound (2) can be produced by allowing compound (1) to react with a halogenating agent such as N-chlorosuccinimide, N-bromosuccinimide or N-iodosuccinimide in an inactive solvent and in the presence or absence of an acid. Alternatively, compound (2) can be produced by allowing compound (1) to react with a halogenating agent such as iodine chloride, iodine or bromine in an inactive solvent and in the presence or absence of a base. Herein, as compound (1), a commercially available compound, a known compound, or a compound synthesized from such a commercially available compound or known compound according to various organic synthesis methods known to a person skilled in the art can be used.

Step 2: Compound [I] of the present invention can be produced by a coupling reaction between compound (2) and compound (3) in an inactive solvent, in the presence or absence of a base, and in the presence of a transition metal catalyst, using a ligand as necessary. As compound (3), a commercially available compound, a known compound, or a compound synthesized from such a commercially available compound or known compound according to various organic synthesis methods known to a person skilled in the art can be used {see Comprehensive Organic Transformations, Second Edition, 1999, John Wiley & Sons, INC.}. Examples of the transition metal catalyst used herein include dichlorobistriphenylphosphine palladium(II), dichlorobisacetonitrile palladium(II), tetrakistriphenylphosphine palladium(0), palladium(II) chloride, copper powder, copper(I) chloride, copper (I) bromide, copper(I) iodide, and copper(I) acetate. Examples of a ligand of palladium catalyst include triphenylphosphine, tributylphosphine, 2,2-bis(diphenylphosphino)-1,1-binaphthyl (BINAP), 2-(di-tert-butylphosphino) biphenyl, 1,1'-bis(diphenylphosphino)ferrocene.

Compound (1') can be produced by the following method, for example.

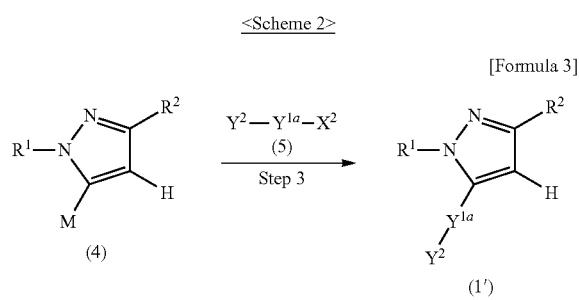

In the above formula, $R^1$, $R^2$ and $Y^2$ are defined as above. $Y^{1a}$ represents phenylene, heteroarylene, or a bond. When $Y^{1a}$ is a bond, $Y^2$ represents an aryl group or a heteroaryl group {wherein the aryl group or the heteroaryl group may be substituted with 1 to 3 substituents selected from the group consisting of a $C_{1-6}$ alkyl group, a $C_{3-6}$ cycloalkyl group, a $C_{1-6}$ alkoxy group (wherein the $C_{1-6}$ alkyl group, $C_{3-6}$ cycloalkyl group or $C_{1-6}$ alkoxy group may be substituted with 1 to 3 halogen atoms), a cyano group, and a halogen atom}. $X^2$ represents a leaving group such as a chlorine atom, a bromine atom, a halogen atom of an iodine atom, or an organic sulfonyloxy group such as a methanesulfonyloxy group, a benzenesulfonyloxy group, a p-toluenesulfonyloxy group, a trifluoromethanesulfonyloxy group. M represents a metal atom used in a coupling reaction. Examples of compound (4) include a magnesium reactant, a zinc reactant, a boron reactant to which boric acid or borate ester binds, and a tin reactant.

Step 3: Compound (1') can be produced by a coupling reaction between compound (4) and compound (5) in an inactive solvent and in the presence or absence of a base, using a palladium catalyst and as necessary, a ligand. As a coupling reaction used herein, coupling reaction conditions known to a person skilled in the art are applied. For instance, the present coupling reaction can be carried out according to the method described in {Comprehensive Organic Transformations, Second Edition, 1999, John Wiley & Sons, INC.}, etc., a method equivalent thereto, or a combination of such a method with an ordinary method. As compound (4) and compound (5), commercially available compounds, known compounds, or compounds synthesized from such commercially available compounds or known compounds according to various organic synthesis methods known to a person skilled in the art can be used. Examples of the palladium catalyst used herein include palladium(II) acetate, palladium(II) chloride, bis(triphenylphosphine)palladium(II) acetate, bis(triphenylphosphine)palladium(II) chloride, tris(dibenzylideneacetone)dipalladium(0), bis(dibenzylideneacetone)palladium (0), tetrakistriphenylphosphine palladium(0), [1,1'-bis(diphenylphosphino)ferrocene]palladium(II) chloride, allylpalladium(II) chloride, and bis(acetonitrile)palladium (II) chloride. Examples of the ligand include triphenylphosphine, 2,2-bis(diphenylphosphino)-1,1-binaphthyl (BINAP), 2-(di-tert-butylphosphino)biphenyl, and 9,9-dimethyl-4,5-bis(diphenylphosphino)xanthene (Xantphos).

Compound (1), which is represented by the formula (1-1), can be produced by the following method, for example.

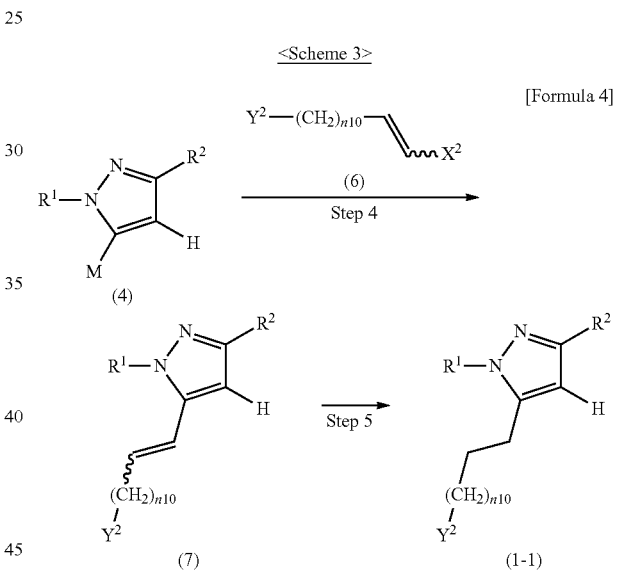

In the above formula, M, $R^1$, $R^2$, $X^2$ and $Y^2$ are defined as above. n10 represents an integer from 0 to 4.

Step 4: Compound (7) can be produced from compound (4) and compound (6) according to the same method as that in step 3 of <Scheme 2>. As compound (4) and compound (6), commercially available compounds, known compounds, or compounds synthesized from such commercially available compounds or known compounds according to various organic synthesis methods known to a person skilled in the art can be used.

Step 5: Compound (1-1) can be produced by subjecting compound (7) to a catalytic reduction reaction in an inactive solvent, in the presence of a transition metal catalyst, under a hydrogen atmosphere, and under an ordinary pressure or increased pressure {see Comprehensive Organic Transformations, Second Edition, 1999, John Wiley & Sons, INC.}. Examples of the transition metal catalyst used herein include palladium carbon, palladium hydroxide, palladium black, palladium-fibroin, platinum (IV) oxide, and Raney nickel.

Compound (7) can be produced by the following method, for example.

<Scheme 4>

[Formula 5]

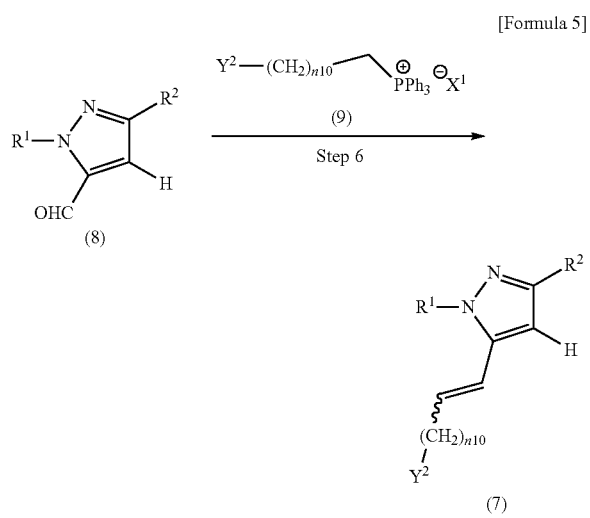

In the above formula, n10, $R^1$, $R^2$, $X^1$ and $Y^2$ are defined as above.

Step 6: Compound (7) can be produced by subjecting compound (8) and compound (9) to a Wittig reaction in an inactive solvent and in the presence of a base. As compound (8) and compound (9), commercially available compounds, known compounds, or compounds synthesized from such commercially available compounds or known compounds according to various organic synthesis methods known to a person skilled in the art can be used.

Compound (1), which is represented by the formula (1-1), can be produced by the following method, for example.

<Scheme 5>

[Formula 6]

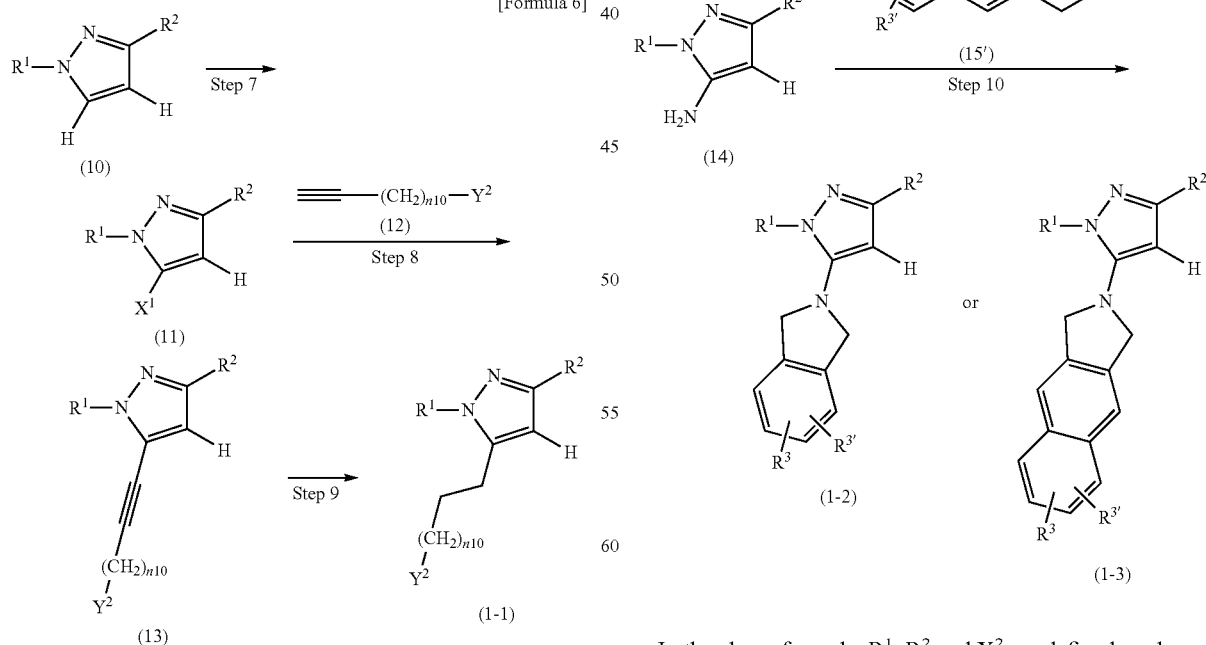

In the above formula, n10, $R^1$, $R^2$, $X^1$ and $Y^2$ are defined as above.

Step 7: Compound (11) can be produced by allowing compound (10) to react with a halogenating agent such as N-chlorosuccinimide, N-bromosuccinimide, N-iodosuccinimide, iodine or bromine in an inactive solvent and in the presence of a base. Herein, as compound (10), a commercially available compound, a known compound, or a compound synthesized from such a commercially available compound or known compound according to various organic synthesis methods known to a person skilled in the art can be used.

Step 8: Compound (13) can be produced from compound (11) and compound (12) according to the same method as that in step 2 of <Scheme 1>. Herein, as compound (12), commercially available compounds, known compounds, or compounds synthesized from such commercially available compounds or known compounds according to various organic synthesis methods known to a person skilled in the art can be used.

Step 9: Compound (1-1) can be produced from compound (13) according to the same method as that in step 5 of <Scheme 3>.

Compound (1), which is represented by the formula (1-2) and the formula (1-3), can be produced by the following method, for example.

<Scheme 6>

[Formula 7]

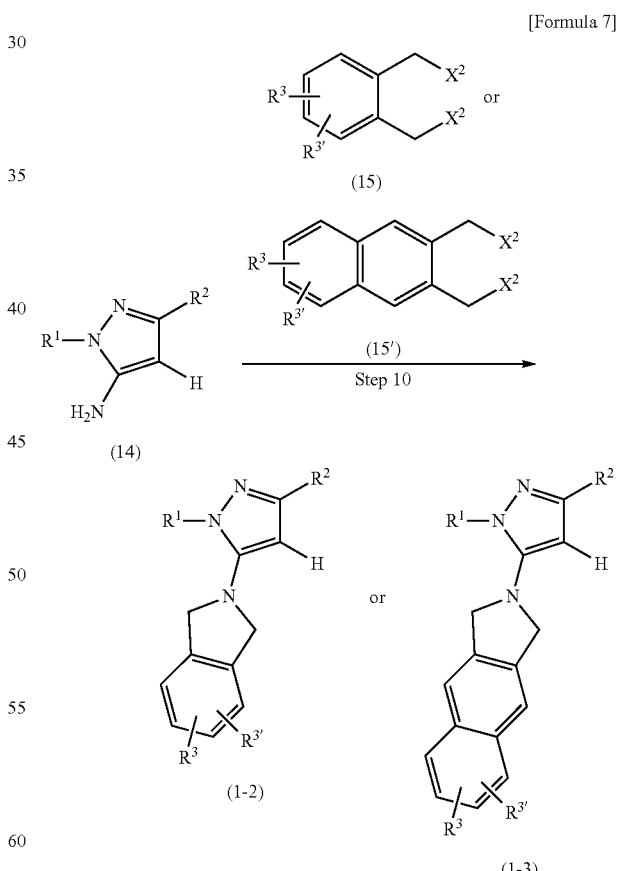

In the above formula, $R^1$, $R^2$ and $X^2$ are defined as above. $R^3$ and $R^{3'}$, which may be the same or different, each represent a hydrogen atom, a $C_{1-6}$ alkyl group, a $C_{3-6}$ cycloalkyl group, a $C_{1-6}$ alkoxy group (wherein the $C_{1-6}$ alkyl group, $C_{3-6}$ cycloalkyl group or $C_{1-6}$ alkoxy group may be substituted with 1 to 3 halogen atoms), a cyano group, or a halogen atom.

Step 10: Compound (1-2) or (1-3) can be produced by subjecting compound (14) to an alkylation reaction using compound (15) or compound (15') in an inactive solvent and in the presence or absence of a base {see Comprehensive Organic Transformations, Second Edition, 1999, John Wiley & Sons, INC.}. Herein, as compound (14), compound (15), and compound (15'), commercially available compounds, known compounds, or compounds synthesized from such commercially available compounds or known compounds according to various organic synthesis methods known to a person skilled in the art can be used.

Compound (1), which is represented by the formula (1-4), can be produced by the following method.

Compound (1), which is represented by the formula (1-5), can be produced by the following method, for example.

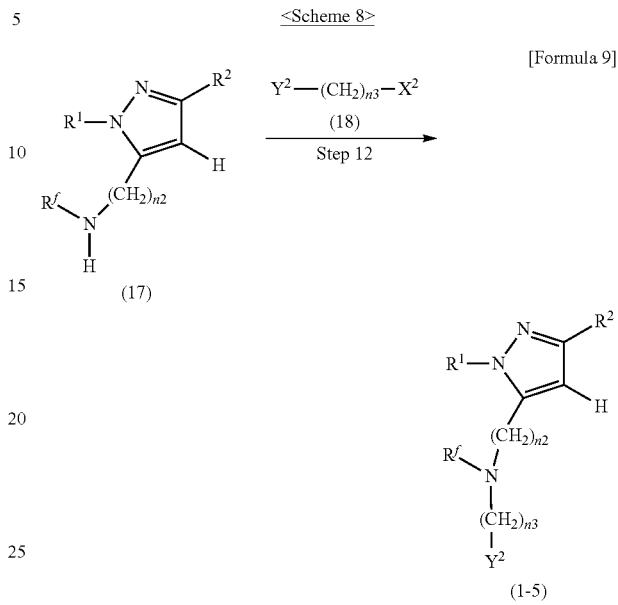

In the above formula, n2, n3, $R^1$, $R^2$, $R^f$, $X^2$ and $Y^2$ are defined as above.

Step 12: Compound (1-5) can be produced from compound (17) and compound (18) according to the same method as that in step 10 of <Scheme 6>. Herein, as compound (17) and compound (18), commercially available compounds, known compounds, or compounds synthesized from such commercially available compounds or known compounds according to various organic synthesis methods known to a person skilled in the art can be used.

Compounds (1), which are represented by the formula (1-6) and the formula (1-7), can be produced by the following method, for example.

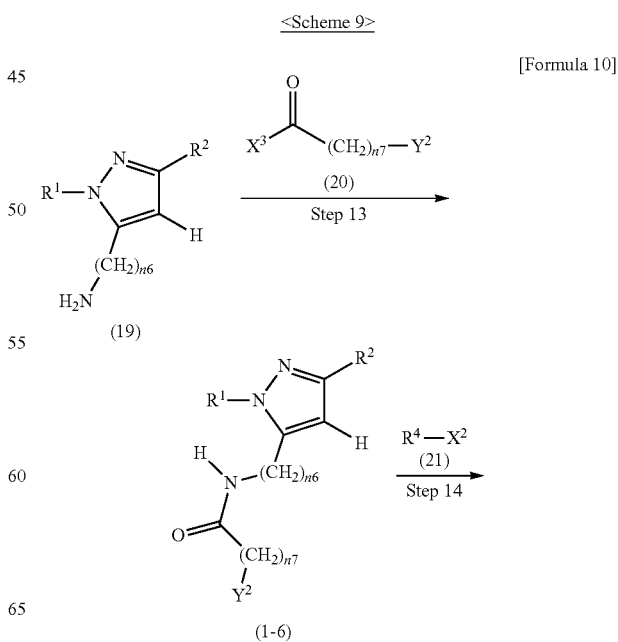

In the above formula, $R^1$, $R^2$, $R^3$ and $R^{3'}$ are defined as above.

Step 11: Compound (1-4) can be produced by subjecting compound (14) and compound (16) to a dehydration condensation reaction in an inactive solvent and in the presence or absence of a base. Herein, as compound (14) and compound (16), commercially available compounds, known compounds, or compounds synthesized from such commercially available compounds or known compounds according to various organic synthesis methods known to a person skilled in the art can be used.

-continued

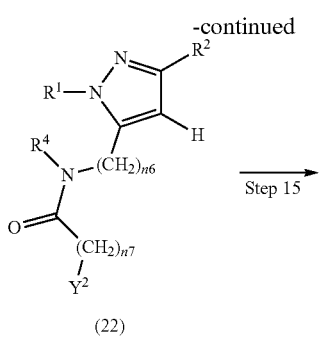
(22)

Step 15 →

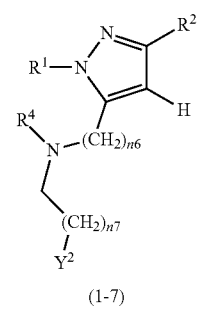
(1-7)

In the above formula, n6, n7, $R^1$, $R^2$, $X^2$ and $Y^2$ are defined as above. $R^4$ represents a $C_{1-6}$ alkyl group, and $X^3$ represents a chlorine atom, a bromine atom, an iodine atom or a hydroxyl group.

Step 13: Compound (1-6) can be produced by subjecting compound (19) and compound (20), in which $X^3$ is a halogen atom, to an amidation reaction in an inactive solvent and in the presence or absence of a base. Alternatively, compound (1-6) can also be produced by subjecting compound (19) and compound (20), in which $X^3$ is a hydroxyl group, to various amidation reactions known to a person skilled in the art. As compound (19) and compound (19), commercially available compounds, known compounds, or compounds synthesized from such commercially available compounds or known compounds according to various organic synthesis methods known to a person skilled in the art can be used. Examples of the amidation reaction of compound (20), in which $X^3$ is a hydroxyl group, include: a condensation reaction carried out in an inactive solvent and in the presence or absence of a base, using a condenser such as O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), N,N'-dicyclohexylcarbodiimide (DCC), 1-ethyl-3-(3-dimethylaminopropyl)carbodiimide hydrochloride (EDC.HCl), diphenylphosphoryl azide (DPPA) or carbonyldiimidazole (CDI); and a condensation reaction mediated by a mixed acid anhydride that is carried out in an inactive solvent and in the presence or absence of a base, using ethyl chloroformate, isobutyl chloroformate, trimethylacetyl chloride or the like. Also, herein, when an amidation reaction is carried out using a condenser, an additive such as 1-hydroxybenzotriazole (HOBt) or hydroxysuccinimide (HOSu) can be used, as necessary.

Step 14: Compound (22) can be produced by subjecting compound (1-6) and compound (21) to an alkylation reaction in an inactive solvent and in the presence or absence of a base {see Comprehensive Organic Transformations, Second Edition, 1999, John Wiley & Sons, INC.}. As compound (21), a commercially available compound, a known compound, or a compound synthesized from such a commercially available compound or known compound according to various organic synthesis methods known to a person skilled in the art can be used.

Step 15: Compound (1-7) can be produced by reducing the carbonyl group of compound (22) in an inactive solvent {see Comprehensive Organic Transformations, Second Edition, 1999, John Wiley & Sons, INC.}. Examples of a reducing agent used herein include lithium aluminum hydride, sodium aluminum hydride, sodium bis(2-methoxyethoxy)aluminum hydride, diborane, and a borane-tetrahydrofuran complex.

Compound (1), which is represented by the formula (1-8), can be produced by the following method, for example.

<Scheme 10>

[Formula 11]

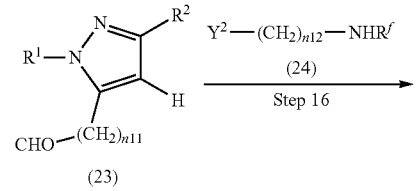

Step 16 →

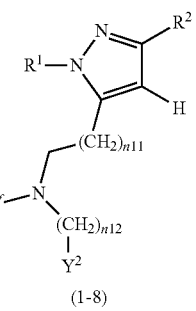
(1-8)

In the above formula, $R^1$, $R^2$, $R^f$ and $Y^2$ are defined as above. n11 and n12 each represent an integer from 0 to 5, provided that the sum of n11 and n12 is 5 or less.

Step 16: Compound (1-8) can be produced by allowing compound (23) to react with compound (24) using a reducing agent in an inactive solvent and in the presence or absence of an acid {see Comprehensive Organic Transformations, Second Edition, 1999, John Wiley & Sons, INC.}. Herein, as compound (23) and compound (24), commercially available compounds, known compounds, or compounds synthesized from such commercially available compounds or known compounds according to various organic synthesis methods known to a person skilled in the art can be used. In addition, examples of the reducing agent used herein include sodium triacetoxyborohydride, sodium cyanoborohydride, and sodium borohydride.

Compound (1), which is represented by the formula (1-9), can be produced by the following method, for example.

<Scheme 11>

[Formula 12]

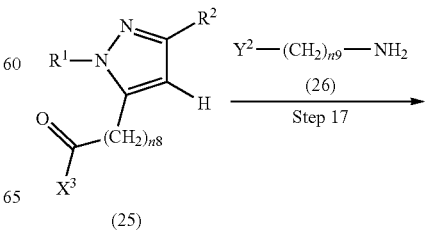

Step 17 →

-continued

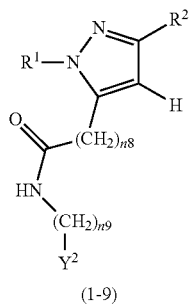

(1-9)

In the above formula, n8, n9, $R^1$, $R^2$, $X^3$ and $Y^2$ are defined as above.

Step 17: Compound (1-9) can be produced from compound (25) and compound (26) according to the same method as that in step 13 of <Scheme 9>. Herein, as compound (25) and compound (26), commercially available compounds, known compounds, or compounds synthesized from such commercially available compounds or known compounds according to various organic synthesis methods known to a person skilled in the art can be used.

Compound (1), which is represented by the formula (1-10), can be produced by the following method, for example.

<Scheme 12>

[Formula 13]

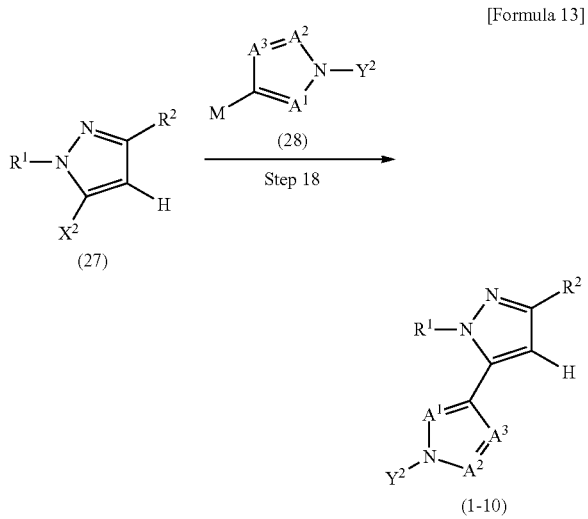

In the above formula, M, $R^1$, $R^2$, $X^2$ and $Y^2$ are defined as above. $A^1$, $A^2$, and $A^3$, which may be the same or different, each represent a nitrogen atom or CH.

Step 18: Compound (1-10) can be produced from compound (27) and compound (28) according to the same method as that in step 3 of <Scheme 2>. Herein, as compound (27) and compound (28), commercially available compounds, known compounds, or compounds synthesized from such commercially available compounds or known compounds according to various organic synthesis methods known to a person skilled in the art can be used.

Compound (1), which is represented by the formula (1-10'), can be produced by the following method, for example.

<Scheme 13>

[Formula 14]

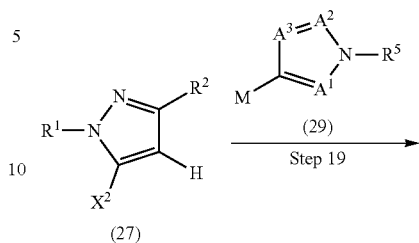

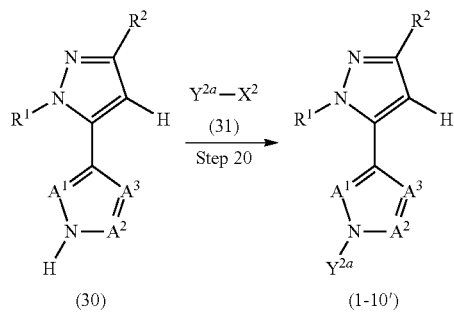

In the above formula, $A^1$, $A^2$, $A^3$, M, $R^1$, $R^2$ and $X^2$ are defined as above. $Y^{2a}$ represents an aryl group or a heteroaryl group {wherein the aryl group or the heteroaryl group may be substituted with 1 to 3 substituents selected from the group consisting of a $C_{1-6}$ alkyl group, a $C_{3-6}$ cycloalkyl group, a $C_{1-6}$ alkoxy group (wherein the $C_{1-6}$ alkyl group, $C_{3-6}$ cycloalkyl group or $C_{1-6}$ alkoxy group may be substituted with 1 to 3 halogen atoms), a cyano group, and a halogen atom}. $R^5$ represents a hydrogen atom, or a protecting group for amino group, such as a methoxymethyl group, a 2-(trimethylsilyl)ethoxymethyl group, a tert-butoxycarbonyl group, a benzyloxycarbonyl group, an acetyl group, a benzyl group, a trityl group, a methanesulfonyl group, a benzenesulfonyl group or a p-toluenesulfonyl group {see Protective Groups in Organic Synthesis, Fourth Edition, John Wiley & Sons, INC.}.

Step 19: Compound (30) can be produced by allowing compound (27) to react with compound (29), using a palladium catalyst and as necessary, a ligand, in an inactive solvent and in the presence or absence of a base, and then removing the protecting group $R^5$ according to various organic synthesis methods known to a person skilled in the art {see Protective Groups in Organic Synthesis, Fourth Edition, John Wiley & Sons, INC.}. Also, compound (30) can be directly produced, for example, by simultaneously carrying out a coupling reaction between compound (27) and compound (29) and the deprotection reaction of the protecting group $R^5$, using a palladium catalyst and as necessary, a ligand, in an inactive solvent and in the presence or absence of a base. Herein, as compound (27) and compound (29), commercially available compounds, known compounds, or compounds synthesized from such commercially available compounds or known compounds according to various organic synthesis methods known to a person skilled in the art can be used.

Step 20: Compound (1-10') can be produced by allowing compound (30) to react with compound (31), using a copper catalyst and as necessary, a ligand, in an inactive solvent and in the presence of a base. Herein, as compound (31), a commercially available compound, a known compound, or a compound synthesized from such a commercially available compound or known compound according to various organic synthesis methods known to a person skilled in the art can be used. Examples of the copper catalyst used herein include copper(0), copper(I) iodide, copper(I) chloride, copper(I) oxide, a copper(I) bromide tristriphenylphosphine complex, and a copper(I) trifluoromethanesulfonate benzene complex. As a ligand, a ligand used in a coupling reaction with a copper catalyst, which is known to person skilled in the art, can be used. Examples of such a ligand include N,N'-dimethylethylenediamine, 1,2-cyclohexanediamine, 2-aminopyridine, 1,10-phenanthroline, 2-hydroxybenzaldehyde oxime, and ethylene glycol [see Synlett, 15, 2428-2439, 2003].

Compound (1), which is represented by the formula (1-11), can be produced by the following method, for example.

<Scheme 14>

[Formula 15]

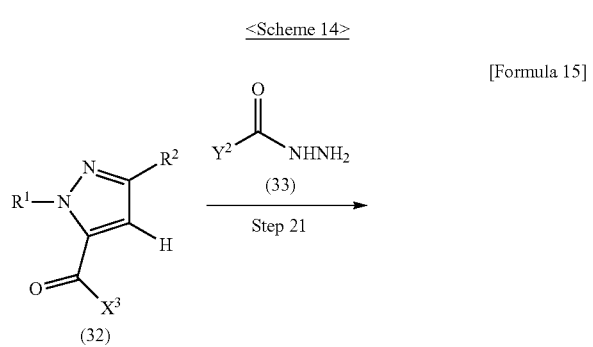

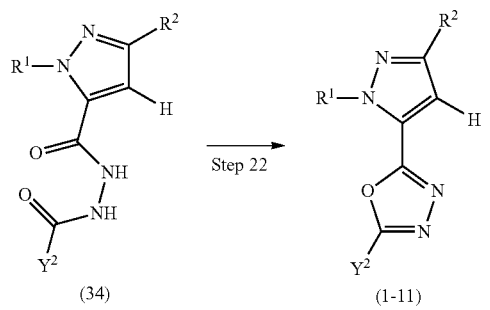

In the above formula, $R^1$, $R^2$, $X^3$ and $Y^2$ are defined as above.

Step 21: Compound (34) can be produced from compound (32) and compound (33) according to the same method as that in step 13 of <Scheme 9>. As compound (32) and compound (33), commercially available compounds, known compounds, or compounds synthesized from such commercially available compounds or known compounds according to various organic synthesis methods known to a person skilled in the art can be used.

Step 22: Compound (1-11) can be produced by subjecting compound (34) to an intramolecular cyclization reaction in an inactive solvent. In the present step, an activator such as tosyl chloride, thionyl chloride, phosphoryl chloride, or Burgess Reagent {methyl N-(triethylammoniumsulfonyl)carbamate} can be used, as necessary.

Compound (1), which is represented by the formula (1-12), can be produced by the following method, for example.

<Scheme 15>

[Formula 16]

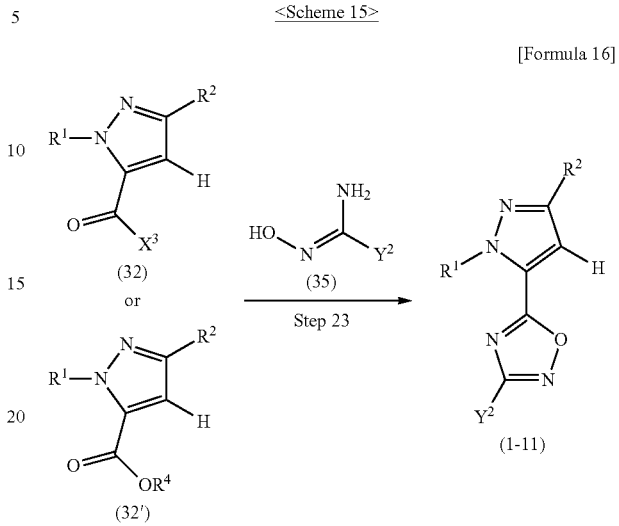

In the above formula, $R^1$, $R^2$, $R^4$, $X^3$ and $Y^2$ are defined as above.

Step 23: Compound (1-12) can be produced by subjecting compound (32) and compound (35) to an amidation reaction known to a person skilled in the art in an inactive solvent, and then subjecting the reaction product to the subsequent intramolecular cyclization reaction {see Comprehensive Organic Transformations, Second Edition, 1999, John Wiley & Sons, INC.}. Alternatively, compound (1-12) can also be produced by subjecting compound (32') and compound (35) to a condensation reaction in an inactive solvent and in the presence of a base, and then subjecting the reaction product to the subsequent intramolecular cyclization reaction. As compound (32), (32'), and (35), commercially available compounds, known compounds, or compounds synthesized from such commercially available compounds or known compounds according to various organic synthesis methods known to a person skilled in the art can be used. An example of the amidation reaction used herein is a condensation reaction of compound (32) in which $X^3$ is a halogen atom and compound (35), which is carried out in an inactive solvent and in the presence or absence of a base. Examples of the amidation reaction of compound (32) in which $X^3$ is a hydroxyl group include: a condensation reaction carried out in an inactive solvent and in the presence or absence of a base, using a condenser such as O-(7-azabenzotriazol-1-yl)-N,N,N',N-tetramethyluronium hexafluorophosphate (HATU), O-(benzotriazol-1-yl)-N,N,N',N-tetramethyluronium hexafluorophosphate (HBTU), N,N'-dicyclohexylcarbodiimide (DCC), 1-ethyl-3-(3-dimethylaminopropyl)carbodiimide hydrochloride (EDC.HCl), diphenylphosphoryl azide (DPPA) or carbonyldiimidazole (CDI); and a condensation reaction mediated by a mixed acid anhydride that is carried out in an inactive solvent and in the presence or absence of a base, using ethyl chloroformate, isobutyl chloroformate, trimethylacetyl chloride or the like. When an amidation reaction is carried out using a condenser, an additive such as 1-hydroxybenzotriazole (HOBt) or hydroxysuccinimide (HOSu) can be used, as necessary.

An example of the intramolecular cyclization reaction used herein is a reaction of cyclizing an amide compound that is carried out in an inactive solvent and under heated or unheated conditions, using an acid or a base as necessary.

Compound (1), which is represented by the formula (1-13), can be produced by the following method, for example.

<Scheme 16>

[Formula 17]

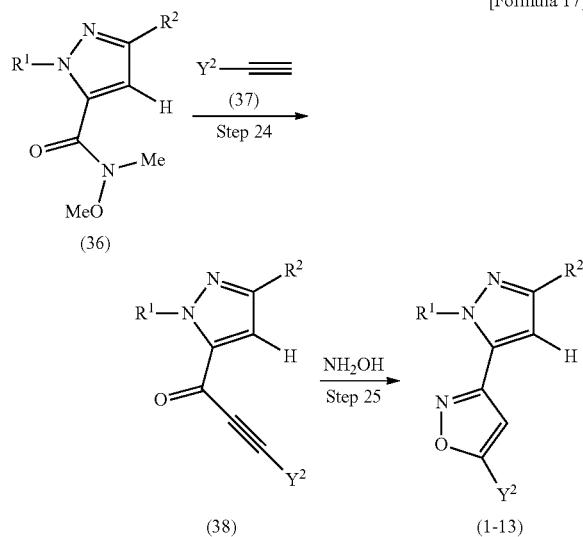

In the above formula, $R^1$, $R^2$ and $Y^2$ are defined as above.

Step 24: Compound (38) can be produced by subjecting compound (36) and compound (37) to an alkylation reaction in an inactive solvent and in the presence of a base. Herein, as compound (36) and compound (37), commercially available compounds, known compounds, or compounds synthesized from such commercially available compounds or known compounds according to various organic synthesis methods known to a person skilled in the art can be used.

Step 25: Compound (1-13) can be produced by subjecting compound (38) to a cyclization reaction using hydroxylamine or a salt thereof, in an inactive solvent, and in the presence or absence of a base, or in the presence or absence of an acid.

Compound (1), which is represented by the formula (1-14), can be produced by the following method, for example.

<Scheme 17>

[Formula 18]

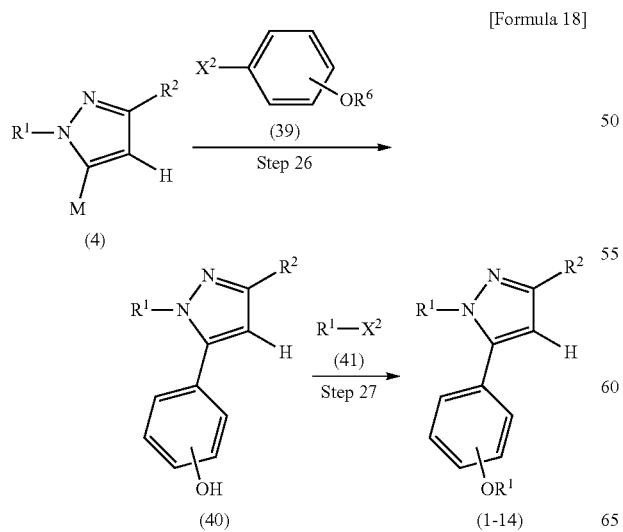

In the above formula, M, $R^1$, $R^2$ and $X^2$ are defined as above. $R^6$ represents a protecting group for hydroxyl group, such as a methoxymethyl group, a tert-butyldimethylsilyl group, an acetyl group, a benzyl group, a tetrahydropyranyl group or a 2-(trimethylsilyl)ethoxymethyl group {see Protective Groups in Organic Synthesis, Fourth Edition, John Wiley & Sons, INC.}, or a hydrogen atom.

Step 26: Compound (40) can be produced by performing a coupling reaction between compound (4) and compound (39) according to the same method as that in step 3 of <Scheme 2>, and then, when $R^6$ is a protecting group other than a hydrogen atom, removing the protecting group $R^6$ according to various organic synthesis methods known to a person skilled in the art {see Protective Groups in Organic Synthesis, Fourth Edition, John Wiley & Sons, INC.}. Herein, as compound (4) and compound (39), commercially available compounds, known compounds, or compounds synthesized from such commercially available compounds or known compounds according to various organic synthesis methods known to a person skilled in the art can be used.

Step 27: Compound (1-14) can be produced by subjecting compound (40) and compound (41) to an etherification reaction in an inactive solvent and in the presence or absence of a base {see Comprehensive Organic Transformations, Second Edition, 1999, John Wiley & Sons, INC.}. Herein, as compound (41), a commercially available compound, a known compound, or a compound synthesized from such a commercially available compound or known compound according to various organic synthesis methods known to a person skilled in the art can be used.

Compounds (2), which are represented by formulae (2-1) and (2-2), can be produced by the following method, for example.

<Scheme 18>

[Formula 19]

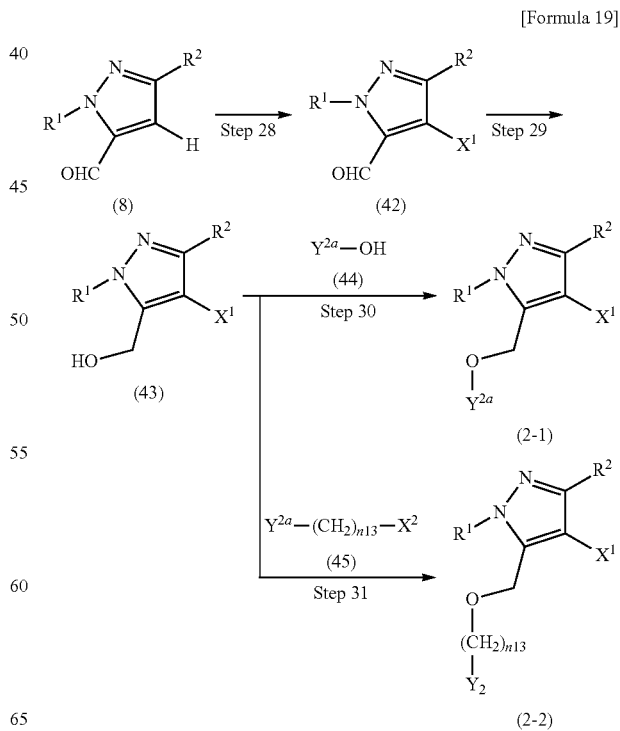

In the above formula, $R^1$, $R^2$, $X^1$, $X^2$, $Y^2$ and $Y^{2a}$ are defined as above. n13 represents an integer from 1 to 5.

Step 28: Compound (42) can be produced from compound (8) according to the same method as that in step 1 of <Scheme 1>. As compound (8), a commercially available compound, a known compound, or a compound synthesized from such a commercially available compound or known compound according to various organic synthesis methods known to a person skilled in the art can be used.

Step 29: Compound (43) can be produced by reducing compound (42) in an inactive solvent {see Comprehensive Organic Transformations, Second Edition, 1999, John Wiley & Sons, INC.}. The reducing agent used herein is a reagent capable of reducing a formyl compound to convert it to an alcohol compound. Examples of such a reducing agent include lithium borohydride, sodium borohydride, calcium borohydride, zinc borohydride, lithium aluminum hydride, sodium aluminum hydride, and aluminum diisobutyl hydride.

Step 30: Compound (2-1) can be produced by subjecting compound (43) and compound (44) to a Mitsunobu reaction in an inactive solvent. As compound (44), a commercially available compound, a known compound, or a compound synthesized from such a commercially available compound or known compound according to various organic synthesis methods known to a person skilled in the art can be used. Examples of the Mitsunobu reaction herein include: a reaction using an organophosphorus compound such as triphenylphosphine or tributylphosphine and an azo compound such as diethyl azodicarboxylate, diisopropyl azodicarboxylate, or ditertbutyl azodicarboxylate; and a reaction using a phosphorus ylide reagent such as cyanomethyl tributyl phospholan (see Chem. Rev. 2009. 109, 2551-2651).

Step 31: Compound (2-2) can be produced from compound (43) and compound (45) according to the same method as that in step 27 of <Scheme 17> {see Comprehensive Organic Transformations, Second Edition, 1999, John Wiley & Sons, INC.}. As compound (45), a commercially available compound, a known compound, or a compound synthesized from such a commercially available compound or known compound according to various organic synthesis methods known to a person skilled in the art can be used.

For example, compound (2), which is represented by the formula (2-3), can be produced by the following method.

In the above formula, $R^1$, $R^2$, $R^f$, $X^1$ and $Y^2$ are defined as above. n14 represents an integer from 0 to 5.

Step 32: Compound (2-3) can be produced from compound (42) and the compound (46) according to the same method as that in step 16 of <Scheme 10>. Herein, as compound (42) and the compound (46), commercially available compounds, known compounds, or compounds synthesized from such commercially available compounds or known compounds according to various organic synthesis methods known to a person skilled in the art can be used.

Compound (3) can be produced by the following method, for example.

<Scheme 20>

[Formula 21]

$$X^2-Ar \xrightarrow[\text{Step 33}]{R^7-\equiv\ (48)} R^7-\equiv-Ar \xrightarrow{\text{Step 34}} \equiv-Ar$$
(47) (49) (3)

In the above formula, Ar and $X^2$ are defined as above. $R^7$ represents a protecting group for terminal alkyne, such as a trimethylsilyl group, a triethylsilyl group or a triisopropylsilyl group [see Protective Groups in Organic Synthesis, Fourth Edition, John Wiley & Sons, INC.].

Step 33: Compound (49) can be produced from compound (47) and compound (48) according to the same method as that in step 2 of <Scheme 1>. Herein, as compound (47) and compound (48), commercially available compounds, known compounds, or compounds synthesized from such commercially available compounds or known compounds according to various organic synthesis methods known to a person skilled in the art can be used.

Step 34: Compound (3) can be produced by removing the protecting group $R^7$ for terminal alkyne from compound (49) according to various organic synthesis methods known to a person skilled in the art [see Protective Groups in Organic Synthesis, Fourth Edition, John Wiley & Sons, INC.].

[Production Method 2]

Compound [I] of the present invention can be produced by the following method.

<Scheme 19>

[Formula 20]

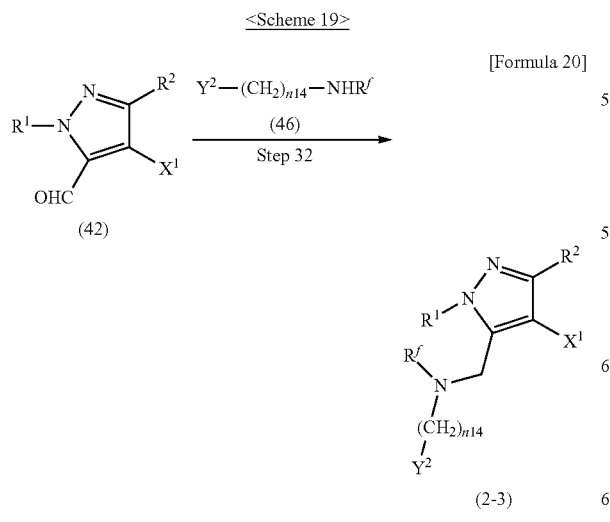

(42) → (2-3)

<Scheme 21>

[Formula 22]

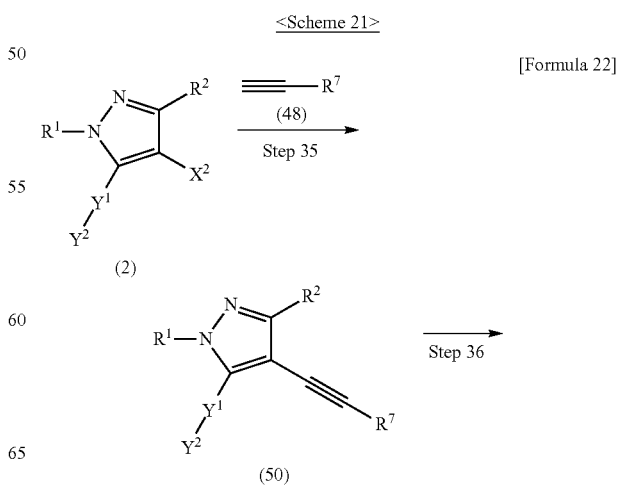

(2) → (50) Step 36

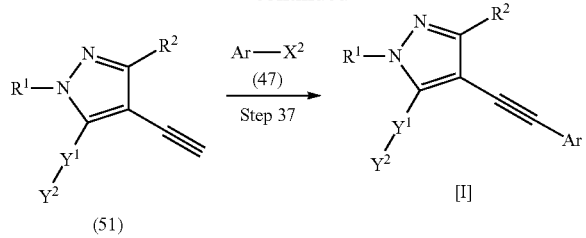

In the above formula, $R^1, R^2, R^7, X^2, Y^1$ and $Y^2$ are defined as above.

Step 35: Compound (50) can be produced from compound (2) and compound (48) according to the same method as that in step 2 of <Scheme 1>. Herein, as compound (2) and compound (48), commercially available compounds, known compounds, or compounds synthesized from such commercially available compounds or known compounds according to various organic synthesis methods known to a person skilled in the art can be used.

Step 36: Compound (51) can be produced from compound (50) according to the same method as that in step 34 of <Scheme 20>.

Step 37: Compound [I] of the present invention can be produced from compound (51) and compound (47) according to the same method as that in step 2 of <Scheme 1>. Herein, as compound (47), a commercially available compound, a known compound, or a compound synthesized from such a commercially available compound or known compound according to various organic synthesis methods known to a person skilled in the art can be used.

Compound (51) can be produced by the following method, for example.

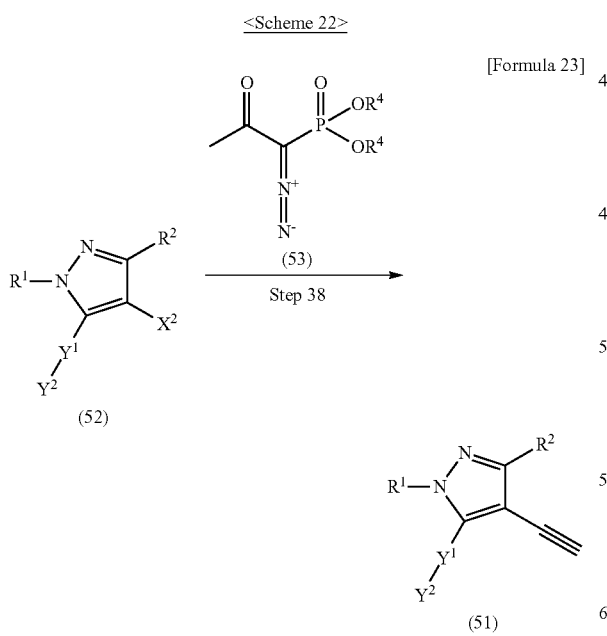

In the above formula, $R^1, R^2, R^4, Y^1$ and $Y^2$ are defined as above.

Step 38: Compound (51) can be produced by performing an alkynation reaction using compound (52) and compound (53) in an alcohol solvent and in the presence of a base. As compound (52) and compound (53), commercially available compounds, known compounds, or compounds synthesized from such commercially available compounds or known compounds according to various organic synthesis methods known to a person skilled in the art can be used. Herein, the alkynation reaction means an alkynation reaction known to a person skilled in the art, such as a reaction using the Ohira-Bestmann reagent, and this reaction can be carried out, for example, by the method described in Synlett, 1996, 521-522, a method equivalent thereto, or a combination of such a method with an ordinary method. Alternatively, compound (51) can also be produced by a Corey-Fuchs alkyne synthesis method (Synthesis, 2000, 185-213) or the like, which comprises allowing compound (52) to act on an organophosphorus compound such as triphenylphosphine and carbon tetrabromide in an inactive solvent and in the presence or absence of a base, and then treating the reaction product with a base.

Compounds (52), which are represented by formulae (52-1) to (52-3), can be produced by the following method, for example.

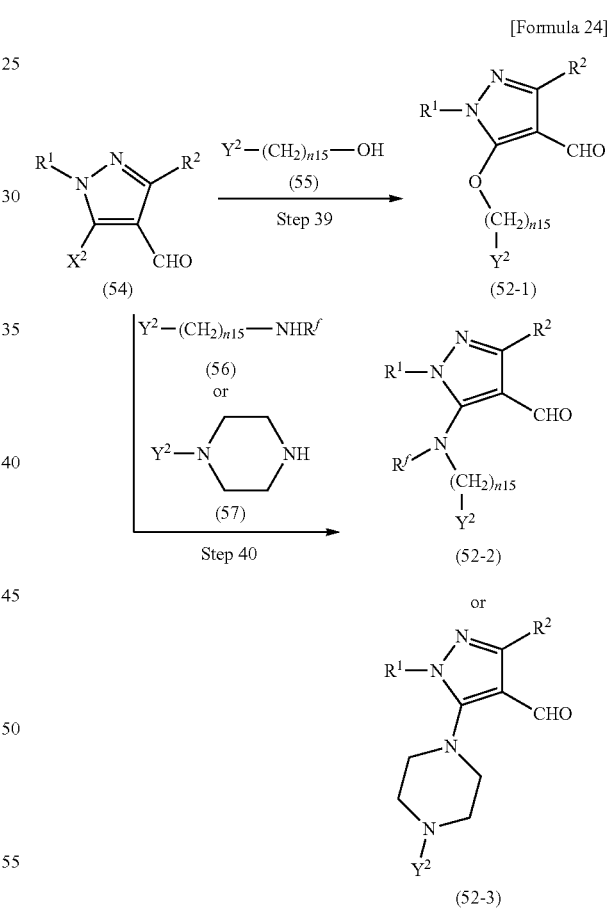

In the above formula, $R^1, R^2, R^f, X^2$ and $Y^2$ are defined as above. n15 represents an integer from 1 to 6.

Step 39: Compound (52-1) can be produced by subjecting compound (54) and compound (55) to an etherification reaction in an inactive solvent or in the absence of a solvent, and in the presence or absence of a base {see Comprehensive Organic Transformations, Second Edition, 1999, John Wiley & Sons, INC.}. Herein, as compounds (54) and (55), commercially available compounds, known compounds, or compounds synthesized from such commercially available compounds or known compounds according to various organic synthesis methods known to a person skilled in the art can be used.

Step 40: Compound (52-2) or compound (52-3) can be produced by subjecting compound (54) and compound (56) or compound (57) to an amination reaction in an inactive solvent or in the absence of a solvent, and in the presence or absence of a base {see Comprehensive Organic Transformations, Second Edition, 1999, John Wiley & Sons, INC.}. As compounds (54), (56) and (57), commercially available compounds, known compounds, or compounds synthesized from such commercially available compounds or known compounds according to various organic synthesis methods known to a person skilled in the art can be used.

[Production Method 3]

Compounds [I-II] and [I-III] of the present invention can be produced from compound [I-I] of the present invention by the following method.

Step 41: Compound [I-II] of the present invention can be produced by removing the protecting group $R^8$ for sulfo group from compound of the present invention represented by the formula [I-I] according to various organic synthesis methods known to a person skilled in the art [see Protective Groups in Organic Synthesis, Fourth Edition, John Wiley & Sons, INC.].

Step 42: Compound (58) can be produced by allowing compound [I-II] of the present invention to react with a halogenating agent such as thionyl chloride or oxalyl chloride in an inactive solvent or in the absence of a solvent.

Step 43: Compound [I-III] of the present invention can be produced by subjecting compound (58) and compound (59) to a sulfonamidation reaction in an inactive solvent or in the absence of a solvent, and in the presence or absence of a base. As compound (59), a commercially available compound, a known compound, or a compound synthesized from such a commercially available compound or known compound according to various organic synthesis methods known to a person skilled in the art can be used.

[Production Method 4]

Compounds [I-V] and [I-VI] of the present invention can be produced by the following method.

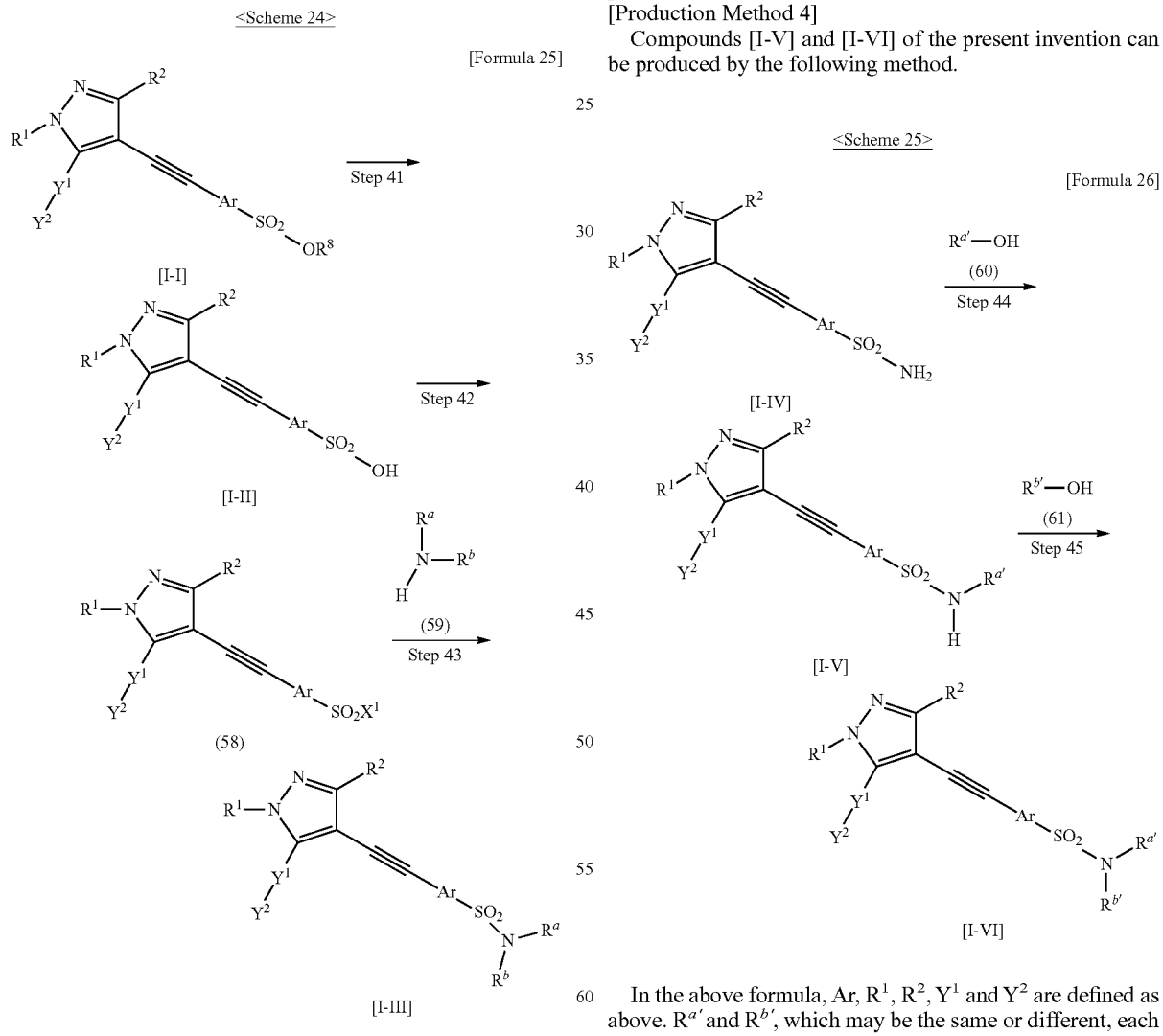

In the above formula, Ar, $R^1$, $R^2$, $R^a$, $R^b$, $X^1$, $Y^1$ and $Y^2$ are defined as above. $R^8$ represents a protecting group for sulfo group, such as an isobutyl group or a neopentyl group [see Protective Groups in Organic Synthesis, Fourth Edition, John Wiley & Sons, INC.].

In the above formula, Ar, $R^1$, $R^2$, $Y^1$ and $Y^2$ are defined as above. $R^{a'}$ and $R^{b'}$, which may be the same or different, each represent a $C_{1-6}$ alkyl group (wherein the $C_{1-6}$ alkyl group may be substituted with 1 or 2 substituents selected from the group consisting of an amino group, a $C_{1-6}$ alkylamino group, a di-$C_{1-6}$ alkylamino group, and a hydroxyl group), or $R^{a'}$ and $R^{b'}$ may form a saturated or unsaturated 5- or 6-membered ring, which is formed together with a nitrogen atom to which they bind, and which may further contain one or more nitrogen atoms, oxygen atoms or sulfur atoms.

Step 44: Compound [I-V] of the present invention can be produced from compound [I-IV] of the present invention, in which both $R^a$ and $R^b$ are hydrogen atoms in compound [I-III] of the present invention in <Scheme 24>, and compound (60), according to the same method as that in step 30 of <Scheme 18>.

Step 45: Compound [I-VI] of the present invention can be produced from compound [I-V] of the present invention and compound (61), according to the same method as that in step 30 of <Scheme 18>.

[Production Method 5]

Compounds [I-VII] and [I-VIII] of the present invention can be produced by the following method.

to the same method as that in step 30 of <Scheme 18>. As compound (44), a commercially available compound, a known compound, or a compound synthesized from such a commercially available compound or known compound according to various organic synthesis methods known to a person skilled in the art can be used.

Step 49: Compound [I-VIII] of the present invention can be produced from compound (64) and compound (45) according to the same method as that in step 27 of <Scheme 17>. As compound (45), a commercially available compound, a known compound, or a compound synthesized from such a commercially available compound or known compound according to various organic synthesis methods known to a person skilled in the art can be used.

<Scheme 26>

[Formula 27]

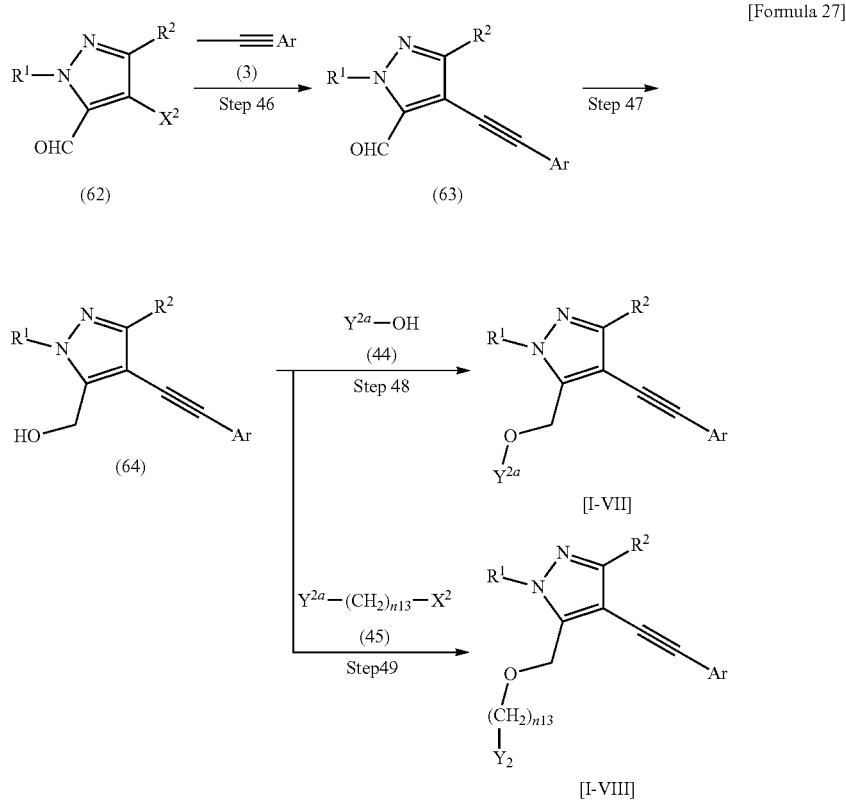

In the above formula, n13, Ar, $R^1$, $R^2$, $X^2$, $Y^2$ and $Y^{2a}$ are defined as above.

Step 46: Compound (63) can be produced from compound (62) and compound (3) according to the same method as that in step 2 of <Scheme 1>. Herein, as compound (62) and compound (3), a commercially available compound, a known compound, or a compound synthesized from such a commercially available compound or known compound according to various organic synthesis methods known to a person skilled in the art can be used.

Step 47: Compound (64) can be produced from compound (63) according to the same method as that in step 29 of <Scheme 18>.

Step 48: Compound [I-VII] of the present invention can be produced from compound (64) and compound (44) according

[Production Method 6]

Compound [I-IX] of the present invention can be produced by the following method.

<Scheme 27>

[Formula 28]

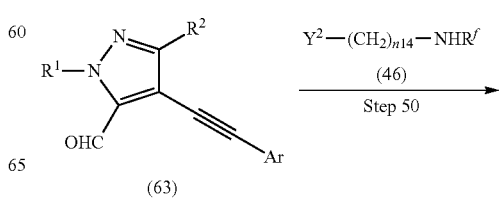

-continued

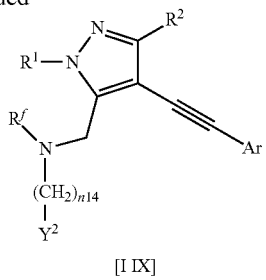

[I-IX]

In the above formula, n14, Ar, $R^1$, $R^2$, $R^f$ and $Y^2$ are defined as above.

Step 50: Compound [I-IX] of the present invention can be produced from compound (63) and compound (46) according to the same method as that in step 16 of <Scheme 10>. As compound (63) and compound (46), commercially available compounds, known compounds, or compounds synthesized from such commercially available compounds or known compounds according to various organic synthesis methods known to a person skilled in the art can be used.

[Production Method 7]

Compound [I-XI] of the present invention can be produced by the following method.

<Scheme 28>

[Formula 29]

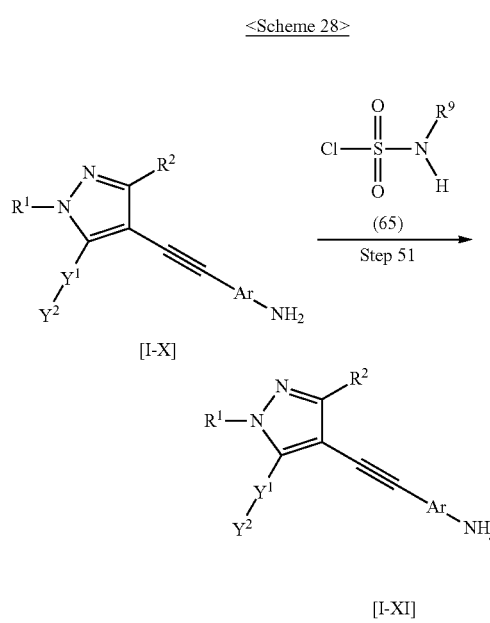

In the above formula, Ar, $R^1$, $R^2$, $Y^1$ and $Y^2$ are defined as above. $R^9$ represents a hydrogen atom, or a protecting group for sulfamoyl group, such as a methoxymethyl group, a trimethylsilylethoxymethyl group, a tert-butoxycarbonyl group, a benzyloxycarbonyl group, an acetyl group or a benzyl group [see Protective Groups in Organic Synthesis, Fourth Edition, John Wiley & Sons, INC.].

Step 51: Compound [I-XI] of the present invention can be produced by subjecting compound [I-X] of the present invention and compound (65) to a sulfonamidation reaction in an inactive solvent, and then, when $R^9$ is a protecting group other than a hydrogen atom, removing the protecting group $R^9$ according to various organic synthesis methods known to a person skilled in the art [see Protective Groups in Organic Synthesis, Fourth Edition, John Wiley & Sons, INC.].

[Production Method 8]

Compound [I-XII] of the present invention can be produced by the following method.

<Scheme 29>

[Formula 30]

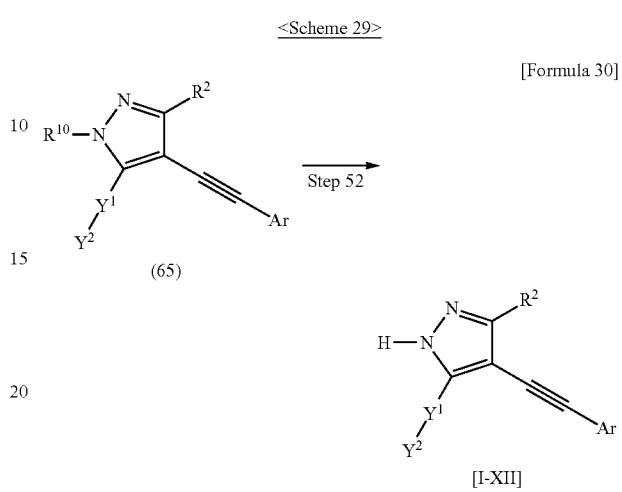

In the above formula, Ar, $R^2$, $Y^1$ and $Y^2$ are defined as above. $R^{10}$ represents a protecting group for the nitrogen atom on the pyrazole ring, such as a 2-(trimethylsilyl)ethoxymethyl group, a tert-butoxycarbonyl group, a benzyloxycarbonyl group, an acetyl group, a benzyl group, a trityl group, a methanesulfonyl group, a benzenesulfonyl group, or a p-toluenesulfonyl group [see Protective Groups in Organic Synthesis, Fourth Edition, John Wiley & Sons, INC.].

Step 52: Compound [I-XII] of the present invention can be produced by removing the protecting group $R^{10}$ from compound (65) according to various organic synthesis methods known to a person skilled in the art [see Protective Groups in Organic Synthesis, Fourth Edition, John Wiley & Sons, INC.].

Compound (65-1) can be produced by the following method, for example.

<Scheme 30>

[Formula 31]

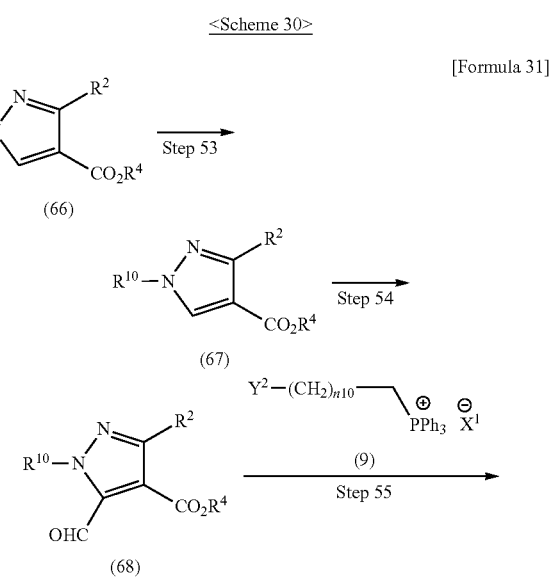

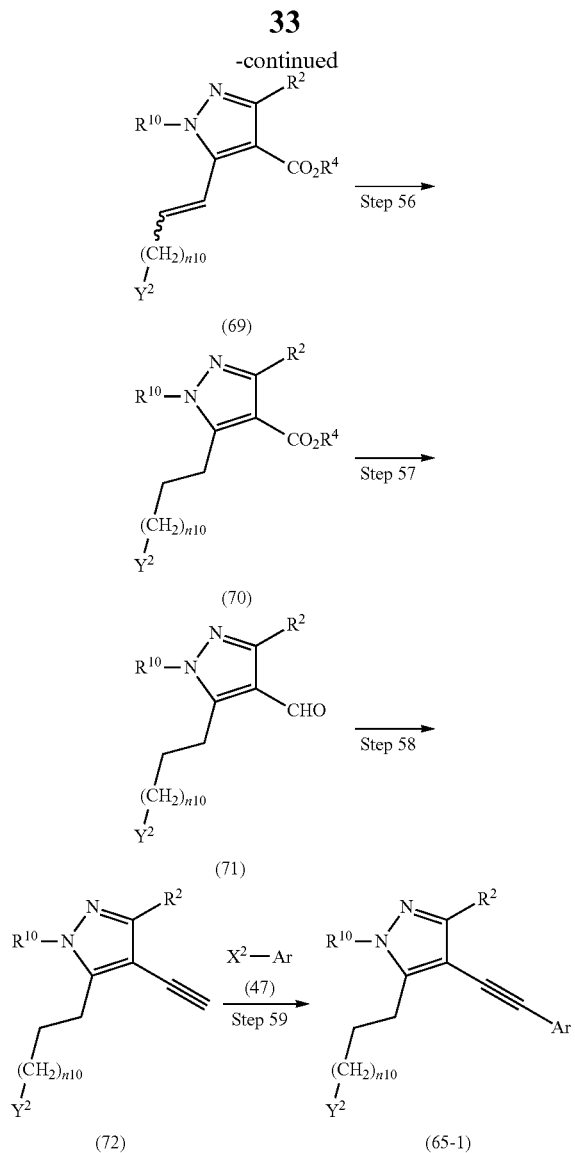

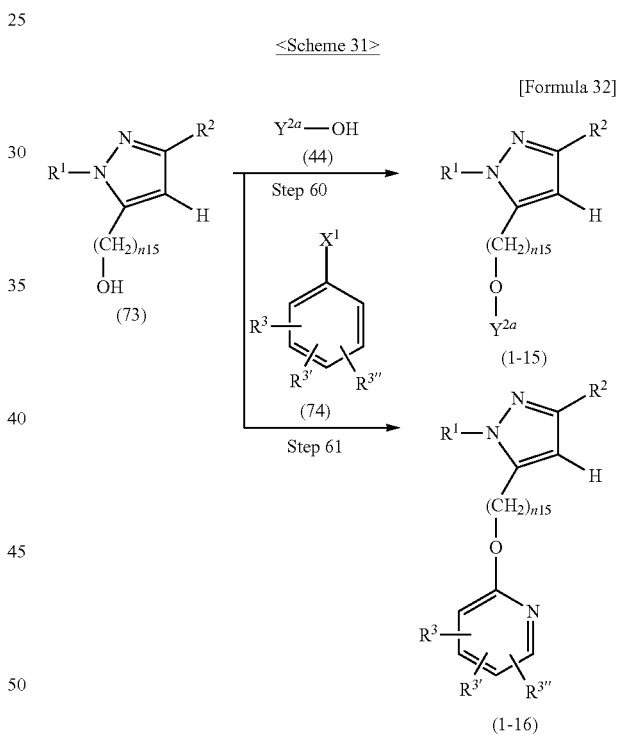

In the above formula, Ar, n10, $R^2$, $R^4$, $R^{10}$, $X^1$, $X^2$ and $Y^2$ are defined as above.

Step 53: Compound (67) can be produced by protecting the nitrogen atom on the pyrazole ring from compound (66) by the protecting group $R^{10}$ according to various organic synthesis methods known to a person skilled in the art [see Protective Groups in Organic Synthesis, Fourth Edition, John Wiley & Sons, INC.]. Herein, as compound (66), a commercially available compound, a known compound, or a compound synthesized from such a commercially available compound or known compound according to various organic synthesis methods known to a person skilled in the art can be used.

Step 54: Compound (68) can be produced by allowing compound (67) to react with N,N-dimethylformamide or the like in an inactive solvent and in the presence of a base.

Step 55: Compound (69) can be produced from compound (68) according to the same method as that in step 6 of <Scheme 4>. As compound (9), a commercially available compound, a known compound, or a compound synthesized from such a commercially available compound or known compound according to various organic synthesis methods known to a person skilled in the art can be used.

Step 56: Compound (70) can be produced from compound (69) according to the same method as that in step 5 of <Scheme 3>.

Step 57: Compound (71) can be produced by reducing compound (70) in an inactive solvent according to various organic synthesis methods known to a person skilled in the art {see Comprehensive Organic Transformations, Second Edition, 1999, John Wiley & Sons, INC.}. Examples of such a reducing agent used herein include reagents capable of reducing an ester to convert it to an aldehyde, such as lithium borohydride, sodium borohydride, calcium borohydride, zinc borohydride, lithium aluminum hydride, sodium aluminum hydride, and aluminum diisobutyl hydride.

Step 58: Compound (72) can be produced from compound (71) according to the same method as that in step 38 of <Scheme 22>.

Step 59: Compound (65-1) can be produced from compound (73) and compound (47) according to the same method as that in step 2 of <Scheme 1>.

Compound (1), which is represented by the formula (1-15) and the formula (1-16), can be produced by the following method, for example.

In the above formula, n15, $R^1$, $R^2$, $X^1$ and $Y^{2a}$ are defined as above. $R^3$, $R^{3'}$ and $R^{3''}$, which may be the same or different, each represent a $C_{1-6}$ alkyl group, a $C_{3-6}$ cycloalkyl group, a $C_{1-6}$ alkoxy group (wherein the $C_{1-6}$ alkyl group, $C_{3-6}$ cycloalkyl group, or $C_{1-6}$ alkoxy group may be substituted with 1 to 3 halogen atoms), a cyano group, or a halogen atom.

Step 60: Compound (1-15) can be produced from compound (73) and compound (44) according to the same method as that in step 30 of <Scheme 18>. Herein, as the compounds (44) and (73), commercially available compounds, known compounds, or compounds synthesized from such commercially available compounds or known compounds according to various organic synthesis methods known to a person skilled in the art can be used.

Step 61: Compound (1-16) can be produced by allowing compound (73) to react with compound (74) in an inactive solvent, in the presence of a base, and in the presence or absence of a palladium catalyst and a palladium catalyst ligand {see Comprehensive Organic Transformations, Second Edition, 1999, John Wiley & Sons, INC.}. Examples of the palladium catalyst used herein include palladium(II) acetate, dichlorobistriphenylphosphine palladium(II), dichlorobisacetonitrile palladium(II), and tetrakistriphenylphosphine palladium(0). Examples of the ligand used herein include rac-2-(di-t-butylphosphino)-1,1'-binaphthyl, triphenylphosphine, tributylphosphine, 2,2-bis(diphenylphosphino)-1,1-binaphthyl(BINAP), 2-(di-tert-butylphosphino)biphenyl, 1,1'-bis(diphenylphosphino)ferrocene (dppf), and 1,3-bis(diphenylphosphino)propane (dppp). Herein, as compounds (73) and (74), commercially available compounds, known compounds, or compounds synthesized from such commercially available compounds or known compounds according to various organic synthesis methods known to a person skilled in the art can be used.

EXAMPLES

Hereinafter, the present invention will be described more in detail in the following Production Examples, Example, and Test Examples. However, these Production Examples, Examples, and Test Examples are not intended to limit the scope of the present invention. In addition, these examples may be modified without departing from the scope of the present invention.

In the Production Examples and the Example, the following commercially available products were used to carry out various types of purification. That is, in order to carry out purification with the use of column chromatography, Biotage (registered trademark) SNAP Cartridge KP-NH manufactured by Biotage Japan Ltd. was used as an "NH silica gel cartridge," and Biotage (registered trademark) SNAP Cartridge KP-Sil and HP-Sil, manufactured by Biotage Japan Ltd., were used as "silica gel cartridges". Likewise, Silica Gel 60N manufactured by Kanto Chemical Co., Inc. was used as a "silica gel 60N," and Chromatorex (registered trademark) NH manufactured by Fuji Silysia Chemical Ltd. was used as a "chromatorex NH." In order to carry out purification with the use of reverse-phase column chromatography, CAPCELL PAK (registered trademark) C18 TYPE MG II manufactured by Shiseido Co., Ltd. was used as "CAPCELL PAK." In order to carry out purification with the use of TLC, Silica gel 60F254 (Merck) was used as a TLC (silica gel plate), and TLC Plate (NH) (Fuji Silysia Chemical Ltd.) was used as a TLC (NH silica gel plate).

The device data described in the Production Examples and the Example were measured using the following measurement devices.

Microwave reactor: Initiator (Biotage AB)
MS spectrum: Shimadzu LCMS-2010 EV, Micromass Platform LC or Micromass GCT
NMR spectrum: [$^1$H-NMR] 600 MHz: JNM-ECA 600 (JEOL Ltd.), 500 MHz: JNM-ECA500 (JEOL Ltd.), 300 MHz: UNITYNOVA 300 (Varian Inc.), 200 MHz: GEMINI 2000/200 (Varian Inc.)

Compound names used in the Production Examples and Examples were denominated in accordance with ACD/Name (ACD/Labs 12.0, Advanced Chemistry Development Inc.).

The abbreviations used in the nuclear magnetic resonance (NMR) spectra in the Production Examples and Examples have the following definitions.

s: singlet, d: doublet, t: triplet, q: quartet, dd: double doublet, dt: double triplet, dq: double quartet, ddd: double double doublet, m: multiplet, br: broad, J: coupling constant, Hz: hertz, DMSO-$d_6$: deuterated dimethyl sulfoxide Production Example 1

3-Bromo-N-[2-(dimethylamino)ethyl]benzenesulfonamide

Under cooling in an ice bath, N,N'-dimethylethylenediamine (414 mg) and triethylamine (1.10 mL) were added to a chloroform (10 mL) solution of 3-bromobenzenesulfonyl chloride (1.00 g), and the obtained solution was then stirred at a room temperature for 45 minutes. The reaction solution was washed with water, and was then dried over anhydrous sodium sulfate, followed by vacuum concentration. The residue was purified by column chromatography (silica gel 60N, chloroform:methanol=98:2 to 96:4), so as to obtain the title compound (1.14 g) in the form of a colorless solid.

1H NMR (600 MHz, CHLOROFORM-d) δ ppm 2.07-2.09 (m, 6H) 2.30-2.34 (m, 2H) 2.96-3.00 (m, 2H) 7.39 (t, J=8.02 Hz, 1H) 7.69 (ddd, J=7.79, 1.83, 0.92 Hz, 1H) 7.80 (dt, J=7.68, 1.43 Hz, 1H) 8.02 (t, J=1.83 Hz, 1H); MS (ESI pos.) m/z: 307 [M+H]$^+$ The following compounds were synthesized in the same manner as above.

3-Bromo-N-(1,3-dihydroxy-2-methylpropan-2-yl)benzenesulfonamide
  MS (ESI pos.) m/z: 324 [M+H]$^+$
3-Bromo-N-[2-(dimethylamino)ethyl]-N-methylbenzenesulfonamide
  MS (ESI pos.) m/z: 321 [M+H]+
3-Bromo-N-[3-(dimethylamino)propyl]benzenesulfonamide
  MS (ESI pos.) m/z: 321 [M+H]+
4-Bromo-N-[2-(dimethylamino)ethyl]benzenesulfonamide
  MS (ESI pos.) m/z: 307 [M+H]+

Production Example 2

2,2-Dimethylpropyl 3-bromobenzenesulfonate

Under cooling in an ice bath, 2,2-dimethyl-1-propanol (1.55 g) was added to a chloroform (20 mL) solution that contained 3-bromobenzenesulfonyl chloride (3.00 g) and pyridine (1.86 g), and the obtained solution was then stirred at a room temperature for 60 hours. Thereafter, water and a saturated sodium hydrogencarbonate aqueous solution were added to the reaction solution, and the obtained mixture was then extracted with chloroform. The organic layer was washed with a saturated saline, and was then dried over anhydrous sodium sulfate, followed by vacuum concentration. The obtained solid was washed with n-hexane, so as to obtain the title compound (3.90 g) in the form of a colorless solid.

1H NMR (200 MHz, CHLOROFORM-d) δ ppm 0.92 (s, 9H) 3.72 (s, 2H) 7.38-7.51 (m, 1H) 7.74-7.89 (m, 2H) 8.02-8.08 (m, 1H); MS (EI pos.) m/z: 306 (M)$^+$ Production Example 3

3-ethynylbenzenesulfonamide 1) 3-[(trimethylsilyl)ethynyl]benzenesulfonamide

A dimethylformamide (30 mL) solution of 3-bromobenzenesulfonamide (13.7 g), trimethylsilylacetylene (5.18 g), copper(I) iodide (65 mg), bis(triphenylphosphine)palladium (II) dichloride (400 mg), triphenylphosphine (300 mg) and triethylamine (15.0 mL) was stirred at 80° C. for 6 hours. Thereafter, the reaction solution was added to water, and the obtained solution was then extracted with ethyl acetate. The organic layer was successively washed with water and a saturated saline, and was then dried over anhydrous magnesium sulfate, followed by vacuum concentration. The residue was purified by column chromatography (silica gel 60 N, hexane: ethyl acetate=4:1 to 3:1), so as to obtain the title compound (11.4 g) in the form of a light brown solid.

1H NMR (600 MHz, CHLOROFORM-d) δ ppm 0.25 (s, 9H) 4.94 (s, 2H) 7.45 (t, J=7.79 Hz, 1H) 7.63 (dt, J=7.68, 1.20 Hz, 1H) 7.84 (dq, J=7.85, 1.05 Hz, 1H) 8.01 (t, J=1.60 Hz, 1H); MS (ESI neg.) m/z: 252 [M−H]⁻

2) 3-Ethynylbenzenesulfonamide

Under cooling in an ice bath, potassium carbonate (610 mg) was added to a tetrahydrofuran (30 mL) and methanol (70 mL) solution of 3-[(trimethylsilyl)ethynyl]benzenesulfonamide (11.1 g), and the obtained solution was then stirred at a room temperature for 12 hours. Thereafter, water was added to the reaction solution, and the solvent was then distilled away under a reduced pressure. Then, the residue was extracted with diethyl ether. The organic layer was washed with water and a saturated saline, and was then dried over anhydrous magnesium sulfate, followed by vacuum concentration. The residue was purified by column chromatography (silica gel 60N, hexane:ethyl acetate=2:1 to 1:1), so as to obtain the title compound (5.84 g) in the form of a light brown solid.

1H NMR (600 MHz, DMSO-d₆) δ ppm 4.36 (s, 1H) 7.42 (s, 2H) 7.57 (t, J=7.80 Hz, 1H) 7.67 (dt, J=7.79, 1.38 Hz, 1H) 7.81 (dt, J=7.91, 1.55 Hz, 1H) 7.85 (t, J=1.60 Hz, 1H); MS (ESI neg.) m/z: 180 [M−H]⁻

The following compounds were synthesized in the same manner as above.
4-ethynylbenzenesulfonamide
  MS (ESI neg.) m/z: 180 [M−H]⁻
5-ethynyl-2-(methylsulfonyl)pyridine
  MS (ESI pos.) m/z: 182 [M+H]⁺
2-ethynyl-5-(methylsulfonyl)pyridine
  MS (ESI pos.) m/z: 182 [M+H]⁺
4-ethynyl-2-fluorobenzenesulfonamide
  MS (ESI neg.) m/z: 198 [M−H]⁻
4-ethynyl-3-fluorobenzenesulfonamide
  MS (ESI neg.) m/z: 198 [M−H]⁻
4-ethynylbenzenesulfonic acid 2,2-dimethylpropyl
  MS (EI pos.) m/z: 252 [M+H]⁺
2-ethynyl-3-fluoro-5-(trifluoromethyl)pyridine
  MS (ESI pos.) m/z: 190 [M+H]⁺

Production Example 4

1-Methyl-5-[4-(trifluoromethyl)phenyl]-1H-pyrazole

Under a nitrogen atmosphere, a mixture of 1-methyl-5-(4,4,5,5-tetramethyl-1,3,2-dioxaborolan-2-yl)-1H-pyrazole (4.00 g), 4-iodobenzotrifluoride (4.03 g), bis(triphenylphosphine)palladium(II) dichloride (312 mg), potassium carbonate (2.65 g), ethanol (10 mL) and dimethylformamide (20 mL) was stirred at 75° C. for 2 hours. Thereafter, the reaction solution was diluted with ethyl acetate, and was then washed with water. The organic layer was dried over anhydrous magnesium sulfate, and was then concentrated under a reduced pressure. The residue was purified by column chromatography (silica gel 60N, hexane:ethyl acetate=4:1 to 3:1), so as to obtain the title compound (3.70 g) in the form of a brownish-red solid.

1H NMR (600 MHz, CHLOROFORM-d) δ ppm 3.91 (s, 3H) 6.36 (d, J=1.83 Hz, 1H) 7.49-7.58 (m, 3H) 7.72 (d, J=8.25 Hz, 2H); MS (ESI pos.) m/z: 227 [M+H]⁺

The following compounds were synthesized in the same manner as above.
5-(biphenyl-4-yl)-1-methyl-1H-pyrazole
  MS (ESI pos.) m/z: 235 [M+H]⁺
1-methyl-5-(naphthalen-2-yl)-1H-pyrazole
  MS (ESI pos.) m/z: 209 [M+H]⁺
1-methyl-5-phenyl-1H-pyrazole
  MS (ESI pos.) m/z: 159 [M+H]⁺
1-methyl-5-[3-(trifluoromethyl)phenyl]-1H-pyrazole
  MS (ESI pos.) m/z: 227 [M+H]⁺
1-methyl-5-[2-(trifluoromethyl)phenyl]-1H-pyrazole
  MS (ESI pos.) m/z: 227 [M+H]⁺
1-methyl-5-[4-(trifluoromethoxy)phenyl]-1H-pyrazole
  MS (ESI pos.) m/z: 243 [M+H]⁺
5-(1-methyl-1H-pyrazol-5-yl)-2-(trifluoromethyl)pyridine
  MS (ESI pos.) m/z: 228 [M+H]⁺
2-(1-methyl-1H-pyrazol-5-yl)-5-(trifluoromethyl)pyridine
  MS (ESI pos.) m/z: 228 [M+H]⁺
2-(1-methyl-1H-pyrazol-5-yl)-5-phenylpyridine
  MS (ESI pos.) m/z: 236 [M+H]⁺
2-(1-methyl-1H-pyrazol-5-yl)quinoline
  MS (ESI pos.) m/z: 210 [M+H]⁺
5-(1-methyl-1H-pyrazol-5-yl)-2-phenylpyridine
  MS (ESI pos.) m/z: 236 [M+H]⁺
4-(1-methyl-1H-pyrazol-5-yl)phenol
  MS (ESI pos.) m/z: 175 [M+H]⁺

Production Example 5

1-Methyl-5-[4-(2,2,2-trifluoroethoxy)phenyl]-1H-pyrazole

A mixture of 4-(1-methyl-1H-pyrazol-5-yl)phenol (500 mg), 2,2,2-trifluoroethyl trifluoromethanesulfonate (999 mg), potassium carbonate (793 g) and acetonitrile (5.0 mL) was stirred at 90° C. for 2 hours. Thereafter, the reaction solution was diluted with chloroform, and insoluble matters were then removed by filtration. The filtrate was concentrated under a reduced pressure, and the residue was then purified by column chromatography (silica gel 60N, chloroform:methanol=100:0 to 98:2), so as to obtain the title compound (485 mg) in the form of a light yellow solid.

1H NMR (600 MHz, CHLOROFORM-d) δ ppm 4.40 (q, J=7.79 Hz, 2H) 6.26 (d, J=1.83 Hz, 1H) 6.99-7.05 (m, 2H) 7.34-7.39 (m, 2H) 7.50 (d, J=1.83 Hz, 1H); MS (ESI pos.) m/z: 257 [M+H]⁺

Production Example 6

3-[4-(1-Methyl-1H-pyrazol-5-yl)phenyl]pyridine 1) 4-(1-Methyl-1H-pyrazol-5-yl)phenyl trifluoromethanesulfonate N-phenylbis(trifluoromethanesulfonimide) (1.14 g) was added to a dimethylformamide (9.7 mL) solution that contained 4-(1-methyl-1H-pyrazol-5-yl)phenol (506 mg) and triethylamine (810 μL) at a room temperature, and the obtained solution was then stirred for 20 hours. Thereafter, water was added to the reaction solution, and the obtained mixture was then extracted with ethyl acetate. The organic layer was washed with water and a saturated saline, and was then dried over anhydrous magnesium sulfate, followed by vacuum concentration. The residue was purified by column chromatography (silica gel cartridge, hexane:ethyl acetate=7:3 to 6:4), so as to obtain the title compound (892 mg) in the form of a colorless oily substance.

$^1$H NMR (200 MHz, CHLOROFORM-d) δ ppm 3.90 (s, 3H) 6.34 (d, J=2.20 Hz, 1H) 7.34-7.45 (m, 2H) 7.47-7.56 (m, 3H)

2) 3-[4-(1-Methyl-1H-pyrazol-5-yl)phenyl]pyridine

A mixture of 4-(1-methyl-1H-pyrazol-5-yl)phenyl trifluoromethanesulfonate (200 mg), 3-pyridylboronic acid (88 mg), bis(triphenylphosphine)palladium(II) dichloride (14 mg), potassium carbonate (135 mg), dimethylformamide (1.4 mL) and ethanol (0.70 mL) was reacted in a microwave reactor (80° C., 25 minutes). Thereafter, water was added to the reaction solution, and the obtained mixture was extracted with ethyl acetate. The organic layer was washed with water and a saturated saline, and was then dried over anhydrous magnesium sulfate, followed by vacuum concentration, so as to obtain the title compound (220 mg) in the form of a light yellow oily substance.

$^1$H NMR (600 MHz, CHLOROFORM-d) δ ppm 3.94 (s, 3H) 6.36 (d, J=1.83 Hz, 1H) 7.37-7.42 (m, 1H) 7.52-7.55 (m, 3H) 7.66-7.69 (m, 2H) 7.91 (dt, J=8.02, 1.72 Hz, 1H) 8.63 (d, J=4.59 Hz, 1H) 8.89 (d, J=1.83 Hz, 1H); MS (ESI pos.) m/z 236 [M+H]$^+$.

The following compound was synthesized in the same manner as above.
5-[4-(Cyclopenta-1-ene-1-yl)phenyl]-1-methyl-1H-pyrazole
MS (ESI pos.) m/z 225 [M+H]+

Production Example 7

5-(4-Cyclopentylphenyl)-1-methyl-1H-pyrazole

10% palladium carbon (20 mg) was added to an ethanol (2.4 mL) solution of 5-[4-(cyclopenta-1-ene-1-yl)phenyl]-1-methyl-1H-pyrazole (133 mg), and the obtained solution was then stirred under a hydrogen atmosphere at a room temperature overnight. Thereafter, the reaction solution was filtrated with Celite, and the filtrate was then concentrated under a reduced pressure, so as to obtain the title compound (140 mg) in the form of a light yellow oily substance.

$^1$H NMR (600 MHz, CHLOROFORM-d) δ ppm 1.61-1.69 (m, 2H) 1.71-1.80 (m, 2H) 1.84-1.91 (m, 2H) 2.11-2.18 (m, 2H) 3.05-3.12 (m, 1H) 3.98 (s, 3H) 6.39 (s, 1H) 7.35-7.40 (m, 4H) 7.66 (s, 1H)

Production Example 8

1-Methyl-5-(2-phenylethyl)-1H-pyrazole

1) Methyl-5-(2-phenylethenyl)-1H-pyrazole

Under a nitrogen atmosphere, a mixture of 1-methyl-5-(4,4,5,5-tetramethyl-1,3,2-dioxaborolan-2-yl)-1H-pyrazole (1.50 g), β-bromostyrene (1.45 g), bis(triphenylphosphine) palladium(II) dichloride (506 mg), potassium carbonate (1.30 g), ethanol (3.8 mL) and dimethylformamide (7.5 mL) was stirred at 75° C. for 6 hours. Thereafter, 13-bromostyrene (1.45 g) was further added to the reaction solution, and the obtained solution was then stirred at 75° C. for 4 hours. Subsequently, the reaction solution was diluted with ethyl acetate, and was then washed with water. The organic layer was dried over anhydrous magnesium sulfate, and was then concentrated under a reduced pressure. The residue was purified by column chromatography (silica gel 60N, hexane:ethyl acetate=4:1 to 3:1), so as to obtain the title compound (990 mg) in the form of a light yellow solid.

1H NMR (600 MHz, CHLOROFORM-d) δ ppm 3.94 (s, 3H) 6.48 (d, J=1.83 Hz, 1H) 6.94 (d, J=16.05 Hz, 1H) 7.02 (d, J=16.05 Hz, 1H) 7.27-7.31 (m, 1H) 7.35-7.39 (m, 2H) 7.44 (d, J=1.83 Hz, 1H) 7.47-7.50 (m, 2H); MS (ESI pos.) m/z: 185 [M+H]$^+$ 2) 1-Methyl-5-(2-phenylethyl)-1H-pyrazole 10% Palladium carbon (30 mg) was added to an ethanol (3.0 mL) solution of 1-methyl-5-(2-phenylethenyl)-1H-pyrazole (300 mg), and the obtained solution was then stirred under a hydrogen atmosphere at a room temperature for 14 hours. Thereafter, the reaction solution was filtrated with Celite, and the filtrate was then concentrated under a reduced pressure, so as to obtain the title compound (310 mg) in the form of a colorless oily substance.

1H NMR (600 MHz, CHLOROFORM-d) δ ppm 2.86-2.96 (m, 4H) 3.66 (s, 3H) 6.04 (d, J=1.83 Hz, 1H) 7.16 (d, J=7.34 Hz, 2H) 7.20-7.24 (m, 1H) 7.27-7.31 (m, 2H) 7.38 (d, J=1.83 Hz, 1H); MS (ESI pos.) m/z: 187 [M+H]$^+$ The following compound was synthesized in the same manner as above.
1-Methyl-5-(3-phenylpropyl)-1H-pyrazole
MS (ESI pos.) m/z: 201 [M+H]$^+$ Production Example 9

5-Iodo-1-methyl-1H-pyrazole

Under a nitrogen atmosphere, n-butyllithium (39.0 mL, 2.6 M hexane solution) was added dropwise to a tetrahydrofuran (120 mL) solution of methylpyrazole (6.00 g) at −78° C., and the obtained solution was then stirred for 30 minutes. Thereafter, the reaction solution was stirred under cooling in an ice bath for 1 hour. Thereafter, the temperature of the reaction solution was cooled to −78° C., and a tetrahydrofuran (50 mL) solution of iodine (28.0 g) was then added dropwise to the reaction solution. Then, the reaction solution was stirred for 1 hour. Thereafter, the reaction solution was stirred overnight, while increasing the temperature of the solution to a room temperature. Subsequently, a 30% sodium thiosulfate aqueous solution was added to the reaction solution, and the solvent was then distilled away under a reduced pressure. The residue was extracted with ethyl acetate, and the organic layer was then washed with a saturated saline. The organic layer was dried over anhydrous sodium sulfate, and was then concentrated under a reduced pressure. The obtained solid was washed with n-hexane, so as to obtain the title compound (11.4 g) in the form of a brownish-red solid.

$^1$H NMR (200 MHz, CHLOROFORM-d) δ ppm 3.94 (s, 3H) 6.43 (d, J=2.20 Hz, 1H) 7.47 (d, J=1.76 Hz, 1H); MS (ESI pos.) m/z 209 [M+H]$^+$ Production Example 10

1-Methyl-5-{2-[4-(trifluoromethyl)phenyl]ethyl}-1H-pyrazole 1) 1-Methyl-5-{[4-(trifluoromethyl)phenyl]ethynyl}-1H-pyrazole A mixture of 5-iodo-1-methyl-1H-pyrazole (8.00 g), 1-ethynyl-4-(trifluoromethyl)benzene (6.54 g), copper(I)

iodide (110 mg), bis(triphenylphosphine)palladium(II) dichloride (1.35 g), triphenylphosphine (504 mg), triethylamine (8.00 mL) and dimethylformamide (70 mL) was stirred at 75° C. for 2 hours. Thereafter, the reaction solution was added to water, and the obtained mixture was then extracted with ethyl acetate. The organic layer was successively washed with water and a saturated saline, and was then dried over anhydrous magnesium sulfate, followed by vacuum concentration. The residue was purified by column chromatography (silica gel cartridge, hexane:ethyl acetate=85:15 to 75:25), so as to obtain the title compound (7.74 g) in the form of a yellow solid.

$^1$H NMR (200 MHz, CHLOROFORM-d) δ ppm 4.01 (s, 3H) 6.53 (d, J=2.20 Hz, 1H) 7.49 (d, J=2.20 Hz, 1H) 7.64 (s, 4H); MS (ESI pos.) m/z 251 [M+H]$^+$

2) 1-Methyl-5-{2-[4-(trifluoromethyl)phenyl]ethyl}-1H-pyrazole

10% Palladium carbon (1.00 g) was added to a methanol (150 mL) solution of 1-methyl-5-{[4-(trifluoromethyl)phenyl]ethynyl}-1H-pyrazole (2.33 g), and the obtained solution was then stirred under a hydrogen atmosphere at a room temperature overnight. Thereafter, the reaction solution was filtrated with Celite, and the filtrate was then concentrated under a reduced pressure, so as to obtain the title compound (1.90 g) in the form of a colorless oily substance.

$^1$H NMR (200 MHz, CHLOROFORM-d) δ ppm 2.84-3.09 (m, 4H) 3.69 (s, 3H) 6.03 (d, J=1.76 Hz, 1H) 7.27 (d, J=8.79 Hz, 2H) 7.39 (d, J=1.76 Hz, 1H) 7.56 (d, J=7.91 Hz, 2H); MS (ESI pos.) m/z 255 [M+H]$^+$ The following compounds were synthesized in the same manner as above.
2-[2-(1-methyl-1H-pyrazol-5-yl)ethyl]-5-(trifluoromethyl) pyridine
  MS (ESI pos.) m/z: 256 [M+H]$^+$
5-[2-(1-methyl-1H-pyrazol-5-yl)ethyl]-2-(trifluoromethyl) pyridine
  MS (ESI pos.) m/z: 256 [M+H]$^+$
1-methyl-5-{2-[2-(trifluoromethyl)phenyl]ethyl}-1H-pyrazole
  MS (ESI pos.) m/z: 255 [M+H]$^+$
1-methyl-5-{2-[3-(trifluoromethyl)phenyl]ethyl}-1H-pyrazole
  MS (ESI pos.) m/z: 255 [M+H]$^+$
3-fluoro-2-[2-(1-methyl-1H-pyrazol-5-yl)ethyl]-5-(trifluoromethyl)pyridine
  MS (ESI pos.) m/z: 274 [M+H]$^+$
5-[2-(4-fluorophenyl)ethyl]-1-methyl-1H-pyrazole
  MS (ESI pos.) m/z: 205 [M+H]$^+$
5-[2-(3,4-difluorophenyl)ethyl]-1-methyl-1H-pyrazole
  MS (ESI pos.) m/z: 223 [M+H]$^+$
5-(2-cyclohexylethyl)-1-methyl-1H-pyrazole
  MS (ESI pos.) m/z: 193 [M+H]$^+$

Production Example 11

2-(1-Methyl-1H-pyrazol-5-yl)-5-(trifluoromethyl)-2,3-dihydro-1H-isoindole

1-Methyl-1H-pyrazol-5-amine (1.53 g) and triethylamine (4.60 mL) were added to a 1,4-dioxane (53 mL) solution of 1,2-bis(bromomethyl)-4-(trifluoromethyl)benzene (5.25 g) at a room temperature, and the obtained solution was then stirred at 100° C. for 1 hour. Thereafter, the reaction solution was diluted with ethyl acetate, and was then washed with water and a saturated saline. The resultant was dried over anhydrous sodium sulfate, and was then concentrated under a reduced pressure. The residue was purified by column chromatography (silica gel 60N, hexane:ethyl acetate=2:1 to 40:60), so as to obtain the title compound (785 mg) in the form of a colorless solid.

1H NMR (600 MHz, CHLOROFORM-d) δ ppm 3.85 (s, 3H) 4.59 (s, 4H) 5.80 (d, J=1.83 Hz, 1H) 7.36-7.41 (m, 2H) 7.52-7.58 (m, 2H); MS (ESI pos.) m/z: 268 [M+H]$^+$ The following compounds were synthesized in the same manner as above.
2-(1-methyl-1H-pyrazol-5-yl)-2,3-dihydro-1H-isoindole
  MS (ESI pos.) m/z: 200 [M+H]$^+$
2-(1-methyl-1H-pyrazol-5-yl)-2,3-dihydro-1H-benzo[f]isoindole
  MS (ESI pos.) m/z: 250 [M+H]$^+$
5-chloro-2-(1-methyl-1H-pyrazol-5-yl)-2,3-dihydro-1H-isoindole
  MS (ESI pos.) m/z: 234 [M+H]$^+$
2-(1,3-dimethyl-1H-pyrazol-5-yl)-5-(trifluoromethyl)-2,3-dihydro-1H-isoindole
  MS (ESI pos.) m/z: 282 [M+H]$^+$

Production Example 12

2-(1-Methyl-1H-pyrazol-5-yl)-1H-benzo[f]isoindol-1,3(2H)-dione

Triethylamine (1.10 mL) was added to a toluene (14 mL) suspension that contained 1-methyl-1H-pyrazol-5-amine (400 mg) and 2,3-naphthalenedicarboxylic anhydride (816 mg), and the obtained solution was then heated to reflux for 2 hours. Thereafter, the reaction solution was cooled to a room temperature, and the precipitated solid was then collected by filtration. The collected solid was washed with ethyl acetate, so as to obtain the title compound (1.00 g) in the form of a colorless solid.

$^1$H NMR (200 MHz, DMSO-d$_6$) δ ppm 3.79 (s, 3H) 6.30 (d, J=2.20 Hz, 1H) 7.38 (d, J=1.76 Hz, 1H) 7.63-7.75 (m, 2H) 8.04-8.18 (m, 2H) 8.26 (s, 1H) 8.49 (s, 1H); MS (ESI pos.) m/z 278 [M+H]$^+$

Production Example 13

N-benzyl-1-methyl-1H-pyrazol-5-amine

Benzyl bromide (4.97 g) was added dropwise to a dimethylformamide (15 mL) mixture of 1-methyl-1H-pyrazol-5-amine (2.69 g) and potassium carbonate (4.02 g) at a room temperature, and the obtained solution was then stirred at 70° C. for 3 hours. Thereafter, water was added to the reaction solution, and the obtained mixture was then extracted with ethyl acetate. The organic layer was washed with a saturated saline, and was then dried over anhydrous magnesium sulfate, followed by vacuum concentration. The residue was purified by column chromatography (Chromatorex NH, hexane:ethyl acetate=2:1), so as to obtain the title compound (1.54 g) in the form of a light yellow oily substance.

1H NMR (600 MHz, CHLOROFORM-d) δ ppm 3.52 (br. s, 1H) 3.64 (s, 3H) 4.25 (d, J=5.96 Hz, 2H) 5.48 (d, J=1.83 Hz, 1H) 7.22-7.41 (m, 6H); MS (ESI pos.) m/z: 188 [M+H]$^+$ The following compound was synthesized in the same manner as above.
1-Methyl-N-[4-(trifluoromethyl)benzyl]-1H-pyrazol-5-amine
  MS (ESI pos.) m/z: 256 [M+H]+

Production Example 14

N,1-dimethyl-N-[4-(trifluoromethyl)benzyl]-1H-pyrazol-5-amine

1) N-(1-Methyl-1H-pyrazol-5-yl)-4-(trifluoromethyl)benzamide

Under cooling in an ice bath, 4-(trifluoromethyl)benzoyl chloride (8.26 g) was added dropwise to a chloroform (35 mL) solution that contained 1-methyl-1H-pyrazol-5-amine (3.50 g) and triethylamine (5.50 mL), and the obtained solution was then stirred for 2 hours. Thereafter, the reaction solution was diluted with chloroform, and was then washed with a saturated sodium hydrogencarbonate aqueous solution and a saturated saline. The organic layer was dried over anhydrous sodium sulfate, and was then concentrated under a reduced pressure. The obtained solid was washed with diisopropyl ether, so as to obtain the title compound (6.75 g) in the form of a colorless solid.

1H NMR (600 MHz, DMSO-$d_6$) δ ppm 3.68 (s, 3H) 6.24 (d, J=1.38 Hz, 1H) 7.38 (d, J=1.83 Hz, 1H) 7.91 (d, J=8.25 Hz, 2H) 8.14 (d, J=8.25 Hz, 2H) 10.53 (s, 1H); MS (ESI neg.) m/z: 268 [M−H]−

2) N-methyl-N-(1-methyl-1H-pyrazol-5-yl)-4-(trifluoromethyl)benzamide

Under cooling in an ice bath, 60% sodium hydride (39 mg) was added to a dimethylformamide (2.1 mL) solution of N-(1-methyl-1H-pyrazol-5-yl)-4-(trifluoromethyl)benzamide (200 mg), and the obtained solution was then stirred for 20 minutes. Thereafter, methyl iodide (51 μL) was added to the reaction solution, and the obtained solution was then stirred for 1.5 hours, and then at a room temperature for 17 hours. Thereafter, water was added to the reaction solution, and the obtained mixture was then extracted with ethyl acetate. The organic layer was washed with water and a saturated saline, and was then dried over anhydrous magnesium sulfate, followed by vacuum concentration. The residue was purified by column chromatography (NH silica gel cartridge, hexane:ethyl acetate=70:30 to 50:50), so as to obtain the title compound (141 mg) in the form of a colorless oily substance.

$^1$H NMR (200 MHz, CHLOROFORM-d) δ ppm 3.41 (s, 3H) 3.60 (s, 3H) 6.01 (d, J=1.76 Hz, 1H) 7.36 (d, J=1.76 Hz, 1H) 7.43 (d, J=8.79 Hz, 2H) 7.52 (d, J=8.35 Hz, 2H)

3) N,1-dimethyl-N-[4-(trifluoromethyl)benzyl]-1H-pyrazol-5-amine

Under cooling in an ice bath, lithium aluminum hydride (56 mg) was added to a tetrahydrofuran (3.2 mL) solution of N-methyl-N-(1-methyl-1H-pyrazol-5-yl)-4-(trifluoromethyl)benzamide (138 mg), and the obtained solution was then heated to reflux at 75° C. for 2.5 hours. Thereafter, a 1 M sodium hydroxide aqueous solution was added to the reaction solution under cooling in an ice bath, and the obtained solution was then stirred at a room temperature for 1.5 hours. Thereafter, the reaction suspension was filtrated with Celite, and the filtrate was then concentrated under a reduced pressure. The residue was diluted with ethyl acetate. The resultant was washed with a saturated saline, and was then dried over anhydrous magnesium sulfate, followed by vacuum concentration. The residue was purified by column chromatography (NH silica gel cartridge, hexane:ethyl acetate=70:30 to 50:50), so as to obtain the title compound (42 mg) in the form of a colorless oily substance.

$^1$H NMR (200 MHz, CHLOROFORM-d) δ ppm 2.61 (s, 3H) 3.76 (s, 3H) 4.06 (s, 2H) 5.84 (d, J=2.20 Hz, 1H) 7.37 (d, J=1.76 Hz, 1H) 7.43 (d, J=7.91 Hz, 2H) 7.60 (d, J=8.35 Hz, 2H); MS (ESI pos.) m/z: 270 [M+H]+

Production Example 15

1-Methyl-N-[4-(trifluoromethyl)phenyl]-1H-pyrazol-5-carboxamide

A mixture of 1-methyl-1H-pyrazol-5-carboxylic acid (1.00 g), 1-ethyl-3-(3-dimethylaminopropyl)carbodiimide hydrochloride (1.82 g), 1-hydroxybenzotriazole monohydrate (1.70 g) and chloroform (20 mL) was stirred at a room temperature for 15 minutes. Thereafter, 4-aminobenzotrifluoride (1.27 g) was added to the reaction solution, and the obtained mixture was then stirred for 24 hours. Thereafter, the reaction solution was concentrated under a reduced pressure, and the residue was then purified by column chromatography (chromatorex NH, hexane:ethyl acetate=4:1), so as to obtain the title compound (1.00 g) in the form of a colorless solid.

1H NMR (600 MHz, CHLOROFORM-d) δ ppm 4.21 (s, 3H) 6.67 (d, J=1.83 Hz, 1H) 7.51 (d, J=1.83 Hz, 1H) 7.62 (d, J=8.25 Hz, 2H) 7.71 (d, J=8.25 Hz, 2H) 7.80 (br. s., 1H); MS (ESI neg.) m/z: 268 [M−H]−

Production Example 16

N-[(1-methyl-1H-pyrazol-5-yl)methyl]-4-(trifluoromethyl)aniline

Acetic acid (0.87 mL) was added to a chloroform (10 mL) solution that contained 1-methyl-1H-pyrazol-5-carbaldehyde (1.00 g) and 4-aminobenzotrifluoride (1.76 g) at a room temperature, and the obtained solution was then stirred for 10 minutes. Thereafter, sodium triacetoxyborohydride (2.89 g) was added to the reaction solution, and the obtained mixture was then stirred for 5.5 hours. Thereafter, a saturated sodium hydrogencarbonate aqueous solution was added to the reaction solution, and the obtained mixture was then extracted with chloroform. The organic layer was dried over anhydrous sodium sulfate, and was then concentrated under a reduced pressure. The obtained solid was washed with diisopropyl ether, so as to obtain the title compound (1.88 g) in the form of a light yellow solid.

1H NMR (600 MHz, CHLOROFORM-d) δ ppm 3.87 (s, 3H) 4.08-4.17 (m, 1H) 4.35 (s, 2H) 6.21 (d, J=1.83 Hz, 1H) 6.67 (d, J=8.71 Hz, 2H) 7.42 (d, J=1.83 Hz, 1H) 7.44 (d, J=8.71 Hz, 2H); MS (ESI pos.) m/z: 256 [M+H]+

The following compound was synthesized in the same manner as above.
N-Methyl-N-[(1-methyl-1H-pyrazol-5-yl)methyl]-4-(trifluoromethyl)aniline
MS (ESI pos.) m/z: 270 [M+H]+

Production Example 17

2-Methyl-1'-[4-(trifluoromethyl)phenyl]-1'H,2H-3,4'-bipyrazole

1) 2-Methyl-1'H,2H-3,4'-bipyrazole

Under a nitrogen atmosphere, a mixture of 5-iodo-1-methyl-1H-pyrazole (750 mg), [1-(tert-butoxycarbonyl)-1H-pyrazol-4-yl]boronic acid (1.27 g), tetrakis(triphenylphosphine)palladium(0) (209 mg), 2 M sodium carbonate aqueous solution (3.6 mL), ethanol (3.6 mL) and toluene (7.2 mL) was stirred at 100° C. for 14 hours. Thereafter, water was added to the reaction solution, and the obtained mixture was then extracted with ethyl acetate. The organic layer was dried over anhydrous magnesium sulfate, and was then concentrated under a reduced pressure. The residue was purified by column chromatography (silica gel cartridge, hexane:ethyl acetate=4:1 to 0:10), so as to obtain the title compound (176 mg) in the form of a light yellow solid.

1H NMR (600 MHz, CHLOROFORM-d) δ ppm 3.96 (s, 3H) 6.33 (d, J=1.83 Hz, 1H) 7.51 (d, J=1.83 Hz, 1H) 7.78 (s, 2H) 10.33 (br. s., 1H); MS (ESI pos.) m/z: 149 [M+H]+

2) 2-Methyl-1'-[4-(trifluoromethyl)phenyl]-1'H,2H-3,4'-bipyrazole

Under a nitrogen atmosphere, a mixture of 2-methyl-1'H,2H-3,4'-bipyrazole (176 mg), 4-iodobenzotrifluoride (485 mg), copper iodide (45 mg), potassium carbonate (329 mg), trans-N,N'-dimethylcyclohexan-1,2-diamine (135 mg) and N,N-dimethylformamide (2.2 mL) was stirred at 100° C. for 16 hours. Thereafter, a saturated ammonium chloride aqueous solution was added to the reaction solution, and the obtained mixture was then extracted with chloroform. The organic layer was dried over anhydrous magnesium sulfate, and was then concentrated under a reduced pressure. The residue was purified by column chromatography (silica gel cartridge, hexane:ethyl acetate=9:1 to 1:1), so as to obtain the title compound (280 mg) in the form of a colorless solid.

1H NMR (600 MHz, CHLOROFORM-d) δ ppm 3.98 (s, 3H) 6.36 (d, J=1.83 Hz, 1H) 7.51 (d, J=1.83 Hz, 1H) 7.75 (d, J=8.25 Hz, 2H) 7.87 (d, J=8.25 Hz, 2H) 7.89 (s, 1H) 8.10 (s, 1H); MS (ESI pos.) m/z: 293 [M+H]+

The following compounds were synthesized in the same manner as above.
1'-(4-Methoxyphenyl)-2-methyl-1'H,2H-3,4'-bipyrazole
   MS (ESI pos.) m/z: 255 [M+H]+
1'-(4-Chlorophenyl)-2-methyl-1'H,2H-3,4'-bipyrazole
   MS (ESI pos.) m/z: 259 [M+H]++

Production Example 18

1'-(4-Fluorophenyl)-2-methyl-1'H,2H-3,4'-bipyrazole

Under a nitrogen atmosphere, a mixture of 5-iodo-1-methyl-1H-pyrazole (600 mg), [1-(4-fluorophenyl)-1H-pyrazol-4-yl]boronic acid (650 mg), tetrakistriphenylphosphine palladium (166 mg), 2 M sodium carbonate aqueous solution (2.9 mL), ethanol (3.0 mL) and toluene (6.0 mL) was stirred at 100° C. for 4 hours. Thereafter, water was added to the reaction solution, and the obtained mixture was then extracted with ethyl acetate. The organic layer was concentrated under a reduced pressure, and the residue was then purified by column chromatography (silica gel cartridge, hexane:ethyl acetate=9:1 to ethyl acetate), so as to obtain the title compound (450 mg) in the form of a light yellow solid.

1H NMR (600 MHz, CHLOROFORM-d) δ ppm 3.97 (s, 3H) 6.34 (d, J=1.83 Hz, 1H) 7.14-7.22 (m, 2H) 7.46-7.53 (m, 1H) 7.66-7.72 (m, 2H) 7.83 (s, 1H) 7.98 (s, 1H); MS (ESI pos.) m/z: 243 [M+H]+

Production Example 19

2-(1-Methyl-1H-pyrazol-5-yl)-5-[4-(trifluoromethyl)phenyl]-1,3,4-oxadiazole 1) 1-Methyl-N'-[4-(trifluoromethyl)benzoyl]-1H-pyrazol-5-carbohydrazide 4-(Trifluoromethyl)benzohydrazide (583 mg) was added to a dimethylformamide (6.8 mL) solution that contained 1-methyl-1H-pyrazol-5-carboxylic acid (300 mg), O-(7-azabenzotriazol-1-yl)-N,N,N',N'-tetramethyluronium hexafluorophosphate (1.09 g) and diisopropylethylamine (830 μL) at a room temperature, and the obtained solution was then stirred for 19 hours. Thereafter, water was added to the reaction solution, and the obtained mixture was then extracted with ethyl acetate. The organic layer was washed with water and a saturated saline, and was then dried over anhydrous magnesium sulfate, followed by vacuum concentration. The obtained solid was washed with ethyl acetate/hexane (1:1), so as to obtain the title compound (598 mg) in the form of a colorless solid. The filtrate was concentrated under a reduced pressure, and the residue was then purified by column chromatography (silica gel cartridge, chloroform:methanol=10:0 to 9:1), so as to further obtain the title compound (109 mg) in the form of a colorless solid.

1H NMR (600 MHz, DMSO-d6) δ ppm 4.05 (s, 3H) 6.98 (d, J=1.83 Hz, 1H) 7.51 (d, J=2.29 Hz, 1H) 7.90 (d, J=8.25 Hz, 2H) 8.08 (d, J=8.25 Hz, 2H) 10.56 (br. s., 1H) 10.75 (br. s., 1H); MS (ESI pos.) m/z 313 [M+H]+

2) 2-(1-Methyl-1H-pyrazol-5-yl)-5-[4-(trifluoromethyl)phenyl]-1,3,4-oxadiazole

Phosphorus oxychloride (1.80 mL) was added to an acetonitrile (4.8 mL) suspension of 1-methyl-N'-[4-(trifluoromethyl)benzoyl]-1H-pyrazol-5-carbohydrazide (300 mg) at a room temperature, and the obtained solution was then heated to reflux at 90° C. for 15 hours. Thereafter, the reaction solution was concentrated under a reduced pressure. A saturated sodium carbonate aqueous solution was added to the residue to convert it to a basic solution, and the resulting solution was then extracted with ethyl acetate. The organic layer was washed with a saturated saline, and was then dried over anhydrous magnesium sulfate, followed by vacuum concentration, so as to obtain the title compound (230 mg) in the form of a brown solid.

1H NMR (600 MHz, CHLOROFORM-d) δ ppm 4.37 (s, 3H) 6.96 (d, J=2.29 Hz, 1H) 7.61 (d, J=1.83 Hz, 1H) 7.81 (d, J=8.25 Hz, 2H) 8.25 (d, J=8.25 Hz, 2H); MS (ESI pos.) m/z 295 [M+H]+

Production Example 20

5-(1-Methyl-1H-pyrazol-5-yl)-3-[4-(trifluoromethyl)phenyl]-1,2,4-oxadiazole

N'-hydroxy-4-(trifluoromethyl)benzene carboximidamide (450 mg) was added to a tetrahydrofuran (8.8 mL) suspension that contained 1-methyl-1H-pyrazol-5-carboxylic acid (450 mg), 1-ethyl-3-(3-dimethylaminopropyl)carbodiimide hydrochloride (465 mg) and 1-hydroxybenzotriazole monohydrate (328 mg) at a room temperature, and the obtained solution was then stirred for 16 hours. Thereafter, potassium tert-butoxide (1.11 g) and tetrahydrofuran (4.4 mL) were added to the reaction solution, and the obtained mixture was then stirred at a room temperature for 3 hours. Thereafter, water was added to the reaction solution, and the obtained mixture was then extracted with ethyl acetate. The organic layer was washed with a saturated saline, and was then dried over anhydrous magnesium sulfate, followed by vacuum concentration. The residue was purified by column chromatography (silica gel cartridge, hexane:ethyl acetate=75:25 to 50:50), so as to obtain the title compound (193 mg) in the form of a colorless solid.

1H NMR (600 MHz, CHLOROFORM-d) δ ppm 4.43 (s, 3H) 7.15 (d, J=2.29 Hz, 1H) 7.65 (d, J=2.29 Hz, 1H) 7.82 (d, J=7.79 Hz, 2H) 8.32 (d, J=7.79 Hz, 2H); MS (ESI pos.) m/z 295 [M+H]+

Production Example 21

3-(1-Methyl-1H-pyrazol-5-yl)-5-[4-(trifluoromethyl)phenyl]-1,2-oxazole

1) N-methoxy-N,1-dimethyl-1H-pyrazol-5-carboxamide

N,O-dimethylhydroxylamine hydrochloride (1.30 g) was added to an dimethylformamide (32 mL) solution that contained 1-methyl-1H-pyrazol-5-carboxylic acid (1.21 g), O-(7-azabenzotriazol-1-yl)-N,N,N',N'-tetramethyluronium hexafluorophosphate (4.38 g) and diisopropylethylamine (3.34 mL) at a room temperature, and the obtained solution was then stirred for 2 hours. Thereafter, water was added to the reaction solution, and the obtained mixture was then extracted with ethyl acetate. The organic layer was washed with water and a saturated saline, and was then dried over anhydrous magnesium sulfate, followed by vacuum concentration. The residue was purified by column chromatography (silica gel cartridge, chloroform:methanol=100:0 to 95:5), so as to obtain the title compound (1.03 g) in the form of a yellow oily substance.

1H NMR (200 MHz, CHLOROFORM-d) δ ppm 3.36 (s, 3H) 3.66 (s, 3H) 4.13 (s, 3H) 6.77 (d, J=2.20 Hz, 1H) 7.48 (d, J=2.20 Hz, 1H); MS (ESI pos.) m/z: 170 [M+H]+

2) 1-(1-Methyl-1H-pyrazol-5-yl)-3-[4-(trifluoromethyl)phenyl]prop-2-yn-1-one

Methyl magnesium bromide (9.70 mL, 1.0 M tetrahydrofuran solution) was added dropwise to a tetrahydrofuran (4.0 mL) solution of 1-ethynyl-4-(trifluoromethyl)benzene (1.80 mL) under cooling in an ice bath, and the obtained solution was then stirred for 2 hours. Thereafter, the reaction solution was cooled to −78° C., and a tetrahydrofuran (6.2 mL) solution of N-methoxy-N,1-dimethyl-1H-pyrazol-5-carboxamide (867 mg) was then added thereto. The obtained mixture was stirred for 1 hour, and was then stirred for 2.5 hours under cooling in an ice bath. Thereafter, a saturated ammonium chloride aqueous solution was added to the reaction solution, and the obtained mixture was then extracted with ethyl acetate. The organic layer was washed with a saturated saline, and was then dried over anhydrous magnesium sulfate, followed by vacuum concentration. The residue was purified by column chromatography (silica gel cartridge, hexane:ethyl acetate=9:1), so as to obtain the title compound (1.09 g) in the form of a yellow oily substance.

1H NMR (600 MHz, CHLOROFORM-d) δ ppm 4.27 (s, 3H) 7.18 (d, J=1.83 Hz, 1H) 7.58 (d, J=1.83 Hz, 1H) 7.74 (d, J=8.25 Hz, 2H) 7.81 (d, J=7.79 Hz, 2H); MS (ESI pos.) m/z: 279 [M+H]+

3) N-hydroxy-1-(1-methyl-1H-pyrazol-5-yl)-3-[4-(trifluoromethyl)phenyl]prop-2-yn-1-imine An aqueous solution (3.0 mL) of hydroxylamine hydrochloride (338 mg) and an aqueous solution (4.0 mL) of sodium carbonate (515 mg) were added to a methanol (40 mL) solution of 1-(1-methyl-1H-pyrazol-5-yl)-3-[4-(trifluoromethyl)phenyl]prop-2-yn-1-one (338 mg) at a room temperature, and the obtained solution was then stirred overnight. Thereafter, the reaction solution was concentrated under a reduced pressure, and water was then added to the residue, followed by extraction with chloroform. The organic layer was washed with a saturated saline, and was then dried over anhydrous magnesium sulfate, followed by vacuum concentration. The residue was purified by column chromatography (silica gel cartridge, hexane:ethyl acetate=10:0 to 5:5), so as to obtain the title compound (312 mg) in the form of a yellow oily substance.

1H NMR (600 MHz, CHLOROFORM-d) δ ppm 3.94 (s, 3H) 4.25 (s, 1H) 6.44 (d, J=2.29 Hz, 1H) 7.38 (d, J=1.83 Hz, 1H) 7.69 (d, J=8.25 Hz, 2H) 7.80 (d, J=8.25 Hz, 2H); MS (ESI pos.) m/z: 294 [M+H]+

4) 3-(1-Methyl-1H-pyrazol-5-yl)-5-[4-(trifluoromethyl)phenyl]-1,2-oxazole

Concentrated hydrochloric acid (0.50 mL) was added to an acetic acid (5.0 mL) solution of N-hydroxy-1-(1-methyl-1H-pyrazol-5-yl)-3-[4-(trifluoromethyl)phenyl]prop-2-yn-1-imine (303 mg) at a room temperature, and the obtained solution was then heated to reflux for 30 minutes. Thereafter, water was added to the reaction solution, and the obtained solution was then neutralized with potassium carbonate, followed by extraction with chloroform. The organic layer was washed with a saturated saline, and was then dried over anhydrous magnesium sulfate, followed by vacuum concentration. The residue was purified by column chromatography (silica gel cartridge, hexane:ethyl acetate=3:2), so as to obtain the title compound (229 mg) in the form of a colorless solid.

1H NMR (600 MHz, CHLOROFORM-d) δ ppm 4.19 (s, 3H) 6.73 (d, J=1.83 Hz, 1H) 6.79 (s, 1H) 7.55 (d, J=1.83 Hz, 1H) 7.76 (d, J=8.25 Hz, 2H) 7.98 (d, J=8.25 Hz, 2H); MS (ESI pos.) m/z: 294 [M+H]+

Production Example 22

4-Iodo-1-methyl-5-[4-(trifluoromethyl)phenyl]-1H-pyrazole

An acetic acid (3.3 mL) solution of iodine monochloride (2.64 g) was added dropwise to an acetic acid (22 mL) solution that contained 1-methyl-5-[4-(trifluoromethyl)phenyl]-1H-pyrazole (3.70 g) and sodium acetate (1.38 g) at a room temperature, and the obtained solution was then stirred for 4 hours. Thereafter, water (250 mL) was added to the reaction solution, and the obtained solution was then stirred for 30 minutes. Then, a precipitated solid was collected by filtration, and was then washed with water. The obtained solid was dissolved in ethyl acetate, and the obtained solution was then washed with water and a saturated sodium hydrogencarbonate aqueous solution. The organic layer was dried over anhydrous sodium sulfate, and was then concentrated under a reduced pressure. Thereafter, the residue was purified by column chromatography (silica gel 60N, hexane:ethyl acetate=5:1 to 7:3), so as to obtain the title compound (4.80 g) in the form of a brownish-red oily substance.

1H NMR (600 MHz, CHLOROFORM-d) δ ppm 3.84 (s, 3H) 7.52 (d, J=8.25 Hz, 2H) 7.59 (s, 1H) 7.77 (d, J=7.79 Hz, 2H); MS (ESI pos.) m/z: 353 [M+H]+

The following compounds were synthesized in the same manner as above.

5-(biphenyl-4-yl)-4-iodo-1-methyl-1H-pyrazole
MS (ESI pos.) m/z: 361 [M+H]$^+$ 4-iodo-1-methyl-5-(naphthalen-2-yl)-1H-pyrazole
MS (ESI pos.) m/z: 335 [M+H]$^+$ 4-iodo-1-methyl-5-phenyl-1H-pyrazole
MS (ESI pos.) m/z: 285 [M+H]$^+$ 4-iodo-1-methyl-5-[3-(trifluoromethyl)phenyl]-1H-pyrazole
MS (ESI pos.) m/z: 353 [M+H]$^+$ 4-iodo-1-methyl-5-[2-(trifluoromethyl)phenyl]-1H-pyrazole
MS (ESI pos.) m/z: 353 [M+H]$^+$ 4-iodo-1-methyl-5-[4-(trifluoromethoxy)phenyl]-1H-pyrazole
MS (ESI pos.) m/z: 369 [M+H]$^+$ N-benzyl-4-iodo-1-methyl-1H-pyrazol-5-amine
MS (ESI pos.) m/z: 314 [M+H]$^+$ N-(4-iodo-1-methyl-1H-pyrazol-5-yl)-4-(trifluoromethyl)benzamide
MS (ESI pos.) m/z: 396 [M+H]$^+$ 4-iodo-1-methyl-N-[4-(trifluoromethyl)phenyl]-1H-pyrazol-5-carboxamide
MS (ESI pos.) m/z: 396 [M+H]$^+$ Production Example 23

4-Iodo-1-methyl-5-{2-[4-(trifluoromethyl)phenyl]ethyl}-1H-pyrazole

N-iodosuccinimide (1.91 g) was added to a trifluoroacetic acid (15 mL) solution of 1-methyl-5-{2-[4-(trifluoromethyl)phenyl]ethyl}-1H-pyrazole (1.96 g) at a room temperature, and the obtained solution was then stirred for 1 hour. Thereafter, the reaction solution was concentrated under a reduced pressure, and the residue was then diluted with chloroform. The resultant was washed with a saturated sodium hydrogencarbonate aqueous solution/a 30% sodium thiosulfate aqueous solution (1:1). The organic layer was washed with a saturated saline, and was then dried over anhydrous magnesium sulfate, followed by vacuum concentration. The residue was purified by column chromatography (silica gel cartridge, hexane:ethyl acetate=70:30 to 50:50), so as to obtain the title compound (2.98 g) in the form of a colorless oily substance.
1H NMR (600 MHz, CHLOROFORM-d) δ ppm 3.57 (s, 3H) 7.19 (d, J=8.25 Hz, 4H) 7.43 (s, 1H) 7.53 (d, J=7.79 Hz, 4H); MS (ESI pos.) m/z 381 [M+H]+

The following compounds were synthesized in the same manner as above.

4-iodo-1-methyl-5-[4-(2,2,2-trifluoroethoxy)phenyl]-1H-pyrazole
MS (ESI pos.) m/z: 383 [M+H]$^+$ 5-(4-iodo-1-methyl-1H-pyrazol-5-yl)-2-(trifluoromethyl)pyridine
MS (ESI pos.) m/z: 354 [M+H]$^+$ 2-(4-iodo-1-methyl-1H-pyrazol-5-yl)-5-(trifluoromethyl)pyridine
MS (ESI pos.) m/z: 354 [M+H]$^+$ 2-(4-iodo-1-methyl-1H-pyrazol-5-yl)-5-phenylpyridine
MS (ESI pos.) m/z: 362 [M+H]$^+$ 2-(4-iodo-1-methyl-1H-pyrazol-5-yl)quinoline
MS (ESI pos.) m/z: 335 [M+H]$^+$ 5-(4-iodo-1-methyl-1H-pyrazol-5-yl)-2-phenylpyridine
MS (ESI pos.) m/z: 362 [M+H]$^+$ 3-[4-(4-iodo-1-methyl-1H-pyrazol-5-yl)phenyl]pyridine
MS (ESI pos.) m/z: 362 [M+H]$^+$ 5-(4-cyclopentylphenyl)-4-iodo-1-methyl-1H-pyrazole
MS (ESI pos.) m/z: 353 [M+H]$^+$ 4-Iodo-1-methyl-5-(2-phenyl ethyl)-1H-pyrazole
MS (ESI pos.) m/z: 313 [M+H]+

4-Iodo-1-methyl-5-(3-phenylpropyl)-1H-pyrazole
MS (ESI pos.) m/z: 327 [M+H]+

4-iodo-1-methyl-5-{2-[4-(trifluoromethyl)phenyl]ethyl}-1H-pyrazole
MS (ESI pos.) m/z: 381 [M+H]$^+$ 2-[2-(4-Iodo-1-methyl-1H-pyrazol-5-yl)ethyl]-5-(trifluoromethyl)pyridine
MS (ESI pos.) m/z: 382 [M+H]+

5-[2-(4-Iodo-1-methyl-1H-pyrazol-5-yl)ethyl]-2-(trifluoromethyl)pyridine
MS (ESI pos.) m/z: 382 [M+H]+

4-Iodo-1-methyl-5-{2-[2-(trifluoromethyl)phenyl]ethyl}-1H-pyrazole
MS (ESI pos.) m/z: 381 [M+H]+

4-Iodo-1-methyl-5-{2-[3-(trifluoromethyl)phenyl]ethyl}-1H-pyrazole
MS (ESI pos.) m/z: 381 [M+H]+

2-(4-Iodo-1-methyl-1H-pyrazol-5-yl)-2,3-dihydro-1H-isoindole
MS (ESI pos.) m/z: 326 [M+H]+

1-(4-Iodo-1-methyl-1H-pyrazol-5-yl)-2,3-dihydro-1H-benzo[f]isoindole
MS (ESI pos.) m/z: 376 [M+H]+

2-(4-Iodo-1-methyl-1H-pyrazol-5-yl)-5-(trifluoromethyl)-2,3-dihydro-1H-isoindole
MS (ESI pos.) m/z: 394 [M+H]+

5-Chloro-2-(4-iodo-1-methyl-1H-pyrazol-5-yl)-2,3-dihydro-1H-isoindole
MS (ESI pos.) m/z: 360 [M+H]+

2-(4-Iodo-1,3-dimethyl-1H-pyrazol-5-yl)-5-(trifluoromethyl)-2,3-dihydro-1H-isoindole
MS (ESI pos.) m/z: 408 [M+H]+

2-(4-Iodo-1-methyl-1H-pyrazol-5-yl)-1H-benzo[f]isoindole-1,3(2H)-dione
MS (ESI pos.) m/z: 404 [M+H]+

4-Iodo-1-methyl-N-[4-(trifluoromethyl)benzyl]-1H-pyrazole-5-amine
MS (ESI pos.) m/z: 382 [M+H]+

N-[(4-Iodo-1-methyl-1H-pyrazol-5-yl)methyl]-4-(trifluoromethyl)aniline
MS (ESI pos.) m/z: 382 [M+H]+

N-[(4-Iodo-1-methyl-1H-pyrazol-5-yl)methyl]-N-methyl-4-(trifluoromethyl)aniline
MS (ESI pos.) m/z: 396 [M+H]+

4-Iodo-2-methyl-1'-[4-(trifluoromethyl)phenyl]-1'H,2H-3,4'-bipyrazole
MS (ESI pos.) m/z: 419 [M+H]+

1'-(4-Fluorophenyl)-4-iodo-2-methyl-1'H,2H-3,4'-bipyrazole
MS (ESI pos.) m/z: 369 [M+H]+

5-(4-Iodo-1-methyl-1H-pyrazol-5-yl)-3-[4-(trifluoromethyl)phenyl]-1,2-oxazole
MS ESI pos.) m/z: 420 [M+H]+

2-(4-Iodo-1-methyl-1H-pyrazol-5-yl)-5-[4-(trifluoromethyl)phenyl]-1,3,4-oxadiazole
MS (ESI pos.) m/z: 421 [M+H]+

5-(4-Iodo-1-methyl-1H-pyrazol-5-yl)-3-[4-(trifluoromethyl)phenyl]-1,2,4-oxadiazole
MS (ESI pos.) m/z: 421 [M+H]+

4-Iodo-1,3-dimethyl-1H-pyrazole-5-carbaldehyde
MS (ESI pos.) m/z: 251 [M+H]+

4-Iodo-1-methyl-1H-pyrazole-5-carbaldehyde
MS (ESI pos.) m/z: 237 [M+H]+

4-Iodo-N,1-dimethyl-N-[4-(trifluoromethyl)benzyl]-1H-pyrazole-5-amine

1H NMR (600 MHz, CHLOROFORM-d) δ ppm 2.80 (s, 3H) 3.67 (s, 3H) 4.31 (s, 2H) 7.37 (s, 1H) 7.43 (d, J=7.79 Hz, 2H) 7.57 (d, J=7.79 Hz, 2H)

3-Fluoro-2-[2-(4-iodo-1-methyl-1H-pyrazol-5-yl)ethyl]-5-(trifluoromethyl)pyridine
MS (ESI pos.) m/z: 400 [M+H]+

5-[2-(3,4-Difluorophenyl)ethyl]-4-iodo-1-methyl-1H-pyrazole
MS (ESI pos.) m/z: 349 [M+H]+

5-[2-(4-Fluorophenyl)ethyl]-4-iodo-1-methyl-1H-pyrazole
MS (ESI pos.) m/z: 331 [M+H]+

1'-(4-Chlorophenyl)-4-iodo-2-methyl-1'H,2H-3,4'-bipyrazole
MS (ESI pos.) m/z: 385 [M+H]+

4-Iodo-1'-(4-methoxyphenyl)-2-methyl-1'H,2H-3,4'-bipyrazole
MS (ESI pos.) m/z: 381 [M+H]+

5-(2-cyclohexylethyl)-4-iodo-1-methyl-1H-pyrazole
MS (ESI pos.) m/z: 319 [M+H]$^+$ 4-Iodo-1-methyl-5-{2-[4-(trifluoromethyl)phenoxy]ethyl}-1H-pyrazole
MS (ESI pos.) m/z: 397 [M+H]+

5-fluoro-2-[(4-iodo-1-methyl-1H-pyrazol-5-yl)methoxy]pyridine
MS (ESI pos.) m/z: 334 [M+H]$^+$ 2-[(4-iodo-1-methyl-1H-pyrazol-5-yl)methoxy]-5-(trifluoromethyl)pyridine
MS (ESI pos.) m/z: 384 [M+H]$^+$ Production Example 24

4-Ethynyl-1-methyl-5-[4-(trifluoromethyl)phenyl]-1H-pyrazole 1) 1-Methyl-5-[4-(trifluoromethyl)phenyl]-4-[(trimethylsilyl)ethynyl]-1H-pyrazole Under a nitrogen atmosphere, copper(I) iodide (7 mg), bis(triphenylphosphine)palladium(II) dichloride (90 mg) and triphenylphosphine (34 mg) were added to a dimethylformamide (45 mL) solution that contained 4-iodo-1-methyl-5-[4-(trifluoromethyl)phenyl]-1H-pyrazole (4.51 g), trimethylsilylacetylene (2.26 g) and triethylamine (3.57 mL), and the obtained solution was then stirred at 75° C. for 4 hours. Thereafter, the reaction solution was diluted with ethyl acetate, and was then washed with water and a saturated saline. The organic layer was dried over anhydrous sodium sulfate, and was then concentrated under a reduced pressure. The residue was purified by column chromatography (silica gel 60N, hexane:ethyl acetate=85:15 to 70:30), so as to obtain the title compound (3.46 g).
$^1$H NMR (600 MHz, CHLOROFORM-d) δ ppm 0.16 (s, 9H) 3.88 (s, 3H) 7.64-7.69 (m, 3H) 7.74 (d, J=7.79 Hz, 2H); MS (ESI pos.) m/z: 323 [M+H]$^+$ 2) 4-Ethynyl-1-methyl-5-[4-(trifluoromethyl)phenyl]-1H-pyrazole Under cooling in an ice bath, potassium carbonate (148 mg) was added to a tetrahydrofuran (16 mL) and methanol (36 mL) solution of 1-methyl-5-[4-(trifluoromethyl)phenyl]-4-[(trimethylsilyl)ethynyl]-1H-pyrazole (3.45 g), and the obtained solution was then stirred for 4.5 hours. Thereafter, the reaction solution was filtrated with Celite, and the filtrate was then concentrated under a reduced pressure. The residue was diluted with ethyl acetate, and was then washed with a saturated ammonium chloride aqueous solution. The organic layer was dried over anhydrous sodium sulfate, and was then concentrated under a reduced pressure. The residue was purified by column chromatography (silica gel 60N, hexane:ethyl acetate=85:15 to 60:40), so as to obtain the title compound (2.31 g).
$^1$H NMR (600 MHz, CHLOROFORM-d) δ ppm 2.97 (s, 1H) 3.86 (s, 3H) 7.64 (d, J=7.79 Hz, 2H) 7.69 (s, 1H) 7.76 (d, J=8.25 Hz, 2H); MS (ESI pos.) m/z: 251 [M+H]$^+$ The following compound was synthesized in the same manner as above.
5-(Biphenyl-4-yl)-4-ethynyl-1-methyl-1H-pyrazole
MS (ESI pos.) m/z: 259 [M+H]+

Production Example 25

5-[(4-Chlorobenzyl)oxy]-1-methyl-1H-pyrazol-4-carbaldehyde

Under cooling in an ice bath, potassium tert-butoxide (217 mg) was added to a tetrahydrofuran (2.8 mL) solution of 4-chlorobenzyl alcohol (217 mg), and the obtained solution was then stirred for 20 minutes. Under cooling in an ice bath, 5-chloro-1-methyl-1H-pyrazol-4-carbaldehyde (200 mg) was added to the reaction solution, and the obtained solution was then stirred for 3 hours. Thereafter, water was added to the reaction solution, and the obtained mixture was then extracted with ethyl acetate. The organic layer was washed with a saturated saline, and was then dried over anhydrous magnesium sulfate, followed by vacuum concentration. The residue was purified by column chromatography (silica gel cartridge, hexane:ethyl acetate=80:20 to 60:40), so as to obtain the title compound (127 mg) in the form of a colorless oily substance.
$^1$H NMR (200 MHz, CHLOROFORM-d) δ ppm 3.58 (s, 3H) 5.58 (s, 2H) 7.33-7.35 (m, 4H) 7.78 (s, 1H) 9.69 (s, 1H)
The following compounds were synthesized in the same manner as above.
1-Methyl-5-{[4-(trifluoromethyl)benzyl]oxy}-1H-pyrazole-4-carbaldehyde
MS (ESI pos.) m/z: 285 [M+H]+

Production Example 26

1-Methyl-5-(4-phenylpiperazin-1-yl)-1H-pyrazol-4-carbaldehyde

A mixture of 1-phenylpiperazine (3.40 g), 5-[(4-chlorobenzyl)oxy]-1-methyl-1H-pyrazol-4-carbaldehyde (600 mg), triethylamine (1.20 mL) and dimethylformamide (7.0 mL) was stirred at 120° C. for 8 hours, and then at a room temperature for 17 hours. Thereafter, the reaction solution was concentrated under a reduced pressure, and water was then added thereto. The obtained mixture was extracted with ethyl acetate. The organic layer was washed with water and a saturated saline, and was then dried over anhydrous sodium sulfate, followed by vacuum concentration. The residue was purified by column chromatography (silica gel cartridge, hexane:ethyl acetate=80:20 to 10:90), so as to obtain the title compound (669 mg) in the form of a light yellow solid.
1H NMR (200 MHz, CHLOROFORM-d) δ ppm 3.24-3.45 (m, 8H) 3.80 (s, 3H) 6.86-7.02 (m, 3H) 7.24-7.36 (m, 2H) 7.88 (s, 1H) 9.89 (s, 1H); MS (ESI pos.) m/z: 271 [M+H]$^+$ Production Example 27

5-[(4-Chlorobenzyl)oxy]-4-ethynyl-1-methyl-1H-pyrazole

A mixture of 5-[(4-chlorobenzyl)oxy]-1-methyl-1H-pyrazol-4-carbaldehyde (125 mg), potassium carbonate (173 mg), dimethyl (1-diazo-2-oxopropyl)phosphonate (192 mg) and methanol (2.5 mL) was stirred at a room temperature for 24 hours. Thereafter, a saturated sodium hydrogencarbonate aqueous solution was added to the reaction solution, and the obtained mixture was then extracted with ethyl acetate. The organic layer was washed with a saturated saline, and was then dried over anhydrous magnesium sulfate, followed by vacuum concentration. The residue was purified by column chromatography (silica gel cartridge, hexane:ethyl acetate=80:20 to 70:30), so as to obtain the title compound (76 mg) in the form of a light yellow oily substance.

$^1$H NMR (600 MHz, CHLOROFORM-d) δ ppm 3.14 (s, 1H) 3.53 (s, 3H) 5.50 (s, 2H) 7.35 (s, 4H) 7.41 (s, 1H)

The following compounds were synthesized in the same manner as above.

4-Ethynyl-1-methyl-5-{[4-(trifluoromethyl)benzyl]oxy}-1H-pyrazole

MS (ESI pos.) m/z: 281 [M+H]$^+$ 1-(4-Ethynyl-1-methyl-1H-pyrazol-5-yl)-4-phenylpiperazine MS (ESI pos.) m/z: 267 [M+H]$^+$ Production Example 28

4-[(5-Formyl-1-methyl-1H-pyrazol-4-yl)ethynyl]benzenesulfonamide

A mixture of 4-iodo-1-methyl-1H-pyrazol-5-carbaldehyde (500 mg), 4-ethynylbenzenesulfonic acid (383 mg), copper(I) iodide (20 mg), bis(triphenylphosphine)palladium (II) dichloride (149 mg), triethylamine (600 μL) and dimethylformamide (10 mL) was stirred at 80° C. for 4 hours. Thereafter, the reaction solution was filtrated with Celite, and the filtrate was then washed with water. The organic layer was dried over anhydrous sodium sulfate, and was then concentrated under a reduced pressure. The residue was purified by column chromatography (silica gel cartridge, chloroform/methanol=99:1 to 90:10), so as to obtain the title compound (580 mg) in the form of a light yellow solid.

$^1$H NMR (200 MHz, CHLOROFORM-d) δ ppm 4.20 (s, 3H) 4.84 (s, 2H) 7.60-7.71 (m, 3H) 7.93 (d, J=8.35 Hz, 2H) 10.09 (s, 1H)

The following compound was synthesized in the same manner as above.

3-[(5-Formyl-1-methyl-1H-pyrazol-4-yl)ethynyl]benzenesulfonamide $^1$H NMR (600 MHz, CHLOROFORM-d) δ ppm 4.18 (s, 3H) 5.01 (br. s., 2H) 7.39 (s, 1H) 7.49-7.55 (m, 1H) 7.64-7.73 (m, 2H) 8.07 (s, 1H) 10.07 (s, 1H); MS (ESI neg.) m/z: 288 [M–H]$^-$ Production Example 29

4-{[5-(Hydroxymethyl)-1-methyl-1H-pyrazol-4-yl]ethynyl}benzenesulfonamide

Under a nitrogen atmosphere, 1.0 M diisobutylaluminum hydride (1.70 mL, toluene solution) was added dropwise to a tetrahydrofuran (5.0 mL) solution of 4-[(5-formyl-1-methyl-1H-pyrazol-4-yl)ethynyl]benzenesulfonamide (160 mg) at −78° C., and the obtained solution was then stirred for 1 hour. Thereafter, water was added to the reaction solution, and the obtained solution was converted to an acidic solution by addition of 2 M hydrochloric acid. Then, the solution was extracted with ethyl acetate. The organic layer was washed with water, and was then dried over anhydrous sodium sulfate, followed by vacuum concentration. The residue was purified by column chromatography (silica gel cartridge, chloroform/methanol=99:1 to 95:5), so as to obtain the title compound (60 mg) in the form of a light yellow solid.

$^1$H NMR (600 MHz, DMSO-d$_6$) δ ppm 3.83 (s, 3H) 4.59 (d, J=5.50 Hz, 2H) 5.44 (t, J=5.50 Hz, 1H) 7.40 (s, 2H) 7.61-7.66 (m, 3H) 7.79 (d, J=7.79 Hz, 2H)

The following compound was synthesized in the same manner as above.

3-{[5-(Hydroxymethyl)-1-methyl-1H-pyrazol-4-yl]ethynyl}benzenesulfonamide

MS (ESI neg.) m/z: 290 [M–H]$^-$

Production Example 30

4-Iodo-1,3-dimethyl-5-{[4-(trifluoromethyl)phenoxy]methyl}-1H-pyrazole 1) (4-Iodo-1,3-dimethyl-1H-pyrazol-5-yl)methanol Sodium borohydride (45 mg) was added to a methanol (10 mL) solution of 4-iodo-1,3-dimethyl-1H-pyrazol-5-carbaldehyde (200 mg) at a room temperature, and the obtained solution was then stirred for 3 hour. Thereafter, a saturated ammonium chloride aqueous solution was added to the reaction solution, and the obtained mixture was then extracted with ethyl acetate. The organic layer was washed with water, and was then dried over anhydrous sodium sulfate, followed by vacuum concentration, so as to obtain the title compound (75 mg) in the form of a light yellow solid.

1H NMR (200 MHz, CHLOROFORM-d) δ ppm 2.23 (s, 3H) 3.93 (s, 3H) 4.67 (s, 2H)

2) 4-Iodo-1,3-dimethyl-5-{[4-(trifluoromethyl)phenoxy]methyl}-1H-pyrazole

A mixture of (4-iodo-1,3-dimethyl-1H-pyrazol-5-yl)methanol (75 mg), 4-hydroxybenzotrifluoride (48 mg), 40% diisopropyl azodicarboxylate (90 mg, toluene solution), triphenylphosphine (117 mg) and tetrahydrofuran (3.0 mL) was stirred at a room temperature overnight. Thereafter, water was added to the reaction solution, and the obtained mixture was then extracted with ethyl acetate. The organic layer was washed with water, and was then dried over anhydrous sodium sulfate, followed by vacuum concentration. The residue was purified by column chromatography (silica gel cartridge, hexane/ethyl acetate=90:10 to 50:50), so as to obtain the title compound (34 mg) in the form of a light yellow solid.

1H NMR (200 MHz, CHLOROFORM-d) δ ppm 2.22 (s, 3H) 2.92 (s, 3H) 3.52 (s, 2H) 7.22 (d, J=7.91 Hz, 2H) 7.54 (d, J=8.35 Hz, 2H); MS (ESI pos.) m/z: 397 [M+H]$^+$ The following compound was synthesized in the same manner as above.

4-Iodo-1-methyl-5-{[4-(trifluoromethyl)phenoxy]methyl}-1H-pyrazole

MS (ESI pos.) m/z: 383 [M+H]$^+$

Production Example 31

1-Methyl-5-{2-[4-(trifluoromethyl)phenoxy]ethyl}-1H-pyrazole

A mixture of 2-(1-methyl-1H-pyrazol-5-yl)ethanol (1.00 g), 4-hydroxybenzotrifluoride (2.57 g), 1.9 M diisopropyl azodicarboxylate (6.26 mL, toluene solution), triphenylphosphine (3.12 g) and tetrahydrofuran (50 mL) was stirred at a room temperature for 2 days. Thereafter, water was added to the reaction solution, and the obtained mixture was then extracted with ethyl acetate. The organic layer was washed with water, and was then dried over anhydrous sodium sulfate, followed by vacuum concentration. The residue was purified by column chromatography (silica gel cartridge, hexane/ethyl acetate=90:10 to 55:45), so as to obtain the title compound (1.17 g) in the form of a light yellow oily substance.

1H NMR (200 MHz, CHLOROFORM-d) δ ppm 3.14 (t, J=6.59 Hz, 2H) 3.88 (s, 3H) 4.24 (t, J=6.59 Hz, 2H) 6.12 (d, J=1.76 Hz, 1H) 6.89-7.01 (m, 2H) 7.42 (d, J=1.76 Hz, 1H) 7.55 (d, J=9.23 Hz, 2H); MS (ESI pos.) m/z: 271 [M+H]$^+$ Production Example 32

2-[(1-Methyl-1H-pyrazol-5-yl)methoxy]-5-(trifluoromethyl)pyridine

Under a nitrogen atmosphere, a mixture of (1-methyl-1H-pyrazol-5-yl)methanol (200 mg), 2-chloro-5-(trifluoromethyl)pyridine (389 mg), palladium(II) acetate (40 mg), cesium carbonate (870 mg), rac-2-(di-t-butylphosphino)-1,1'-binaphthyl (71 mg) and toluene (9.0 mL) was stirred at 100° C. for 2.5 hours. Thereafter, the reaction solution was diluted with diethyl ether, and was then filtrated with Celite. The filtrate was concentrated under a reduced pressure. The residue was purified by column chromatography (silica gel cartridge, hexane:ethyl acetate=85:15 to 50:50), so as to obtain the title compound (310 mg) in the form of a light yellow oily substance.

1H NMR (200 MHz, CHLOROFORM-d) δ ppm 3.95 (s, 3H) 5.44 (s, 2H) 6.36 (d, J=1.76 Hz, 1H) 6.85 (d, J=8.79 Hz, 1H) 7.45 (d, J=2.20 Hz, 1H) 7.80 (dd, J=8.79, 2.64 Hz, 1H) 8.47 (s, 1H); MS (ESI pos.) m/z: 258 [M+H]$^+$ Production Example 33

5-Fluoro-2-[(1-methyl-1H-pyrazol-5-yl)methoxy]pyridine

60% Sodium hydride (390 mg) was added to a dimethylformamide (9.0 mL) solution of (1-methyl-1H-pyrazol-5-yl)methanol (1.00 g) at a room temperature, and the obtained solution was then stirred for 2 hours. Thereafter, 2,5-difluoropyridine (1.17 g) was added to the reaction solution, and the mixed solution was then stirred for 16 hours. Subsequently, water was added to the reaction solution, and the obtained mixture was then extracted with hexane/ethyl acetate (1/2). The organic layer was concentrated under a reduced pressure. The residue was purified by column chromatography (silica gel cartridge, hexane/ethyl acetate=95:5 to 60:40), so as to obtain the title compound (1.08 g) in the form of a colorless solid.

1H NMR (600 MHz, CHLOROFORM-d) δ ppm 3.92 (s, 3H) 5.33 (s, 2H) 6.33 (d, J=1.83 Hz, 1H) 6.73 (dd, J=9.17, 3.67 Hz, 1H) 7.35 (ddd, J=8.94, 7.57, 3.21 Hz, 1H) 7.43 (d, J=1.83 Hz, 1H) 7.99 (d, J=3.21 Hz, 1H)

Example 1

N-[2-(dimethylamino)ethyl]-3-({1-methyl-5-[4-(trifluoromethyl)phenyl]-1H-pyrazol-4-yl}ethynyl)benzenesulfonamide

[Formula 33]

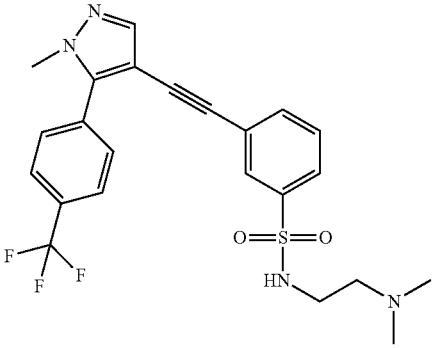 [SMILES: CN(C)CCN(C)S(=O)(=O)c1cccc(C#Cc2cnn(C)c2-c2ccc(C(F)(F)F)cc2)c1]

To a dimethylformamide (0.80 mL) solution that contained the 4-ethynyl-1-methyl-5-[4-(trifluoromethyl)phenyl]-1H-pyrazole (122 mg) obtained in Production Example 24 and the 3-bromo-N-[2-(dimethylamino)ethyl]benzenesulfonamide (100 mg) obtained in Production Example 1, triethylamine (91 µL), copper(I) iodide (4 mg), triphenylphosphine (4 mg) and bis(triphenylphosphine)palladium(II) dichloride (11 mg) were added, and the obtained solution was then stirred at 75° C. for 4 hours. Thereafter, the reaction solution was diluted with ethyl acetate, and was then washed with water. The organic layer was dried over anhydrous sodium sulfate, and was then concentrated under a reduced pressure. The residue was purified by column chromatography (Chromatorex NH, hexane:ethyl acetate=50:50 to 1:99) and (Chromatorex NH, chloroform:methanol=99:1), so as to obtain the title compound (97 mg) in the form of an amorphous substance.

1H NMR (600 MHz, CHLOROFORM-d) δ ppm 2.08 (s, 6H) 2.29-2.38 (m, 2H) 2.91-3.03 (m, 2H) 3.91 (s, 3H) 5.02-5.58 (m, 1H) 7.44 (t, J=7.70 Hz, 1H) 7.53 (dt, J=7.79, 1.38 Hz, 1H) 7.69 (d, J=8.25 Hz, 2H) 7.75 (s, 1H) 7.77 (dt, J=7.68, 1.20 Hz, 1H) 7.80 (d, J=7.79 Hz, 2H) 7.88 (t, J=1.60 Hz, 1H). MS (ESI pos.) m/z: 477 [M+H]$^+$ The compounds of Example 2 to Example 18, which are shown in Table 1-1 to Table 1-3 below, were obtained by the same method as that in Example 1.

TABLE 1-1

| Example | Structural formula | Instrumental data |
|---|---|---|
| 2 | (structure shown) | 1H NMR (600 MHz, CHLOROFORM-d) δ ppm 0.98 (s, 3H) 2.54 (t, J = 5.96 Hz, 2H) 3.59-3.70 (m, 4H) 3.91 (s, 3H) 5.40 (s, 1H) 7.44 (t, J = 7.80 Hz, 1H) 7.53 (dt, J = 7.79, 1.38 Hz, 1H) 7.69 (d, J = 8.25 Hz, 2H) 7.76 (s, 1H) 7.78-7.83 (m, 3H) 7.92 (t, J = 1.38 Hz, 1H); MS (ESI neg.) m/z: 492 [M − H]− |

TABLE 1-1-continued

| Example | Structural formula | Instrumental data |
|---|---|---|
| 3 | | 1H NMR (600 MHz, CHLOROFORM-d) δ ppm 3.91 (s, 3H) 4.77 (s, 2H) 7.47 (d, J = 8.71 Hz, 2H) 7.69 (d, J = 8.25 Hz, 2H) 7.76 (s, 1H) 7.80 (d, J = 8.25 Hz, 2H) 7.84 (d, J = 8.71 Hz, 2H); MS (ESI neg.) m/z: 404 [M − H]− |
| 4 | | 1H NMR (600 MHz, CHLOROFORM-d) δ ppm 2.24 (s, 6H) 2.48 (t, J = 6.88 Hz, 2H) 2.79 (s, 3H) 3.12 (t, J = 6.88 Hz, 2H) 3.91 (s, 3H) 7.42-7.46 (m, 1H) 7.53 (dt, J = 7.79, 1.38 Hz, 1H) 7.64-7.71 (m, 3H) 7.75 (s, 1H) 7.78-7.81 (m, 3H); MS (ESI pos.) m/z: 491 [M + H]+ |
| 5 | | 1H NMR (600 MHz, CHLOROFORM-d) δ ppm 1.57-1.63 (m, 2H) 2.18 (s, 6H) 2.32-2.36 (m, 2H) 3.05 (t, J = 6.00 Hz, 2H) 3.90 (s, 3H) 7.44 (t, J = 7.80 Hz, 1H) 7.52 (dt, J = 7.79, 1.38 Hz, 1H) 7.69 (d, J = 8.25 Hz, 2H) 7.73-7.77 (m, 2H) 7.80 (d, J = 7.79 Hz, 2H) 7.85 (t, J = 1.60 Hz, 1H); MS (ESI pos.) m/z: 491 [M + H]+ |
| 6 | | 1H NMR (600 MHz, CHLOROFORM-d) δ ppm 3.04 (s, 3H) 3.91 (s, 3H) 7.50 (t, J = 7.80 Hz, 1H) 7.61 (dt, J = 7.79, 1.38 Hz, 1H) 7.69 (d, J = 8.25 Hz, 2H) 7.75 (s, 1H) 7.81 (d, J = 7.79 Hz, 2H) 7.82-7.85 (m, 1H) 7.94 (t, J = 1.60 Hz, 1H); MS (ESI pos.) m/z: 405 [M + H]+ |

TABLE 1-1-continued

| Example | Structural formula | Instrumental data |
|---|---|---|
| 7 | | 1H NMR (600 MHz, CHLOROFORM-d) δ ppm 2.07 (s, 6H) 2.31-2.34 (m, 2H) 2.95-2.98 (m, 2H) 3.94 (s, 3H) 5.31 (br. S, 1H) 7.37-7.41 (m, 1H) 7.43 (t, J = 7.79 Hz, 1H) 7.46-7.50 (m, 2H) 7.55 (dt, J = 7.79, 1.38 Hz, 1H) 7.61-7.69 (m, 4H) 7.72-7.78 (m, 4H) 7.89 (t, J = 1.60 Hz, 1H); MS (ESI pos.) m/z: 485 [M + H]+ |

TABLE 1-2

| Example | Structural formula | Instrumental data |
|---|---|---|
| 8 | | 1H NMR (600 MHz, CHLOROFORM-d) δ ppm 2.09 (s, 6H) 2.33-2.36 (m, 2H) 2.94-2.99 (m, 2H) 3.91 (s, 3H) 5.31 (br. s, 1H) 7.47 (d, J = 8.25 Hz, 2H) 7.69 (d, J = 8.25 Hz, 2H) 7.76 (s, 1H) 7.78-7.82 (m, 4H); MS (ESI pos.) m/z: 477 [M + H]+ |
| 9 | | 1H NMR (600 MHz, CHLOROFORM-d) δ ppm 3.90 (s, 3H) 5.14 (br. s., 2H) 7.67 (d, J = 7.79 Hz, 2H) 7.71 (s, 1H) 7.78 (d, J = 8.25 Hz, 2H) 8.29-8.31 (m, 2H); MS (ESI pos.) m/z: 344 [M + H]+ |
| 10 | | 1H NMR (600 MHz, CHLOROFORM-d) δ ppm 3.90 (s, 3H) 4.61-4.69 (m, 2H) 6.45 (s, 1H) 6.59 (dd, J = 5.50, 1.38 Hz, 1H) 7.67 (d, J = 8.25 Hz, 2H) 7.74 (s, 1H) 7.80 (d, J = 8.25 Hz, 2H) 7.96 (d, J = 5.50 Hz, 1H); MS (ESI pos.) m/z: 343 [M + H]+ |

TABLE 1-2-continued
| 11 | 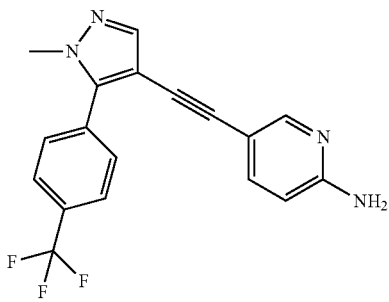 [SMILES: Cn1ncc(C#Cc2ccc(N)nc2)c1-c1ccc(C(F)(F)F)cc1] | 1H NMR (600 MHz, CHLOROFORM-d) δ ppm 3.90 (s, 3H) 4.70-4.76 (m, 2H) 6.44 (d, J = 8.25 Hz, 1H) 7.43 (dd, J = 8.71, 2.29 Hz, 1H) 7.69 (d, J = 8.25 Hz, 2H) 7.70 (s, 1H) 7.77 (d, J = 8.25 Hz, 2H) 8.10 (s, 1H); MS (ESI pos.) m/z: 343 [M + H]+ |
|---|---|---|
| 12 | 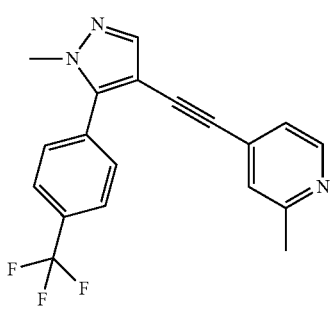 [SMILES: Cc1cc(C#Cc2cnn(C)c2-c2ccc(C(F)(F)F)cc2)ccn1] | 1H NMR (600 MHz, CHLOROFORM-d) δ ppm 2.55 (br. s., 3H) 3.94 (s, 3H) 7.03-7.08 (m, 1H) 7.09-7.15 (m, 1H) 7.71 (d, J = 7.79 Hz, 2H) 7.78 (s, 1H) 7.83 (d, J = 7.79 Hz, 2H) 8.42-8.49 (m, 1H); MS (ESI pos.) m/z: 342 [M + H]+ |
| 13 | 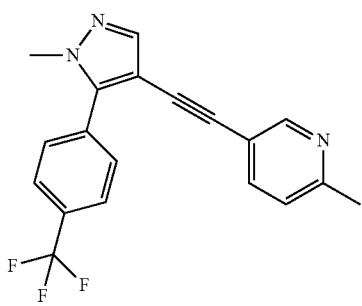 [SMILES: Cc1ccc(C#Cc2cnn(C)c2-c2ccc(C(F)(F)F)cc2)cn1] | 1H NMR (600 MHz, CHLOROFORM-d) δ ppm 2.58 (s, 3H) 3.94 (s, 3H) 7.12 (d, J = 7.79 Hz, 1H) 7.55-7.60 (m, 1H) 7.72 (d, J = 8.25 Hz, 2H) 7.77 (s, 1H) 7.81 (d, J = 8.25 Hz, 2H) 8.53 (d, J = 1.83 Hz, 1H); MS (ESI pos.) m/z: 342 [M + H]+ |
TABLE 1-3
| 14 | 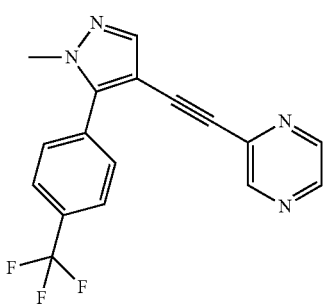 [SMILES: Cn1ncc(C#Cc2cnccn2)c1-c1ccc(C(F)(F)F)cc1] | 1H NMR (600 MHz, CHLOROFORM-d) d ppm 3.91 (s, 3H) 7.67-7.73 (m, 2H) 7.77-7.85 (m, 3H) 8.32-8.75 (m, 3H). MS: (ESI pos) m/z: 329 [M + H]+ |
|---|---|---|

TABLE 1-3-continued
| 15 | 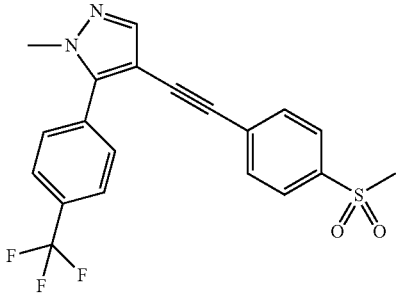 [SMILES: Cn1ncc(C#Cc2ccc(S(C)(=O)=O)cc2)c1-c1ccc(C(F)(F)F)cc1] | 1H NMR (600 MHz, CHLOROFORM-d) δ ppm 3.02 (s, 3H) 3.90 (s, 3H) 7.49-7.52 (m, 2H) 7.68 (d, J = 7.79 Hz, 2H) 7.75 (s, 1H) 7.79 (d, J = 7.79 Hz, 2H) 7.84-7.87 (m, 2H); MS (ESI pos.) m/z: 405 [M + H]+ |
|---|---|---|
| 16 | 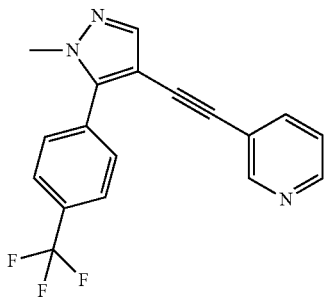 [SMILES: Cn1ncc(C#Cc2cccnc2)c1-c1ccc(C(F)(F)F)cc1] | 1H NMR (600 MHz, CHLOROFORM-d) δ ppm 3.91 (s, 3H) 7.22-7.28 (m, 1H) 7.66 (d, J = 7.79 Hz, 1H) 7.69 (d, J = 7.79 Hz, 2H) 7.75 (s, 1H) 7.79 (d, J = 8.25 Hz, 2H) 8.47-8.56 (m, 1H) 8.56-8.67 (m, 1H); MS (ESI pos.) m/z: 328 [M + H]+ |
| 17 | 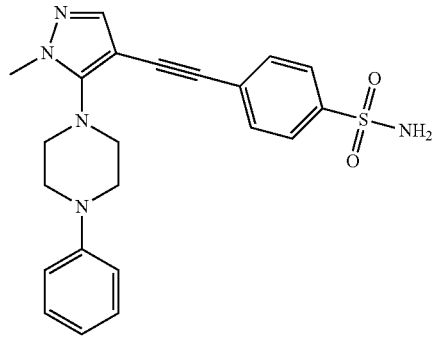 [SMILES: Cn1ncc(C#Cc2ccc(S(N)(=O)=O)cc2)c1N1CCN(c2ccccc2)CC1] | 1H NMR (600 MHz, DMSO-d6) δ ppm 3.32-3.38 (m, 8H) 3.70 (s, 3H) 6.80-6.84 (m, 1H) 6.99-7.03 (m, 2H) 7.24 (dd, J = 8.7, 7.3 Hz, 2H) 7.41 (br. s, 2H) 7.54-7.57 (m, 2H) 7.58 (s, 1H) 7.78-7.79 (m, 2H); MS (ESI pos.) m/z: 422 [M + H]+ |
| 18 | 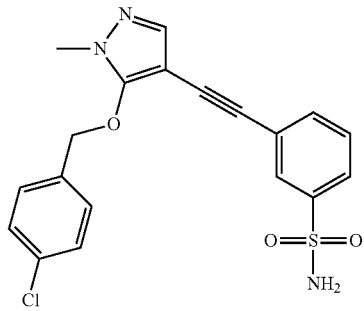 [SMILES: Cn1ncc(C#Cc2cccc(S(N)(=O)=O)c2)c1OCc1ccc(Cl)cc1] | 1H NMR (600 MHz, DMSO-d6) δ ppm 3.53 (s, 3H) 5.55 (s, 2H) 7.41 (s, 2H) 7.43-7.51 (m, 4H) 7.53 (s, 1H) 7.54-7.58 (m, 1H) 7.63 (dt, J = 7.79, 1.38 Hz, 1H) 7.75 (ddd, J = 7.79, 1.83, 0.92 Hz, 1H) 7.85 (t, J = 1.60 Hz, 1H); MS (ESI neg.) m/z: 400 [M − H]− |

Example 2

N-(1,3-dihydroxy-2-methylpropan-2-yl)-3-({1-methyl-5-[4-(trifluoromethyl)phenyl]-1H-pyrazol-4-yl}ethynyl)benzenesulfonamide

Example 3

4-({1-methyl-5-[4-(trifluoromethyl)phenyl]-1H-pyrazol-4-yl}ethynyl)benzenesulfonamide

Example 4

N-[2-(dimethylamino)ethyl]-N-methyl-3-({1-methyl-5-[4-(trifluoromethyl)phenyl]-1H-pyrazol-4-yl}ethynyl)benzenesulfonamide

Example 5

N-[3-(dimethylamino)propyl]-3-({1-methyl-5-[4-(trifluoromethyl)phenyl]-1H-pyrazol-4-yl}ethynyl)benzenesulfonamide

Example 6

1-methyl-4-{[3-(methylsulfonyl)phenyl]ethynyl}-5-[4-(trifluoromethyl)phenyl]-1H-pyrazole

Example 7

3-{[5-(biphenyl-4-yl)-1-methyl-1H-pyrazol-4-yl]ethynyl}-N-[2-(dimethylamino)ethyl]benzenesulfonamide

Example 8

N-[2-(dimethylamino)ethyl]-4-({1-methyl-5-[4-(trifluoromethyl)phenyl]-1H-pyrazol-4-yl}ethynyl)benzenesulfonamide

Example 9

5-({1-methyl-5-[4-(trifluoromethyl)phenyl]-1H-pyrazol-4-yl}ethynyl)pyrimidin-2-amine

Example 10

4-({1-methyl-5-[4-(trifluoromethyl)phenyl]-1H-pyrazol-4-yl}ethynyl)pyridin-2-amine

Example 11

5-({1-methyl-5-[4-(trifluoromethyl)phenyl]-1H-pyrazol-4-yl}ethynyl)pyridin-2-amine

Example 12

2-methyl-4-({1-methyl-5-[4-(trifluoromethyl)phenyl]-1H-pyrazol-4-yl}ethynyl)pyridine

Example 13

2-methyl-5-({1-methyl-5-[4-(trifluoromethyl)phenyl]-1H-pyrazol-4-yl}ethynyl)pyridine

Example 14

2-({1-methyl-5-[4-(trifluoromethyl)phenyl]-1H-pyrazol-4-yl}ethynyl)pyrazine

Example 15

1-methyl-4-{[4-(methylsulfonyl)phenyl]ethynyl}-5-[4-(trifluoromethyl)phenyl]-1H-pyrazole

Example 16

3-({1-methyl-5-[4-(trifluoromethyl)phenyl]-1H-pyrazol-4-yl}ethynyl)pyridine

Example 17

4-{[1-methyl-5-(4-phenylpiperazin-1-yl)-1H-pyrazol-4-yl]ethynyl}benzenesulfonamide

Example 18

3-({5-[(4-chlorobenzyl)oxy]-1-methyl-1H-pyrazol-4-yl}ethynyl)benzenesulfonamide

Example 19

N-[2-(dimethylamino)ethyl]-3-({1-methyl-5-[4-(trifluoromethyl)phenyl]-1H-pyrazol-4-yl}ethynyl)benzenesulfonamide hydrochloride

[Formula 34]

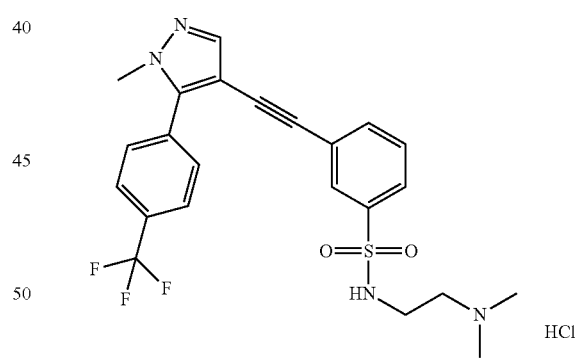

To an ethyl acetate (0.76 mL) solution of the N-[2-(dimethylamino)ethyl]-3-({1-methyl-5-[4-(trifluoromethyl)phenyl]-1H-pyrazol-4-yl}ethynyl)benzenesulfonamide (76 mg) obtained in Example 1, a 4 M HCl/ethyl acetate solution (48 μL) was added at a room temperature, and the obtained solution was then stirred for 3 hours. Thereafter, the generated solid was collected by filtration, and was then washed with ethyl acetate, so as to obtain the title compound (58 mg) in the form of a colorless solid.

1H NMR (600 MHz, METHANOL-$d_3$) δ ppm 2.88 (s, 6H) 3.12-3.16 (m, 2H) 3.18-3.23 (m, 2H) 3.89 (s, 3H) 7.56 (t, J=7.80 Hz, 1H) 7.61-7.64 (m, 1H) 7.76 (s, 1H) 7.78-7.81 (m, 1H) 7.82-7.85 (m, 3H) 7.88 (d, J=8.25 Hz, 2H). MS (ESI pos) m/z: 477 [M+H]+.

Example 20

3-{[5-(Biphenyl-4-yl)-1-methyl-1H-pyrazol-4-yl]ethynyl}-N-[2-(dimethylamino)ethyl]benzenesulfonamide hydrochloride

[Formula 35]

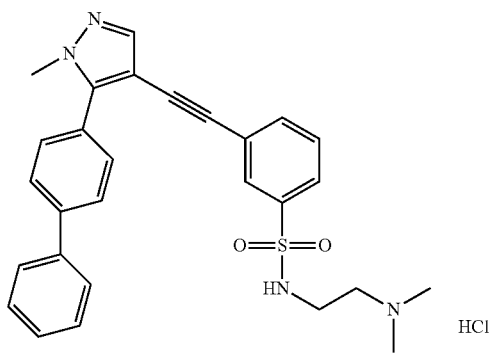

The title compound (71 mg) was obtained in the form of a light yellow solid from the 3-{[5-(biphenyl-4-yl)-1-methyl-1H-pyrazol-4-yl]ethynyl}-N-[2-(dimethylamino)ethyl]benzenesulfonamide (77 mg) obtained in Example 7 by the same method as that in Example 19.

1H NMR (600 MHz, METHANOL-d₃) δ ppm 2.87 (s, 6H) 3.13 (t, J=6.00 Hz, 2H) 3.20 (t, J=6.00 Hz, 2H) 3.92 (s, 3H) 7.38 (t, J=7.30 Hz, 1H) 7.47 (t, J=7.80 Hz, 2H) 7.56 (t, J=7.80 Hz, 1H) 7.63 (d, J=7.79 Hz, 1H) 7.69-7.73 (m, 4H) 7.75 (s, 1H) 7.77-7.80 (m, 1H) 7.84 (d, J=8.25 Hz, 3H). MS (ESI pos.) m/z: 485 [M+H]+.

Example 21

4-[(1-Methyl-5-{2-[4-(trifluoromethyl)phenyl]ethyl}-1H-pyrazol-4-yl)ethynyl]benzenesulfonamide

[Formula 36]

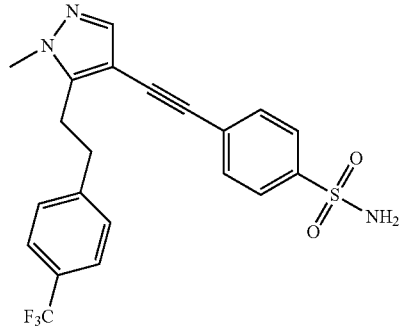

To a dimethylformamide (1.5 mL) solution that contained the 4-iodo-1-methyl-5-{2-[4-(trifluoromethyl)phenyl]ethyl}-1H-pyrazole (150 mg) obtained in Production Example 23 and the 4-ethynylbenzenesulfonamide (86 mg) obtained in Production Example 3, triethylamine (110 μL), copper(I) iodide (2 mg), triphenylphosphine (10 mg) and bis(triphenylphosphine)palladium(II) dichloride (28 mg) were added, and the obtained solution was then stirred at 75° C. for 2 hours. Thereafter, the reaction solution was diluted with ethyl acetate, and was then washed with water. The organic layer was dried over anhydrous sodium sulfate, and was then concentrated under a reduced pressure. The residue was purified by column chromatography (silica gel 60N, chloroform:methanol=98:2) and (Chromatorex NH, hexane:ethyl acetate=1:2), so as to obtain the title compound (70 mg) in the form of a colorless solid.

1H NMR (600 MHz, DMSO-d6) δ ppm 3.02 (t, J=7.30 Hz, 2H) 3.08-3.12 (m, 2H) 3.70 (s, 3H) 7.37-7.41 (m, 4H) 7.54-7.59 (m, 5H) 7.78 (dt, J=8.71, 1.83 Hz, 2H). MS (ESI neg.) m/z: 432 [M–H]⁻

The compounds of Example 22 to Example 97, which are shown in Table 2-1 and Table 2-13 below, were obtained by the same method as that in Example 21.

TABLE 2-1

| Example | Structural formula | Instrumental data |
|---|---|---|
| 22 | 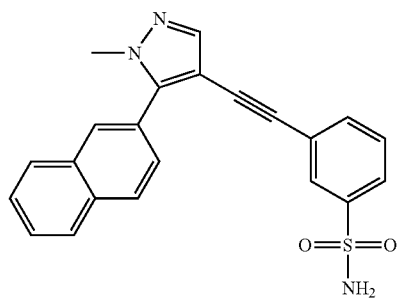 [SMILES: Cn1ncc(C#Cc2cccc(S(N)(=O)=O)c2)c1-c1ccc2ccccc2c1] | 1H NMR (600 MHz, CHLOROFORM-d) δ ppm 3.96 (s, 3H) 4.70 (s, 2H) 7.39 (t, J = 8.25 Hz, 1H) 7.48-7.68 (m, 4H) 7.74-7.79 (m, 2H) 7.86-7.96 (m, 3H) 8.00 (d, J = 8.71 Hz, 1H) 8.04 (s, 1H); MS (ESI pos.) m/z: 388 [M + H]+ |

TABLE 2-1-continued

| Example | Structural formula | Instrumental data |
|---|---|---|
| 23 | | 1H NMR (600 MHz, CHLOROFORM-d) δ ppm 3.94 (s, 3H) 4.78 (s, 2H) 7.37-7.51 (m, 4H) 7.56 (d, J = 7.80 Hz, 1H) 7.61-7.69 (m, 4H) 7.72-7.82 (m, 4H) 7.92-7.95 (m, 1H); MS (ESI neg.) m/z: 412 [M − H]− |
| 24 | | 1H NMR (600 MHz, CHLOROFORM-d) δ ppm 3.89 (s, 3H) 4.84 (s, 2H) 7.43 (t, J = 7.80 Hz, 1H) 7.46-7.57 (m, 6H) 7.72 (s, 1H) 7.77-7.80 (m, 1H) 7.90 (t, J = 1.60 Hz, 1H); MS (ESI pos.) m/z 338 [M + H]+ |
| 25 | | 1H NMR (600 MHz, CHLOROFORM-d) δ ppm 3.90 (s, 3H) 4.79 (s, 2H) 7.45 (t, J = 7.80 Hz, 1H) 7.54 (d, J = 7.79 Hz, 1H) 7.68 (d, J = 7.79 Hz, 2H) 7.75 (s, 1H) 7.78-7.84 (m, 3H) 7.91-7.94 (m, 1H); MS (ESI neg.) m/z 404 [M − H]− |
| 26 | | 1H NMR (600 MHz, CHLOROFORM-d) δ ppm 3.91 (s, 3H) 7.27-7.32 (m, 3H) 7.35-7.38 (m, 2H) 7.71 (d, J = 7.79 Hz, 2H) 7.73 (s, 1H) 7.78 (d, J = 8.25 Hz, 2H); MS (ESI pos.) m/z 327 [M + H]+ |
| 27 | | 1H NMR (600 MHz, DMSO-d6) δ ppm 3.56 (s, 3H) 4.71 (d, J = 6.42 Hz, 2H) 6.71 (t, J = 6.65 Hz, 1H) 7.17-7.21 (m, 1H) 7.27-7.31 (m, 3H) 7.32-7.39 (m, 5H) 7.48 (t, J = 7.79 Hz, 1H) 7.66 (d, J = 7.70 Hz, 1H) 7.68-7.71 (m, 1H); MS (ESI neg.) m/z 365 [M − H]− |

TABLE 2-2

| | | |
|---|---|---|
| 28 | *(structure)* | 1H NMR (600 MHz, DMSO-d6) δ ppm 3.77 (s, 3H) 4.90 (s, 4H) 7.25-7.37 (m, 4H) 7.38 (s, 2H) 7.47-7.53 (m, 2H) 7.54 (s, 1H) 7.71 (d, J = 7.50 Hz, 1H) 7.74-7.76 (m, 1H); MS (ESI neg.) m/z 377 [M − H]− |
| 29 | *(structure)* | 1H NMR (600 MHz, DMSO-d6) δ ppm 3.58 (s, 3H) 4.80 (d, J = 6.42 Hz, 2H) 6.84 (t, J = 6.65 Hz, 1H) 7.27 (d, J = 7.80 Hz, 1H) 7.30 (s, 1H) 7.37 (s, 2H) 7.45 (t, J = 7.79 Hz, 1H) 7.55 (d, J = 7.79 Hz, 2H) 7.64-7.69 (m, 4H); MS (ESI neg) m/z 433 [M − H]− |
| 30 | *(structure)* | 1H NMR (600 MHz, DMSO-d6) δ ppm 4.09 (s, 3H) 7.42 (s, 2H) 7.59 (t, J = 7.60 Hz, 1H) 7.70 (dt, J = 7.79, 1.38 Hz, 1H) 7.77-7.80 (m, 1H) 7.87 (t, J = 1.38 Hz, 1H) 7.92 (s, 1H) 8.26 (d, J = 8.25 Hz, 1H) 8.46 (dd, J = 8.25, 2.29 Hz, 1H) 9.15-9.17 (m, 1H); MS (ESI neg.) m/z 405 [M − H]− |
| 31 | *(structure)* | 1H NMR (600 MHz, CHLOROFORM-d) δ ppm 3.92 (s, 3H) 4.80 (s, 2H) 7.44 (t, J = 7.80 Hz, 1H) 7.53 (d, J = 7.80 Hz, 1H) 7.65-7.70 (m, 1H) 7.71-7.77 (m, 3H) 7.79-7.83 (m, 1H) 7.88-7.91 (m, 2H); MS (ESI neg.) m/z 404 [M − H]− |
| 32 | *(structure)* | 1H NMR (600 MHz, CHLOROFORM-d) δ ppm 3.61 (s, 3H) 4.72 (br. s., 2H) 7.36-7.43 (m, 2H) 7.44-7.47 (m, 1H) 7.63-7.73 (m, 3H) 7.74-7.79 (m, 2H) 7.87 (d, J = 7.34 Hz, 1H); MS (ESI neg.) m/z 404 [M − H]− |

TABLE 2-2-continued

| 33 | (structure: 1-methylpyrazole with 4-(trifluoromethoxy)phenyl at 5-position and alkyne linked to 3-sulfamoylphenyl at 4-position) | 1H NMR (600 MHz, CHLOROFORM-d) δ ppm 3.89 (s, 3H) 4.80 (br. s, 2H) 7.38 (d, J = 8.25 Hz, 2H) 7.45 (t, J = 7.80 Hz, 1H) 7.53 (dt, J = 7.79, 1.38 Hz, 1H) 7.57-7.60 (m, 2H) 7.72 (s, 1H) 7.80-7.82 (m, 1H) 7.92 (t, J = 1.60 Hz, 1H); MS (ESI pos.) m/z 422 [M + H]+ |

TABLE 2-3

| 34 | (structure: 1-methylpyrazole with 4-(trifluoromethoxy)phenyl at 5-position and alkyne linked to 4-sulfamoylphenyl at 4-position) | 1H NMR (600 MHz, CHLOROFORM-d) δ ppm 3.90 (s, 3H) 4.77 (br. s, 2H) 7.38 (dd, J = 8.71, 0.92 Hz, 2H) 7.46 (d, J = 8.71 Hz, 2H) 7.59 (d, J = 8.71 Hz, 2H) 7.74 (s, 1H) 7.84 (d, J = 8.71 Hz, 2H); MS (ESI neg.) m/z 420 [M − H]− |
| 35 | (structure: 1-methylpyrazole with 5-NH-C(O)-(4-trifluoromethylphenyl) and alkyne linked to 3-sulfamoylphenyl at 4-position) | 1H NMR (600 MHz, METHANOL-d3) δ ppm 3.77 (s, 3H) 7.48 (t, J = 7.80 Hz, 1H) 7.57 (d, J = 7.79 Hz, 1H) 7.69 (s, 1H) 7.77-7.82 (m, 1H) 7.86 (d, J = 8.25 Hz, 2H) 7.89-7.92 (m, 1H) 8.18 (d, J = 7.79 Hz, 2H); MS (ESI neg.) m/z 447 [M − H]− |
| 36 | (structure: 1-methylpyrazole with 2,3-dihydro-1H-benz[f]isoindol-2-yl at 5-position and alkyne linked to 4-sulfamoylphenyl at 4-position) | 1H NMR (600 MHz, CHLOROFORM-d) δ ppm 3.86 (s, 3H) 4.69 (br. s, 2H) 4.98 (s, 4H) 7.29 (d, J = 8.71 Hz, 2H) 7.48 (dd, J = 6.42, 3.21 Hz, 2H) 7.57 (s, 1H) 7.72 (d, J = 8.71 Hz, 2H) 7.74 (s, 2H) 7.83 (dd, J = 6.42, 3.21 Hz, 2H); MS (ESI neg.) m/z 427 [M − H]− |

TABLE 2-3-continued
| 37 | 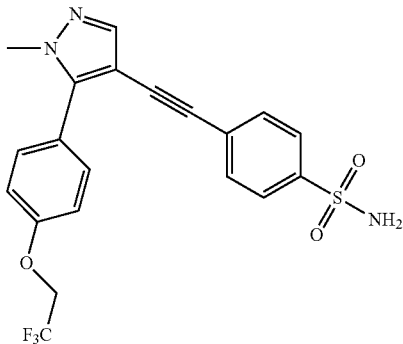 [SMILES: Cn1ncc(C#Cc2ccc(S(N)(=O)=O)cc2)c1-c1ccc(OCC(F)(F)F)cc1] | 1H NMR (600 MHz, DMSO-d6) δ ppm 3.82 (s, 3H) 4.85 (q, J = 9.02 Hz, 2H) 7.25 (d, J = 8.71 Hz, 2H) 7.39 (br. s, 2H) 7.51 (d, J = 8.25 Hz, 2H) 7.62-7.65 (m, 2H) 7.76 (d, J = 8.25 Hz, 2H) 7.79 (s, 1H); MS (ESI neg.) m/z 434 [M − H]− |
| --- | --- | --- |
| 38 | 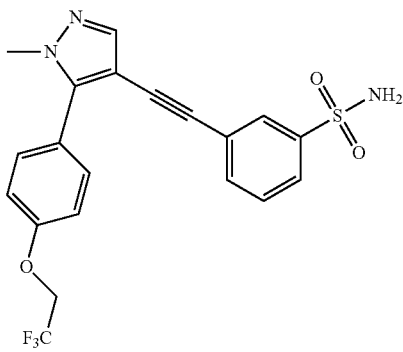 [SMILES: Cn1ncc(C#Cc2cccc(S(N)(=O)=O)c2)c1-c1ccc(OCC(F)(F)F)cc1] | 1H NMR (600 MHz, DMSO-d6) δ ppm 3.81 (s, 3H) 4.83 (q, J = 8.71 Hz, 2H) 7.20-7.25 (m, 2H) 7.39 (br. s, 2H) 7.50-7.56 (m, 2H) 7.60-7.64 (m, 2H) 7.70-7.75 (m, 2H) 7.79 (s, 1H); MS (ESI neg.) m/z 434 [M − H]− |
| 39 | 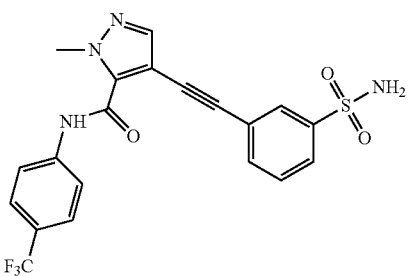 [SMILES: Cn1ncc(C#Cc2cccc(S(N)(=O)=O)c2)c1C(=O)Nc1ccc(C(F)(F)F)cc1] | 1H NMR (600 MHz, DMSO-d6) δ ppm 4.00 (s, 3H) 7.42 (br. s, 2H) 7.54-7.61 (m, 2H) 7.72 (d, J = 8.71 Hz, 2H) 7.78 (dt, J = 7.34, 1.60 Hz, 1H) 7.85-7.87 (m, 1H) 7.89 (s, 1H) 7.94 (d, J = 8.25 Hz, 2H) 10.90 (br. s, 1H); MS (ESI neg.) m/z 447 [M − H]− |
TABLE 2-4
| 40 | 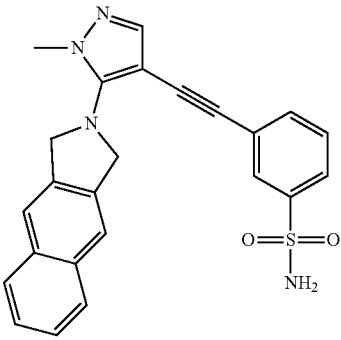 [SMILES: Cn1ncc(C#Cc2cccc(S(N)(=O)=O)c2)c1N1Cc2cc3ccccc3cc2C1] | 1H NMR (600 MHz, CHLOROFORM-d) δ ppm 3.85 (s, 3H) 4.50 (br. s, 2H) 4.98 (s, 4H) 7.33 (t, J = 7.30 Hz, 1 H) 7.38 (dt, J = 7.79, 1.40 Hz, 1H) 7.47 (dd, J = 6.42, 3.21 Hz, 2H) 7.56 (s, 1H) 7.70-7.74 (m, 2H) 7.77 (s, 2H) 7.85 (dd, J = 6.42, 3.21 Hz, 2H); MS (ESI pos.) m/z 429 [M + H]+ |
| --- | --- | --- |

TABLE 2-4-continued

| | | |
|---|---|---|
| 41 | [structure] | 1H NMR (600 MHz, DMSO-d6) δ ppm 2.89 (t, J = 7.30 Hz, 2H) 3.04 (t, J = 7.30 Hz, 2H) 3.59 (s, 3H) 7.13 (d, J = 7.34 Hz, 3H) 7.18-7.23 (m, 2H) 7.37 (br. s, 2H) 7.55 (s, 1H) 7.56-7.59 (m, 2H) 7.75-7.79 (m, 2H); MS (ESI neg.) m/z 364 [M − H]− |
| 42 | [structure] | 1H NMR (600 MHz, DMSO-d6) δ ppm 2.98 (t, J = 7.30 Hz, 2H) 3.12 (t, J = 7.80 Hz, 2H) 3.68 (s, 3H) 7.20-7.24 (m, 3H) 7.27-7.32 (m, 2H) 7.48 (br. s, 2H) 7.62-7.66 (m, 2H) 7.70 (d, J = 7.79 Hz, 1H) 7.82 (dt, J = 7.79, 1.38 Hz, 1H) 7.91 (t, J = 1.60 Hz, 1H); MS (ESI neg.) m/z 364 [M − H]− |
| 43 | [structure] | 1H NMR (600 MHz, CHLOROFORM-d) δ ppm 2.04 (s, 2H) 2.72 (t, J = 7.30 Hz, 2H) 2.79 (t, J = 7.80 Hz, 2H) 3.75 (s, 3H) 4.78 (br. s, 2H) 7.17-7.21 (m, 3H) 7.24-7.29 (m, 2H) 7.47 (t, J = 7.80 Hz, 1H) 7.56-7.59 (m, 2H) 7.83 (d, J = 8.25 Hz, 1H) 7.97 (t, J = 1.60 Hz, tH); MS (ESI pos.) m/z 380 [M + H]+ |
| 44 | [structure] | 1H NMR (600 MHz, CHLOROFORM-d) δ ppm 2.01-2.08 (m, 2H) 2.72 (t, J = 7.57 Hz, 2H) 2.79 (t, J = 7.30 Hz, 2H) 3.76 (s. 3H) 4.94 (br. s, 2H) 7.17-7.22 (m, 3 H) 7.24-7.29 (m, 2H) 7.47 (dt, J = 8.71, 1.83 Hz, 2H) 7.57 (s, 1H) 7.85 (dt, J = 8.71, 1.83 Hz, 2H); MS (ESI pos.) m/z 380 [M+H]+ |
| 45 | [structure] | 1H NMR (600 MHz. DMSO-d6) δ ppm 3.00-3.04 (m, 2 H) 3.08-3.12 (m, 2H) 3.69 (s, 3H) 7.39 (d, J = 7.79 Hz, 2H) 7.42 (br. s, 2H) 7.54-7.60 (m, 5H) 7.75 (dt, J = 7.68, 1.66 Hz, 1H) 7.84 (t, J = 1.60 Hz, 1H); MS (ESI neg.) m/z 432 [M − H]− |

TABLE 2-5

| # | Structure | Data |
|---|---|---|
| 46 | 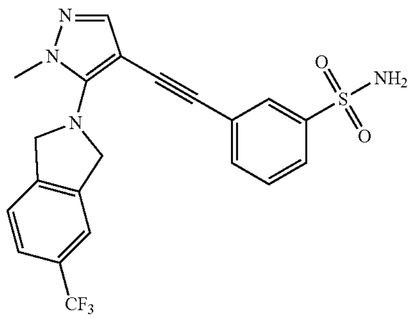 [SMILES: Cn1ncc(C#Cc2cccc(S(N)(=O)=O)c2)c1N1Cc2ccc(C(F)(F)F)cc2C1] | 1H NMR (600 MHz, DMSO-d6) δ ppm 3.77 (s, 3H) 4.95 (d, J = 9.63 Hz, 4H) 7.37 (s, 2H) 7.47-7.53 (m, 2H) 7.56 (s, 1H) 7.59 (d, J = 7.79 Hz, 1H) 7.65 (d, J = 8.25 Hz, 1H) 7.71 (dt, J = 7.57, 1.72 Hz, 1H) 7.74-7.77 (m, 2H); MS (ESI neg.) m/z 445 [M − H]− |
| 47 | 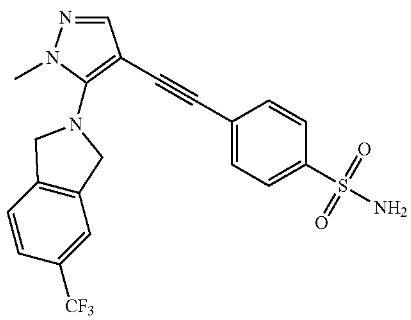 [SMILES: Cn1ncc(C#Cc2ccc(S(N)(=O)=O)cc2)c1N1Cc2ccc(C(F)(F)F)cc2C1] | 1H NMR (600 MHz, DMSO-d6) δ ppm 3.77 (s, 3H) 4.95 (s, 4H) 7.36 (br. s, 2H) 7.42-7.45 (m, 2H) 7.55 (s, 1H) 7.60 (d, J = 7.79 Hz, 1H) 7.66 (d, J = 7.79 Hz, 1H) 7.72 (d, J = 8.71 Hz, 2H) 7.78 (s, 1H); MS (ESI neg.) m/z 445 [M − H]− |
| 48 | 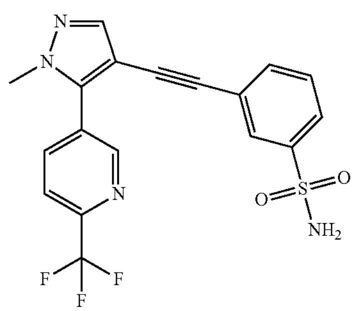 [SMILES: Cn1ncc(C#Cc2cccc(S(N)(=O)=O)c2)c1-c1ccc(C(F)(F)F)nc1] | 1H NMR (200 MHz, DMSO-d6) δ ppm 3.95 (s, 3H) 7.44 (br. s, 2H) 7.53-7.67 (m, 2H) 7.73-7.86 (m, 2H) 7.97 (s, 1H) 8.16 (d, J = 7.91 Hz, 1H) 8.45 (d, J = 7.47 Hz, 1H) 9.10 (s, 1H); MS (ESI pos.) m/z 407 [M + H]+ |
| 49 | 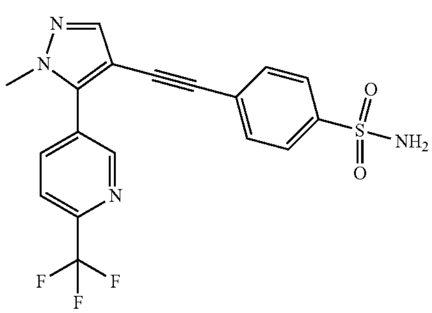 [SMILES: Cn1ncc(C#Cc2ccc(S(N)(=O)=O)cc2)c1-c1ccc(C(F)(F)F)nc1] | 1H NMR (200 MHz, DMSO-d6) δ ppm 3.95 (s, 3H) 7.44 (br. s, 2H) 7.59 (d, J = 8.79 Hz, 2H) 7.76-7.87 (m, 2H) 7.96 (s, 1H) 8.17 (d, J = 8.35 Hz, 1H) 8.39-8.50 (m, 1H) 9.10 (s, 1H); MS (ESI pos.) m/z 407 [M + H]+ |
| 50 | 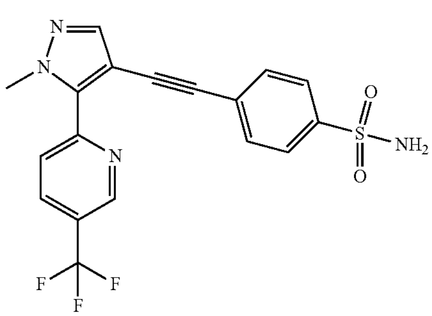 [SMILES: Cn1ncc(C#Cc2ccc(S(N)(=O)=O)cc2)c1-c1ccc(C(F)(F)F)cn1] | 1H NMR (200 MHz, DMSO-d6) δ ppm 4.13 (s, 3H) 7.45 (br. s, 2H) 7.70 (d, J = 8.79 Hz, 2H) 7.83 (d, J = 8.35 Hz, 2H) 7.95 (s, 1H) 8.30 (d, J = 7.91 Hz, 1H) 8.54 (d, J = 8.79 Hz, 1H) 9.20 (s, 1H); MS (ESI pos.) m/z 407 [M + H]+ |

TABLE 2-5-continued
| 51 | 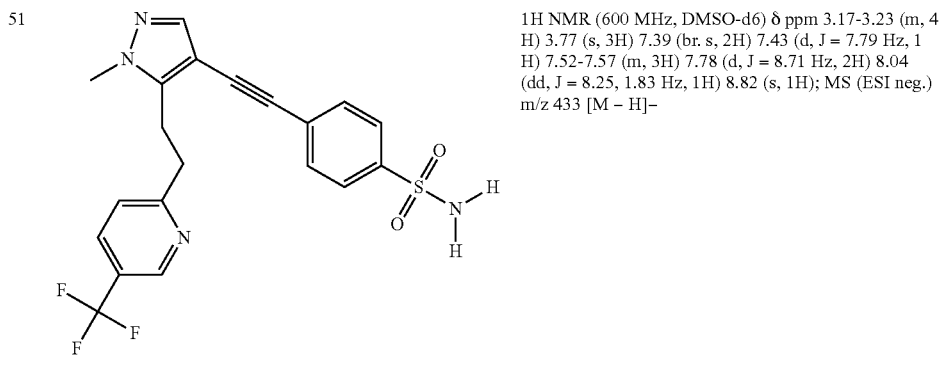 | 1H NMR (600 MHz, DMSO-d6) δ ppm 3.17-3.23 (m, 4 H) 3.77 (s, 3H) 7.39 (br. s, 2H) 7.43 (d, J = 7.79 Hz, 1 H) 7.52-7.57 (m, 3H) 7.78 (d, J = 8.71 Hz, 2H) 8.04 (dd, J = 8.25, 1.83 Hz, 1H) 8.82 (s, 1H); MS (ESI neg.) m/z 433 [M − H]− |
TABLE 2-6
| 52 | 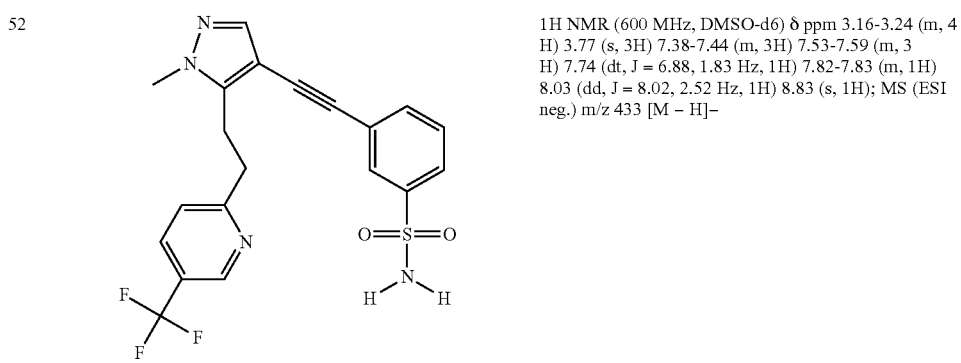 | 1H NMR (600 MHz, DMSO-d6) δ ppm 3.16-3.24 (m, 4 H) 3.77 (s, 3H) 7.38-7.44 (m, 3H) 7.53-7.59 (m, 3 H) 7.74 (dt, J = 6.88, 1.83 Hz, 1H) 7.82-7.83 (m, 1H) 8.03 (dd, J = 8.02, 2.52 Hz, 1H) 8.83 (s, 1H); MS (ESI neg.) m/z 433 [M − H]− |
| 53 | 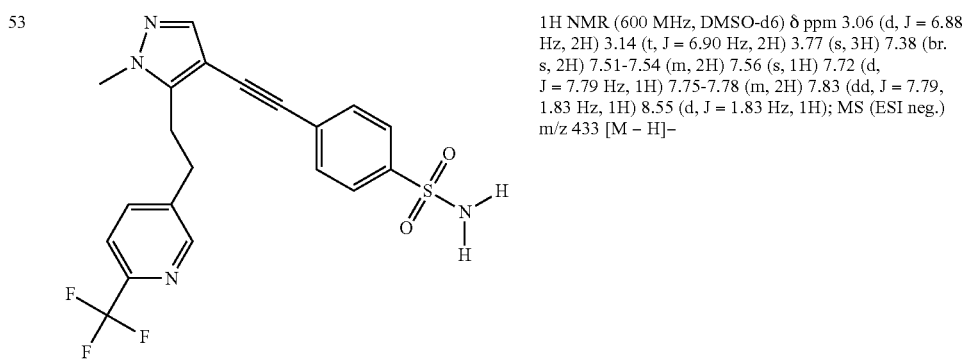 | 1H NMR (600 MHz, DMSO-d6) δ ppm 3.06 (d, J = 6.88 Hz, 2H) 3.14 (t, J = 6.90 Hz, 2H) 3.77 (s, 3H) 7.38 (br. s, 2H) 7.51-7.54 (m, 2H) 7.56 (s, 1H) 7.72 (d, J = 7.79 Hz, 1H) 7.75-7.78 (m, 2H) 7.83 (dd, J = 7.79, 1.83 Hz, 1H) 8.55 (d, J = 1.83 Hz, 1H); MS (ESI neg.) m/z 433 [M − H]− |
| 54 | 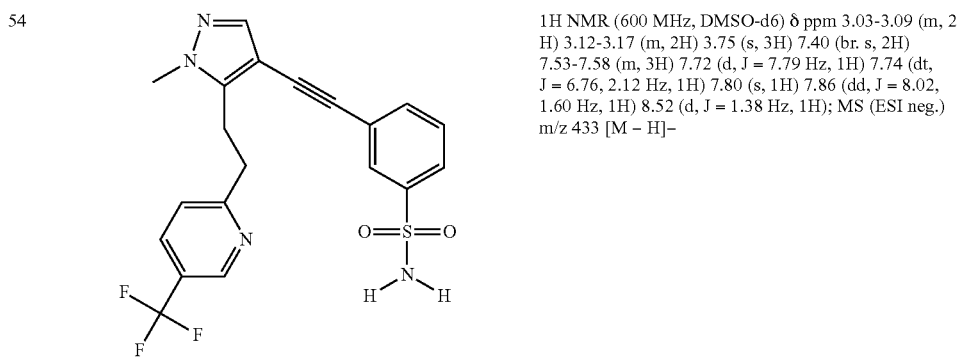 | 1H NMR (600 MHz, DMSO-d6) δ ppm 3.03-3.09 (m, 2 H) 3.12-3.17 (m, 2H) 3.75 (s, 3H) 7.40 (br. s, 2H) 7.53-7.58 (m, 3H) 7.72 (d, J = 7.79 Hz, 1H) 7.74 (dt, J = 6.76, 2.12 Hz, 1H) 7.80 (s, 1H) 7.86 (dd, J = 8.02, 1.60 Hz, 1H) 8.52 (d, J = 1.38 Hz, 1H); MS (ESI neg.) m/z 433 [M − H]− |

TABLE 2-6-continued
| 55 | | 1H NMR (600 MHz, DMSO-d6) δ ppm 2.84 (s, 3H) 3.66 (s, 3H) 4.41 (s, 2H) 7.39 (br. s., 2H) 7.50 (s, 1H) 7.54 (d, J = 8.25 Hz, 4H) 7.67 (d, J = 8.25 Hz, 2H) 7.77 (d, J = 8.71 Hz, 2H); MS (ESI pos.) m/z 449 [M + H]+ |
| --- | --- | --- |
| 56 | | 1H NMR (600 MHz, DMSO-d6) δ ppm 3.83 (s, 3H) 4.49 (d, J = 5.50 Hz, 2H) 6.79 (d, J = 8.71 Hz, 2H) 6.95 (t, J = 5.73 Hz, 1H) 7.35 (d, J = 8.71 Hz, 2H) 7.38 (s, 2 H) 7.59 (d, J = 8.71 Hz, 2H) 7.65 (s, 1H) 7.77 (d, J = 8.71 Hz, 2H); MS (ESI neg.) m/z: 433 [M − H]− |
| 57 | | 1H NMR (600 MHz, DMSO-d6) δ ppm 4.11 (s, 3H) 7.40 (br. s, 2H) 7.42-7.47 (m, 1H) 7.50-7.55 (m, 2 H) 7.63-7.67 (m, 2H) 7.77-7.84 (m, 4H) 7.87 (s, 1 H) 8.14 (d, J = 8.25 Hz, 1H) 8.33-8.39 (m, 1H) 9.06-9.12 (m, 1H); MS (ESI neg.) m/z 413 [M − H]− |
TABLE 2-7
| 58 |  | 1H NMR (600 MHz, DMSO-d6) δ ppm 3.79 (s, 3H) 4 89 (s, 2H) 4.92 (s, 2H) 7.38 (dd, J = 8.25, 1.83 Hz, 1 H) 7.41 (br. s, 2H) 7.43 (d, J = 8.25 Hz, 1H) 7.48-7.52 (m, 3H) 7.57 (s, 1H) 7.77 (d, J = 8.25 Hz, 2H); MS (ESI neg.) m/z 411 [M − H]− |
| --- | --- | --- |

TABLE 2-7-continued
| 59 | 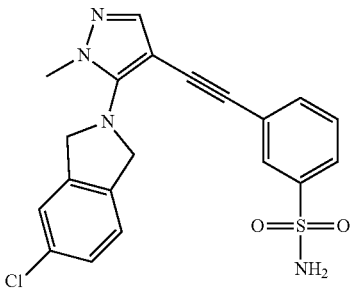 [SMILES: Cn1ncc(C#Cc2cccc(S(N)(=O)=O)c2)c1N1Cc2ccc(Cl)cc2C1] | 1H NMR (600 MHz, DMSO-d6) δ ppm 3.75 (s, 3H) 4.85-4.89 (m, 4H) 7.31-7.40 (m, 4H) 7.45 (s, 1H) 7.48-7.55 (m, 3H) 7.71 (dt, J = 7.34. 1.83 Hz, 1H) 7.75-7.76 (m, 1H); MS (ESI neg.) m/z 411 [M − H]− |
|---|---|---|
| 60 | 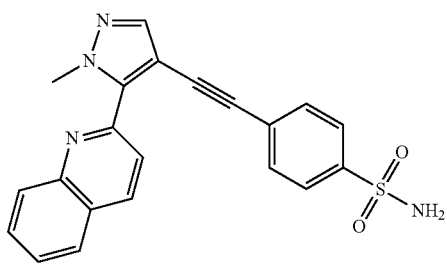 [SMILES: Cn1ncc(C#Cc2ccc(S(N)(=O)=O)cc2)c1-c1ccc2ccccc2n1] | 1H NMR (600 MHz, DMSO-d6) δ ppm 4.19 (s, 3H) 7.40 (s, 2H) 7.62-7.70 (m, 3H) 7.77-7.86 (m, 3H) 7.91 (s, 1H) 8.03-8.06 (m, 1H) 8.08-8.12 (m, 1H) 8.17 (d, J = 8.25 Hz, 1H) 8.61 (d, J = 8.25 Hz, 1H); MS (ESI pos.) m/z 389 [M + H]+ |
| 61 | 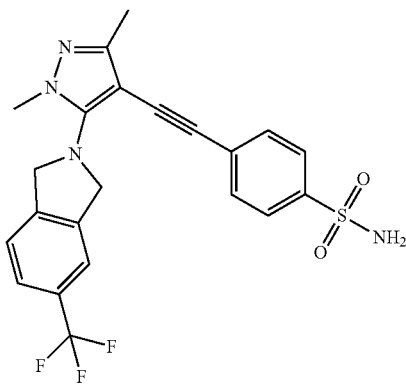 [SMILES: Cc1nn(C)c(N2Cc3ccc(C(F)(F)F)cc3C2)c1C#Cc1ccc(S(N)(=O)=O)cc1] | 1H NMR (600 MHz, DMSO-d6) δ pprn 2.18 (s, 3H) 3.73 (s, 3H) 4.97 <s, 4H) 7.39 (br. s, 2H) 7.48-7.51 (m, 2H) 7.62-7.65 (m, 1H) 7.67-7.70 (m, 1H) 7.75-7.78 (m, 2H) 7.82 (s, 1H); MS (ESI neg.) m/z 459 [M − H]− |
| 62 | 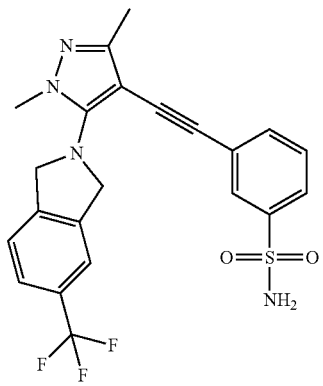 [SMILES: Cc1nn(C)c(N2Cc3ccc(C(F)(F)F)cc3C2)c1C#Cc1cccc(S(N)(=O)=O)c1] | 1H NMR (600 MHz, DMSO-d6) ppm 2.19 (s, 3H) 3.73 (s, 3H) 4.95-5.00 (m, 4H) 7.41 (s, 2H) 7.53-7.55 (m, 2H) 7.61-7.64 (m, 1H) 7.67-7.70 (m, 1H) 7.72-7.75 (m, 1H) 7.78-7.81 (m, 2H); MS (ESI neg.) m/z 459 [M − H]− |

TABLE 2-7-continued
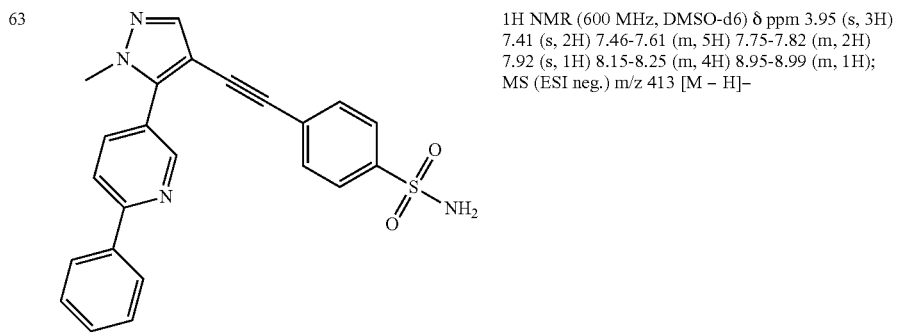
63 | 1H NMR (600 MHz, DMSO-d6) δ ppm 3.95 (s, 3H) 7.41 (s, 2H) 7.46-7.61 (m, 5H) 7.75-7.82 (m, 2H) 7.92 (s, 1H) 8.15-8.25 (m, 4H) 8.95-8.99 (m, 1H); MS (ESI neg.) m/z 413 [M − H]−
TABLE 2-8
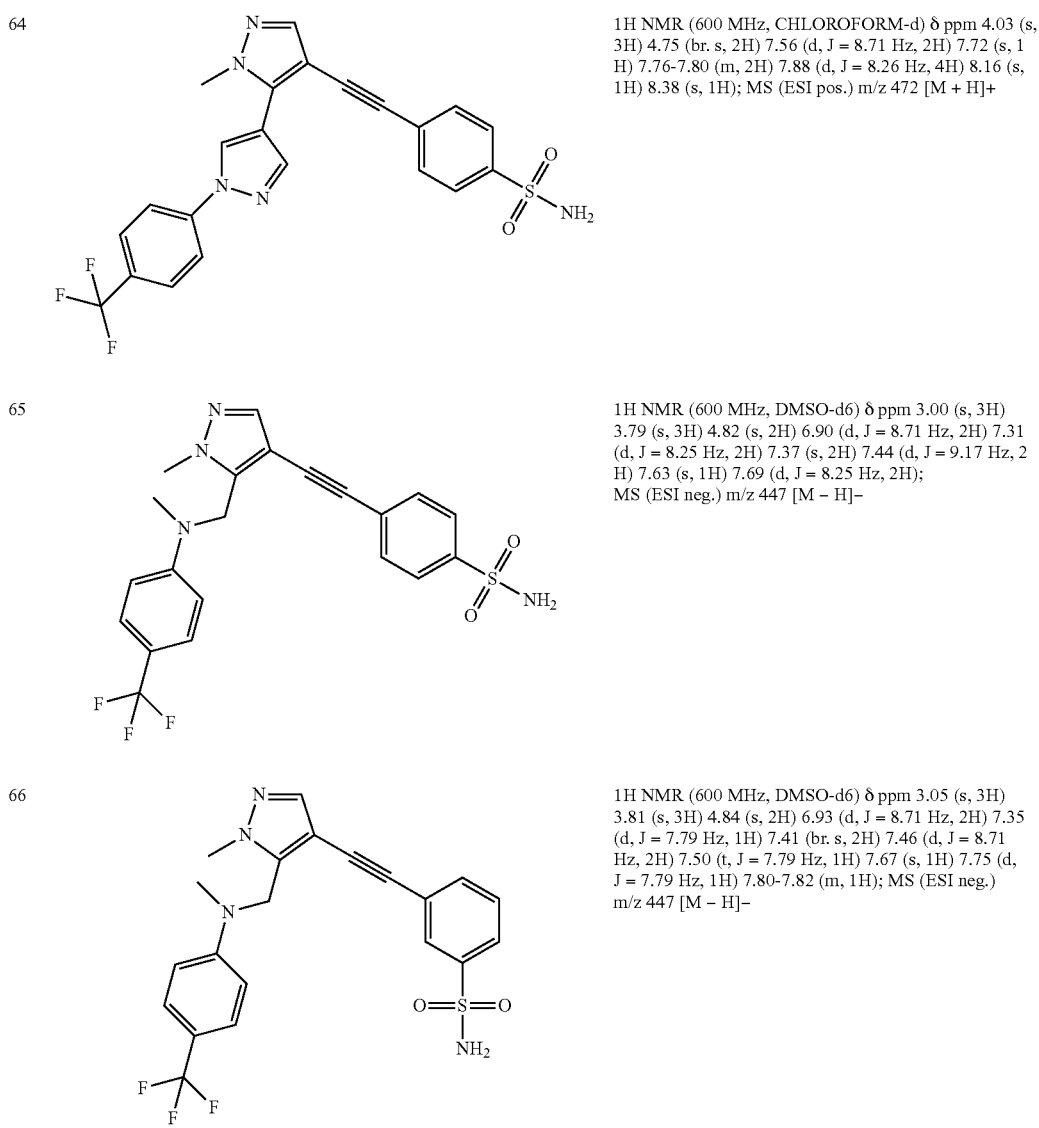
64 | 1H NMR (600 MHz, CHLOROFORM-d) δ ppm 4.03 (s, 3H) 4.75 (br. s, 2H) 7.56 (d, J = 8.71 Hz, 2H) 7.72 (s, 1H) 7.76-7.80 (m, 2H) 7.88 (d, J = 8.26 Hz, 4H) 8.16 (s, 1H) 8.38 (s, 1H); MS (ESI pos.) m/z 472 [M + H]+
65 | 1H NMR (600 MHz, DMSO-d6) δ ppm 3.00 (s, 3H) 3.79 (s, 3H) 4.82 (s, 2H) 6.90 (d, J = 8.71 Hz, 2H) 7.31 (d, J = 8.25 Hz, 2H) 7.37 (s, 2H) 7.44 (d, J = 9.17 Hz, 2H) 7.63 (s, 1H) 7.69 (d, J = 8.25 Hz, 2H); MS (ESI neg.) m/z 447 [M − H]−
66 | 1H NMR (600 MHz, DMSO-d6) δ ppm 3.05 (s, 3H) 3.81 (s, 3H) 4.84 (s, 2H) 6.93 (d, J = 8.71 Hz, 2H) 7.35 (d, J = 7.79 Hz, 1H) 7.41 (br. s, 2H) 7.46 (d, J = 8.71 Hz, 2H) 7.50 (t, J = 7.79 Hz, 1H) 7.67 (s, 1H) 7.75 (d, J = 7.79 Hz, 1H) 7.80-7.82 (m, 1H); MS (ESI neg.) m/z 447 [M − H]−

TABLE 2-8-continued

| 67 | *[structure]* | 1H NMR (600 MHz, DMSO-d6) δ ppm 3.82 (s, 3H) 7.34 (br. s, 2H) 7.43-7.48 (m, 2H) 7.66-7.71 (m, 2H) 7.81-7.86 (m, 2H) 7.95 (s, 1H) 8.30-8.35 (m, 2H) 8.75 (s, 2H); MS (ESI neg.) m/z 455 [M − H]− |
| --- | --- | --- |
| 68 | *[structure]* | 1H NMR (600 MHz, METHANOL-d3) δ ppm 4.04 (s, 3H) 6.60 (s, 2H) 7.51-7.60 (m, 1H) 7.67 (d, J = 6.88 Hz, 1H) 7.72-7.76 (m, 1H) 7.72-7.77 (m, 1H) 7.81-7.90 (m, 3H) 7.99 (s, 1H) 8.12 (d, J = 9.17 Hz, 1H) 8.33 (s, 1H) 8.93 (s, 1H); MS (ESI pos.) m/z 472 [M + H]+ |
| 69 | *[structure]* | 1H NMR (600 MHz, DMSO-d6) δ ppm 4.28 (s, 3H) 7.45 (br. s., 2H) 7.68-7.75 (m, 2H) 7.84-7.90 (m, 2H) 7.98 (d, J = 6.88 Hz, 2H) 8.02-8.06 (m, 1H) 8.25 (d, J = 6.88 Hz, 2H); MS (ESI neg.) m/z 472 [M − H]− |

TABLE 2-9

| 70 | *[structure]* | 1H NMR (600 MHz, DMSO-d6) δ ppm 4.28 (s, 3H) 7.46 (s, 2H) 7.64-7.68 (m, 1H) 7.74-7.77 (m, 1H) 7.84-7.87 (m, 1H) 7.97-8.01 (m, 3H) 8.04 (s, 1H) 8.24 (d, J = 8.25 Hz, 2H); MS (ESI neg.) m/z 472 [M − H]− |
| --- | --- | --- |

TABLE 2-9-continued

| | | |
|---|---|---|
| 71 | (structure) | 1H NMR (600 MHz, CHLOROFORM-d) δ ppm 3.94 (s, 3H) 7.08-7.20 (m, 2 H; 7.43-7.53 (m, 2 H; 7.58-7.71 (m, 3H) 7.75-7.86 (m, 2H) 8.06 (s, 1H) 8.25 (s, 2H); MS (ESI pos.) m/z 422 [M + H]+ |
| 72 | (structure) | 1H NMR (600 MHz, DMSO-d6) δ ppm 3.98 (s, 3H) 7.30 (br. s., 2H) 7.35-7.43 (m, 2H) 7.55-7.60 (m, 1 H) 7.66 (dd, J = 7.57, 1.15 Hz, 1H) 7.76 (dt, J = 7.79, 1.38 Hz, 1H) 7.78 (s, 1H) 7.88 (t, J = 1.60 Hz, 1H) 7.92-7.99 (m, 2H) 8.29 (s, 1H) 8.97 (s, 1H); MS (ESI pos.) m/z 422 [M + H]+ |
| 73 | (structure) | 1H NMR (600 MHz, DMSO-d6) δ ppm 4.33 (s, 3H) 7.45 (br. s, 2H) 7.73 (d, J = 8.25 Hz, 2H) 7.87 (d, J = 8.71 Hz, 2H) 8.00 (d, J = 8.25 Hz, 2H) 8.06 (s, 1H) 8.33 (d, J = 7.79 Hz, 2H); MS (ESI pos.) m/z 474 [M + H]+ |
| 74 | (structure) | 1H NMR (600 MHz, DMSO-d6) δ ppm 4.32 (s, 3H) 7.47 (br. s, 2H) 7.63-7.68 (m, 1H) 7.74-7.77 (m, 1 H) 7.83-7.87 (m, 1H) 7.96-8.01 (m, 3H) 8.06 (s, 1 H) 8.33 (d, J = 8.25 Hz, 2H); MS (ESI pos.) m/z 474 [M + H]+ |

TABLE 2-9-continued
| 75 | 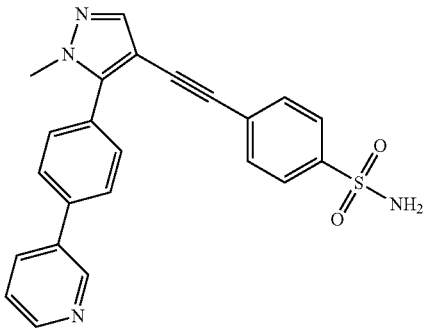 [SMILES: Cn1ncc(C#Cc2ccc(S(N)(=O)=O)cc2)c1-c1ccc(-c2cccnc2)cc1] | 1H NMR (600 MHz, DMSO-d6) δ ppm 3.94 (s, 3H) 7.43 (br. s, 2H) 7.55 (dd, J = 8.02, 4.81 Hz, 1H) 7.57-7.61 (m, 2H) 7.78-7.82 (m, 2H) 7.83-7.86 (m, 2H) 7.89 (s, 1H) 7.97-8.01 (m, 2H) 8.21 (dt, J = 8.14, 1.89 Hz, 1H) 8.64 (dd, J = 4.81, 1.60 Hz, 1H) 9.03 (d, J = 2.29 Hz, 1H); MS (ESI neg.) m/z 413 [M − H]− |
TABLE 2-10
| 76 | 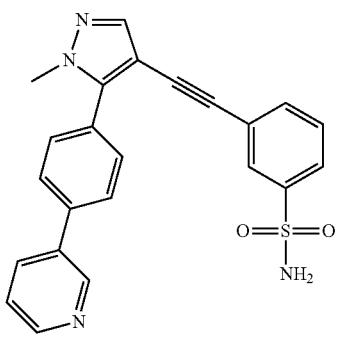 [SMILES: Cn1ncc(C#Cc2cccc(S(N)(=O)=O)c2)c1-c1ccc(-c2cccnc2)cc1] | 1H NMR (600 MHz, DMSO-d6) δ ppm 3.89 (s, 3H) 7.39 (br. s, 2H) 7.48-7.60 (m, 3H) 7.74 (dt, J = 7.68, 1.43 Hz, 1H) 7.77-7.82 (m, 3H) 7.85 (s, 1H) 7.92-7.96 (m, 2H) 8.16 (dt, J = 8.14, 1.89 Hz, 1H) 8.57-8.60 (m, 1H) 8.98 (d, J = 2.29 Hz, 1H); MS (ESI neg.) m/z 413 [M − H]− |
| 77 | 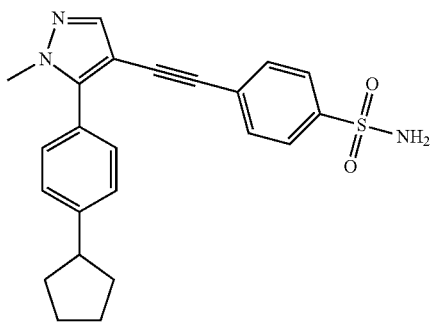 [SMILES: Cn1ncc(C#Cc2ccc(S(N)(=O)=O)cc2)c1-c1ccc(C2CCCC2)cc1] | 1H NMR (600 MHz, DMSO-d6) δ ppm 1.56-1.72 (m, 4H) 1.77-1.85 (m, 2H) 2.05-2.11 (m, 2H) 3.03-3.10 (m, 1H) 3.87 (s, 3H) 7.42 (br. s, 2H) 7.48 (d, J = 8.25 Hz, 9H) 7.55 (d, J = 8.25 Hz, 2H) 7.60 (d, J = 8.25 Hz, 2H) 7.79 (d, J = 8.25 Hz, 2H) 7.83 (s, 1H): MS (ESI neg.) m/z 404 [M − H]− |
| 78 | 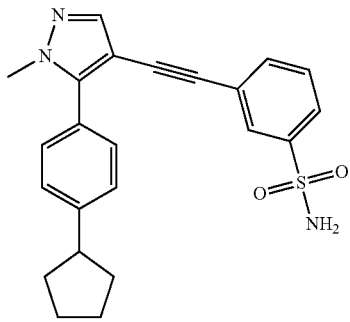 [SMILES: Cn1ncc(C#Cc2cccc(S(N)(=O)=O)c2)c1-c1ccc(C2CCCC2)cc1] | 1H NMR (600 MHz, DMSO-d6) δ ppm 1.52-1.69 (m, 4H) 1.73-1.81 (m, 2H) 2.01-2.08 (m, 2H) 3.03 (s, 1H) 3.83 (s. 3H) 7.38 (s, 2H) 7.44 (d, J = 8.25 Hz, 2H) 7.52-7.58 (m, 3H) 7.71-7.77 (m, 2H) 7.80 (s, 1H) 8.28 (s, 1H); MS (ESI neg.) m/z 404 [M − H]− |

TABLE 2-10-continued

| | | |
|---|---|---|
| 79 | | 1H NMR (600 MHz, CHLOROFORM-d) δ ppm 3.03-3.07 (m, 2H) 3.08-3.12 (m, 2H) 3.23 (s, 3H) 3.60 (s, 3H) 7.18 (d, J = 7.79 Hz, 2H) 7.51 (d, J = 7.79 Hz, 2 H) 7.61 (s, 1H) 7.89 (dd, J = 8.02, 2.06 Hz, 1H) 8.04 (d, J = 7.79 Hz, 1H) 8.67-8.69 (m, 1H); MS (ESI pos.) m/z 434 [M + H]+ |
| 80 | | 1H NMR (600 MHz, CHLOROFORM-d) δ ppm 3.08 (d, J = 6.88 Hz, 2H) 3.10-3.14 (m, 5H) 3.59 (s, 3H) 7.21 (d, J = 8.25 Hz, 2H) 7.50 (d, J = 8.25 Hz, 2H) 7.51 (dd, J = 8.25, 0.92 Hz, 1H) 7.65 (s, 1H) 8.16 (dd, J = 8.25, 2.29 Hz, 1H) 9.09 (dd, J = 2.29, 0.92 Hz, 1 H); MS (ESI pos.) m/z 434 [M + H]+ |
| 81 | | 1H NMR (600 MHz, CHLOROFORM-d) δ ppm 2.35 (s, 3H) 3.86 (s, 3H) 3.59 (s, 3H) 4.78 (br. S, 2H) 5.19 (s, 2H), 7.11 (d, J = 8.3 Hz, 2H), 7.88 (t, J = 7.8 Hz, 1H) 7.56 (d, J = 8.7 Hz, 2H) 7.64-7.66 (m, 1H) 7.85-7.87 (m, 1H) 8.02-8.03 (m, 1H); MS (ESI pos.) m/z 450 [M + H]+ |

TABLE 2-11

| | | |
|---|---|---|
| 82 | 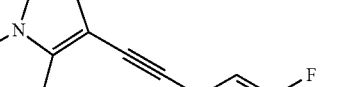 | 1H NMR (600 MHz, DMSO-d6) δ ppm 2.98-3.03 (m, 2 H) 3.08-3.13 (m, 2H) 3.70 (s, 3H) 7.33 (dd, J = 8.0, 1.6 Hz, 1H) 7.38 (d, J = 8.3 Hz, 2H) 7.42 (dd, J = 10.5, 1.4 Hz, 1H) 7.54-7.58 (m, 3H) 7.63 (br. s., 2H) 7.74 (t, J = 8.0 Hz, 1H); MS (ESI pos.) m/z 452 [M + H]+ |

TABLE 2-11-continued
| 83 | 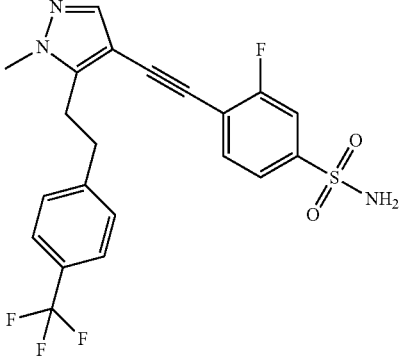 [SMILES: Cn1ncc(C#Cc2ccc(S(N)(=O)=O)cc2F)c1CCc1ccc(C(F)(F)F)cc1] | 1H NMR (600 MHz, DMSO-d6) δ ppm 3.00-3.05 (m, 2 H) 3.08-3.12 (m, 2H) 3.71 (s, 3H) 7.38 (d, J = 8.25 Hz, 2H) 7.51 (br. s, 2H) 7.57 (d, J = 8.25 Hz, 2H) 7.61 (s, 1 H) 7.61-7.68 (m, 3H); MS (ESI pos.) m/z 452 [M + H]+ |
| 84 | 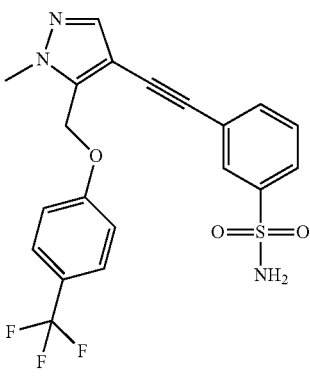 [SMILES: Cn1ncc(C#Cc2cccc(S(N)(=O)=O)c2)c1COc1ccc(C(F)(F)F)cc1] | 1H NMR (600 MHz, DMSO-d6) δ ppm 3.87 (s, 3H) 5.38 (s, 2H) 7.28 (d, J = 8.7 Hz, 2H) 7.40 (br. s, 2H) 7.55-7.58 (m, 1H) 7.66-7.68 (m, 3H) 7.74 (s, 1H) 7.77 (d, J = 7.8 Hz, 1H) 7.89 (s, 1H); MS (ESI pos.) m/z 436 [M + H]+ |
| 85 | 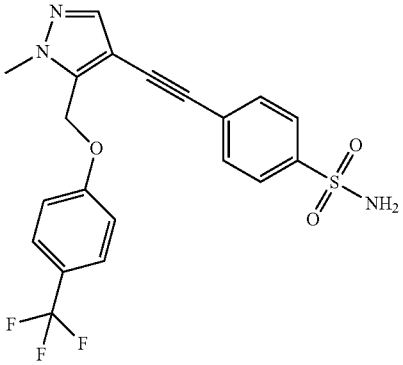 [SMILES: Cn1ncc(C#Cc2ccc(S(N)(=O)=O)cc2)c1COc1ccc(C(F)(F)F)cc1] | 1H NMR (600 MHz, DMSO-d6) δ ppm 3.88 (s, 3H) 5.38 (s, 2H) 7.28 (d, J = 8.7 Hz, 2H) 7.40 (br. s, 2H) 7.63-7.68 (m, 4H) 7.74 (s, 1H) 7.78 (d, J = 8.3 Hz, 2H); MS (ESI pos.) m/z 436 [M + H]+ |
| 86 | 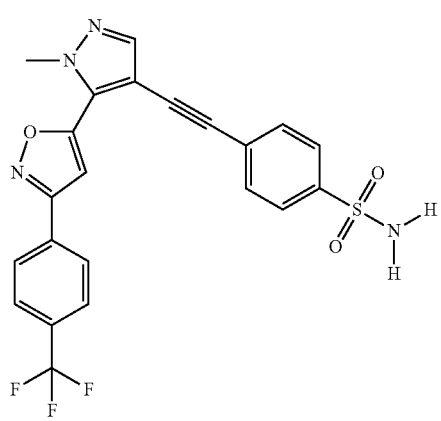 [SMILES: Cn1ncc(C#Cc2ccc(S(N)(=O)=O)cc2)c1-c1cc(-c2ccc(C(F)(F)F)cc2)no1] | 1H NMR (600 MHz, DMSO-d6) δ ppm 4.18 (s, 3H) 7.41-7.57 (m, 2H) 7.75 (d, J = 8.25 Hz, 2H) 7.81-7.91 (m, 3H) 7.98 (d, J = 8.25 Hz, 2H) 8.00 (s, 1H) 8.25 (d, J = 8.25 Hz, 2H); MS (ESI neg.) m/z 471 [M − H]− |

TABLE 2-11-continued

| 87 | (structure) | 1H NMR (600 MHz, DMSO-d6) δ ppm 4.15 (s, 3H) 7.44 (br. s., 2H) 7.59-7.65 (m, 1H) 7.72-7.76 (m, 1 H) 7.79 (s, 1H) 7.80-7.84 (m, 1H) 7.93 (d, J = 8.71 Hz, 2H) 7.95-7.98 (m, 2H) 8.21 (d, J = 8.25 Hz, 2H); MS (ESI neg.) m/z 471 [M − H]− |

TABLE 2-12

| 88 | (structure) | 1H NMR (600 MHz, DMSO-d6) δ ppm 3.61 (s, 3H) 5.71 (s, 2H) 7.42 (s, 2H) 7.54-7.60 (m, 3H) 7.68-7.75 (m, 2H) 7.79 (d, J = 8.25 Hz, 4H); MS (ESI neg.) m/z 434 [M − H]− |
| 89 | (structure) | 1H NMR (600 MHz, DMSO-d6) δ ppm 3.57 (s, 3H) 5.68 (s, 2H) 7.39 (br. s., 2H) 7.52-7.56 (m, 2H) 7.57-7.61 (m, 1H) 7.68-7.72 (m, 2H) 7.73-7.78 (m, 3 H) 7.84 (t, J = 1.60 Hz, 1H); MS (ESI neg.) m/z 434 [M − H]− |
| 90 | (structure) | 1H NMR (600 MHz, CHLOROFORM-d) δ ppm 0.93 (s, 9H) 3.05-3.13 (m, 4H) 3.59 (s, 3H) 3.73 (s, 2H) 7.21 (d, J = 7.79 Hz, 2H) 7.50-7.55 (m, 3H) 7.59 (s, 1 H) 7.66 (d, J = 7.79 Hz, 1H) 7.80-7.83 (m, 1H) 7.95-7.98 (m, 1H); MS (ESI pos.) m/z 505 [M + H]+ |

TABLE 2-12-continued

| | | |
|---|---|---|
| 91 | | 1H NMR (600 MHz, DMSO-d6) δ ppm 3.07 (s, 4H) 3.75 (s. 3H) 7.34-7.42 (m, 4H) 7.51-7.57 (m, 3H) 7.59 (s, 1H) 7.64 (d, J = 7.79 Hz, 1H) 7.79 (d, J = 7.79 Hz, 2H); MS (ESI neg.) m/z 432 [M − H]− |
| 92 | | 1H NMR (600 MHz, DMSO-d6) δ ppm 3.05-3.09 (m, 4 H) 3.74 (s, 3H) 7.35-7.42 (m, 4H) 7.53-7.58 (m, 3 H) 7.59 (s, 1H) 7.64 (d, J = 7.79 Hz, 1H) 7.75 (td, J = 4.58, 1.83 Hz, 1H) 7.81 (s, 1H); MS (ESI neg.) m/z 432 [M − H]− |
| 93 | | 1H NMR (600 MHz, DMSO-d6) δ ppm 3.00-3.06 (m, 2 H) 3.08-3.14 (m, 2H) 3.69 (s, 3H) 7.39 (s, 2H) 7.45 (s, 2H) 7.50 (s, 2H) 7.53-7.58 (m, 3H) 7.78 (d, J = 8.25 Hz, 2H); MS (ESI neg.) m/z 432 [M − H]− |

TABLE 2-13

| | | |
|---|---|---|
| 94 | | 1H NMR (600 MHz, DMSO-d6) δ ppm 2.98-3.07 (m, 2 H) 3.08-3.13 (m, 2H) 3.67 (s, 3H) 7.40 (br. s., 2H) 7.43-7.52 (m, 4H) 7.53-7.61 (m, 3H) 7.75 (d, J = 7.34 Hz, 1H) 7.82 (s, 1H); MS (ESI neg.) m/z 432 [M − H]− |

TABLE 2-13-continued

| 95 | (structure) | 1H NMR (600 MHz, DMSO-d6) δ ppm 3.58 (s, 3H) 4.80 (d, J = 6.42 Hz, 2H) 6.85 (t, J = 6.65 Hz, 1H) 7.24 (d, J = 8.25 Hz, 2H) 7.30 (s, 1H) 7.33 (br. s., 2H) 7.56 (d, J = 7.79 Hz, 2H) 7.67 (d, J = 8.25 Hz, 4H); MS (ESI neg.) m/z 433 [M − H]− |
| --- | --- | --- |
| 96 | (structure) | 1H NMR (600 MHz, DMSO-d6) δ ppm 3.23-3.29 (m, 4 H) 3.84 (s, 3H) 7.42 (br. s, 2H) 7.54 (d, J = 8.71 Hz, 2 H) 7.58 (s, 1H) 7.81 (d, J = 8.25 Hz, 2H) 8.16 (d, J = 9.63 Hz, 1H) 8.73 (s, 1H); MS (ESI neg.) m/z 451 [M − H]− |
| 97 | (structure) | 1H NMR (600 MHz, DMSO-d6) δ ppm 3.21-3.27 (m, 4 H) 3.82 (s, 3H) 7.41 (br. s., 2H) 7.50-7.59 (m, 3H) 7.76 (d, J = 7.34 Hz, 1H) 7.79 (s, 1H) 8.11 (d, J = 9.17 Hz, 1H) 8.72 (s, 1H); MS (ESI neg.) m/z 451 [M − H]− |

Example 22

3-{[1-methyl-5-(naphthalen-2-yl)-1H-pyrazol-4-yl]ethynyl}benzenesulfonamide

Example 23

3-{[5-(biphenyl-4-yl)-1-methyl-1H-pyrazol-4-yl]ethynyl}benzenesulfonamide

Example 24

3-[(1-methyl-5-phenyl-1H-pyrazol-4-yl)ethynyl]benzenesulfonamide

Example 25

3-({1-methyl-5-[4-(trifluoromethyl)phenyl]-1H-pyrazol-4-yl}ethynyl)benzenesulfonamide Example 26

1-methyl-4-(phenylethynyl)-5-[4-(trifluoromethyl)phenyl]-1H-pyrazole

Example 27

3-{[5-(benzylamino)-1-methyl-1H-pyrazol-4-yl]ethynyl}benzenesulfonamide

Example 28

3-{[5-(1,3-dihydro-2H-isoindol-2-yl)-1-methyl-1H-pyrazol-4-yl]ethynyl}benzenesulfonamide Example 29

3-[(1-methyl-5-{[4-(trifluoromethyl)benzyl]amino}-1H-pyrazol-4-yl)ethynyl]benzenesulfonamide Example 30

3-({1-methyl-5-[5-(trifluoromethyl)pyridin-2-yl]-1H-pyrazol-4-yl}ethynyl)benzenesulfonamide Example 31

3-({1-methyl-5-[3-(trifluoromethyl)phenyl]-1H-pyrazol-4-yl}ethynyl)benzenesulfonamide

Example 32

3-({1-methyl-5-[2-(trifluoromethyl)phenyl]-1H-pyrazol-4-yl}ethynyl)benzenesulfonamide

Example 33

3-({1-methyl-5-[4-(trifluoromethoxy)phenyl]-1H-pyrazol-4-yl}ethynyl)benzenesulfonamide

Example 34

4-({1-methyl-5-[4-(trifluoromethoxy)phenyl]-1H-pyrazol-4-yl}ethynyl)benzenesulfonamide

Example 35

N-{1-methyl-4-[(3-sulfamoylphenyl)ethynyl]-1H-pyrazol-5-yl}-4-(trifluoromethyl)benzamide

Example 36

4-{[5-(1,3-dihydro-2H-benzo[f]isoindol-2-yl)-1-methyl-1H-pyrazol-4-yl]ethynyl}benzenesulfonamide

Example 37

4-({1-methyl-5-[4-(2,2,2-trifluoroethoxy)phenyl]-1H-pyrazol-4-yl}ethynyl)benzenesulfonamide

Example 38

3-({1-methyl-5-[4-(2,2,2-trifluoroethoxy)phenyl]-1H-pyrazol-4-yl}ethynyl)benzenesulfonamide

Example 39

1-methyl-4-[(3-sulfamoylphenyl)ethynyl]-N-[4-(trifluoromethyl)phenyl]-1H-pyrazol-5-carboxamide

Example 40

3-{[5-(1,3-dihydro-2H-benzo[f]isoindol-2-yl)-1-methyl-1H-pyrazol-4-yl]ethynyl}benzenesulfonamide

Example 41

4-{[1-methyl-5-(2-phenylethyl)-1H-pyrazol-4-yl]ethynyl}benzenesulfonamide

Example 42

3-{[1-methyl-5-(2-phenylethyl)-1H-pyrazol-4-yl]ethynyl}benzenesulfonamide

Example 43

3-{[1-methyl-5-(3-phenylpropyl)-1H-pyrazol-4-yl]ethynyl}benzenesulfonamide

Example 44

4-{[1-methyl-5-(3-phenylpropyl)-1H-pyrazol-4-yl]ethynyl}benzenesulfonamide

Example 45

3-[(1-methyl-5-{2-[4-(trifluoromethyl)phenyl]ethyl}-1H-pyrazol-4-yl)ethynyl]benzenesulfonamide

Example 46

3-({1-methyl-5-[5-(trifluoromethyl)-1,3-dihydro-2H-isoindol-2-yl]-1H-pyrazol-4-yl}ethynyl)benzenesulfonamide

Example 47

4-({1-methyl-5-[5-(trifluoromethyl)-1,3-dihydro-2H-isoindol-2-yl]-1H-pyrazol-4-yl}ethynyl)benzenesulfonamide

Example 48

3-({1-methyl-5-[6-(trifluoromethyl)pyridin-3-yl]-1H-pyrazol-4-yl}ethynyl)benzenesulfonamide

Example 49

4-({1-methyl-5-[6-(trifluoromethyl)pyridin-3-yl]-1H-pyrazol-4-yl}ethynyl)benzenesulfonamide

Example 50

4-({1-methyl-5-[5-(trifluoromethyl)pyridin-2-yl]-1H-pyrazol-4-yl}ethynyl)benzenesulfonamide

Example 51

4-[(1-methyl-5-{2-[5-(trifluoromethyl)pyridin-2-yl]ethyl}-1H-pyrazol-4-yl)ethynyl]benzenesulfonamide

Example 52

3-[(1-methyl-5-{2-[5-(trifluoromethyl)pyridin-2-yl]ethyl}-1H-pyrazol-4-yl)ethynyl]benzenesulfonamide

Example 53

4-[(1-methyl-5-{2-[6-(trifluoromethyl)pyridin-3-yl]ethyl}-1H-pyrazol-4-yl)ethynyl]benzenesulfonamide

Example 54

3-[(1-methyl-5-{2-[6-(trifluoromethyl)pyridin-3-yl]ethyl}-1H-pyrazol-4-yl)ethynyl]benzenesulfonamide

Example 55

4-[(1-methyl-5-{methyl[4-(trifluoromethyl)benzyl]amino}-1H-pyrazol-4-yl)ethynyl]benzenesulfonamide

Example 56

4-{[1-methyl-5-({[4-(trifluoromethyl)phenyl]
amino}methyl)-1H-pyrazol-4-yl]
ethynyl}benzenesulfonamide

Example 57

4-{[1-methyl-5-(5-phenylpyridin-2-yl)-1H-pyrazol-
4-yl]ethynyl}benzenesulfonamide

Example 58

4-{[5-(5-chloro-1,3-dihydro-2H-isoindol-2-yl)-1-
methyl-1H-pyrazol-4-yl]
ethynyl}benzenesulfonamide

Example 59

3-{[5-(5-chloro-1,3-dihydro-2H-isoindol-2-yl)-1-
methyl-1H-pyrazol-4-yl]
ethynyl}benzenesulfonamide

Example 60

4-{[1-methyl-5-(quinolin-2-yl)-1H-pyrazol-4-yl]
ethynyl}benzenesulfonamide

Example 61

4-({1,3-dimethyl-5-[5-(trifluoromethyl)-1,3-dihydro-
2H-isoindol-2-yl]-1H-pyrazol-4-yl}ethynyl)benzene-
sulfonamide

Example 62

3-({1,3-dimethyl-5-[5-(trifluoromethyl)-1,3-dihydro-
2H-isoindol-2-yl]-1H-pyrazol-4-yl}ethynyl)benzene-
sulfonamide

Example 63

4-{[1-methyl-5-(6-phenylpyridin-3-yl)-1H-pyrazol-
4-yl]ethynyl}benzenesulfonamide

Example 64

4-({2-methyl-1'-[4-(trifluoromethyl)phenyl]-1'H,2H-
3,4'-bipyrazol-4-yl}ethynyl)benzenesulfonamide

Example 65

4-{[1-methyl-5-({methyl[4-(trifluoromethyl)phenyl]
amino}methyl)-1H-pyrazol-4-yl]
ethynyl}benzenesulfonamide

Example 66

3-{[1-methyl-5-({methyl[4-(trifluoromethyl)phenyl]
amino}methyl)-1H-pyrazol-4-yl]
ethynyl}benzenesulfonamide

Example 67

4-{[5-(1,3-dioxo-1,3-dihydro-2H-benzo[f]isoindol-
2-yl)-1-methyl-1H-pyrazol-4-yl]
ethynyl}benzenesulfonamide

Example 68

3-({2-methyl-1'-[4-(trifluoromethyl)phenyl]-1'H,2H-
3,4'-bipyrazol-4-yl}ethynyl)benzenesulfonamide

Example 69

4-[(1-methyl-5-{5-[4-(trifluoromethyl)phenyl]-1,3,4-
oxadiazol-2-yl}-1H-pyrazol-4-yl)ethynyl]benzene-
sulfonamide

Example 70

3-[(1-methyl-5-{5-[4-(trifluoromethyl)phenyl]-1,3,4-
oxadiazol-2-yl}-1H-pyrazol-4-yl)ethynyl]benzene-
sulfonamide

Example 71

4-{[1'-(4-fluorophenyl)-2-methyl-1'H,2H-3,4'-bi-
pyrazol-4-yl]ethynyl}benzenesulfonamide

Example 72

3-{[1'-(4-fluorophenyl)-2-methyl-1'H,2H-3,4'-bi-
pyrazol-4-yl]ethynyl}benzenesulfonamide

Example 73

4-[(1-methyl-5-{3-[4-(trifluoromethyl)phenyl]-1,2,4-
oxadiazol-5-yl}-1H-pyrazol-4-yl)ethynyl]benzene-
sulfonamide

Example 74

3-[(1-methyl-5-{3-[4-(trifluoromethyl)phenyl]-1,2,4-
oxadiazol-5-yl}-1H-pyrazol-4-yl)ethynyl]benzene-
sulfonamide

Example 75

4-({1-methyl-5-[4-(pyridin-3-yl)phenyl]-1H-pyrazol-
4-yl}ethynyl)benzenesulfonamide

Example 76

3-({1-methyl-5-[4-(pyridin-3-yl)phenyl]-1H-pyrazol-
4-yl}ethynyl)benzenesulfonamide

Example 77

4-{[5-(4-cyclopentylphenyl)-1-methyl-1H-pyrazol-4-
yl]ethynyl}benzenesulfonamide

Example 78

3-{[5-(4-cyclopentylphenyl)-1-methyl-1H-pyrazol-4-
yl]ethynyl}benzenesulfonamide

Example 79

2-(methylsulfonyl)-5-[(1-methyl-5-{2-[4-(trifluo-
romethyl)phenyl]ethyl}-1H-pyrazol-4-yl)ethynyl]
pyridine

Example 80

5-(methylsulfonyl)-2-[(1-methyl-5-{2-[4-(trifluoromethyl)phenyl]ethyl}-1H-pyrazol-4-yl)ethynyl]pyridine

Example 81

3-[(1,3-dimethyl-5-{[4-(trifluoromethyl)phenoxy]methyl}-1H-pyrazol-4-yl)ethynyl]benzenesulfonamide

Example 82

2-fluoro-4-[(1-methyl-5-{2-[4-(trifluoromethyl)phenyl]ethyl}-1H-pyrazol-4-yl)ethynyl]benzenesulfonamide

Example 83

3-fluoro-4-[(1-methyl-5-{2-[4-(trifluoromethyl)phenyl]ethyl}-1H-pyrazol-4-yl)ethynyl]benzenesulfonamide

Example 84

3-[(1-methyl-5-{[4-(trifluoromethyl)phenoxy]methyl}-1H-pyrazol-4-yl)ethynyl]benzenesulfonamide

Example 85

4-[(1-methyl-5-{[4-(trifluoromethyl)phenoxy]methyl}-1H-pyrazol-4-yl)ethynyl]benzenesulfonamide

Example 86

4-[(1-methyl-5-{3-[4-(trifluoromethyl)phenyl]-1,2-oxazol-5-yl}-1H-pyrazol-4-yl)ethynyl]benzenesulfonamide

Example 87

3-[(1-methyl-5-{3-[4-(trifluoromethyl)phenyl]-1,2-oxazol-5-yl}-1H-pyrazol-4-yl)ethynyl]benzenesulfonamide

Example 88

4-[(1-methyl-5-{[4-(trifluoromethyl)benzyl]oxy}-1H-pyrazol-4-yl)ethynyl]benzenesulfonamide

Example 89

3-[(1-methyl-5-{[4-(trifluoromethyl)benzyl]oxy}-1H-pyrazol-4-yl)ethynyl]benzenesulfonamide

Example 90

2,2-dimethylpropyl 3-[(1-methyl-5-{2-[4-(trifluoromethyl)phenyl]ethyl}-1H-pyrazol-4-yl)ethynyl]benzenesulfonate

Example 91

4-[(1-methyl-5-{2-[2-(trifluoromethyl)phenyl]ethyl}-1H-pyrazol-4-yl)ethynyl]benzenesulfonamide

Example 92

3-[(1-methyl-5-{2-[2-(trifluoromethyl)phenyl]ethyl}-1H-pyrazol-4-yl)ethynyl]benzenesulfonamide

Example 93

4-[(1-methyl-5-{2-[3-(trifluoromethyl)phenyl]ethyl}-1H-pyrazol-4-yl)ethynyl]benzenesulfonamide

Example 94

3-[(1-methyl-5-{2-[3-(trifluoromethyl)phenyl]ethyl}-1H-pyrazol-4-yl)ethynyl]benzenesulfonamide

Example 95

4-[(1-methyl-5-{[4-(trifluoromethyl)benzyl]amino}-1H-pyrazol-4-yl)ethynyl]benzene sulfonamide

Example 96

4-[(5-{2-[3-fluoro-5-(trifluoromethyl)pyridin-2-yl]ethyl}-1-methyl-1H-pyrazol-4-yl)ethynyl]benzenesulfonamide

Example 97

3-[(5-{2-[3-fluoro-5-(trifluoromethyl)pyridin-2-yl]ethyl}-1-methyl-1H-pyrazol-4-yl)ethynyl]benzenesulfonamide

Example 98

3-{[1-Methyl-5-{[4-(trifluoromethyl)phenyl]amino}methyl)-1H-pyrazol-4-yl]ethynyl}benzenesulfonamide

[Formula 37]

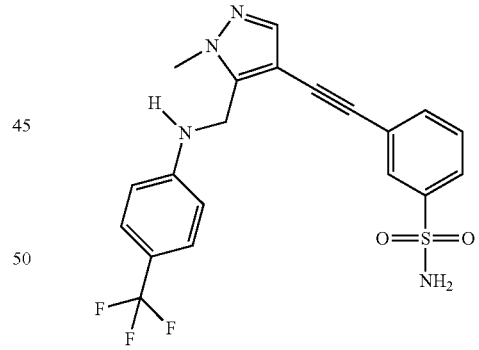

A mixture of the 3-[(5-formyl-1-methyl-1H-pyrazol-4-yl)ethynyl]benzenesulfonamide (100 mg) obtained in Production Example 28, 4-(trifluoromethyl)aniline (84 mg), acetic acid (300 µL) and ethanol (2.7 mL) was stirred at a room temperature for 1 hour. Thereafter, under cooling in an ice bath, sodium cyanoborohydride (43 mg) was added to the reaction solution, and the obtained solution was then stirred at a room temperature for 2 days. Thereafter, a saturated sodium hydrogencarbonate aqueous solution was added to the reaction solution, and the obtained mixture was then extracted with ethyl acetate. The gathered organic layer was washed with water, and was then dried over anhydrous sodium sulfate, followed by vacuum concentration. The residue was purified by reverse-phase column chromatography (CAPCELL PAK, 0.1% trifluoroacetic acid/water:acetonitrile=90:

10 to 10:90), and a saturated sodium hydrogencarbonate aqueous solution was then added to a fraction that contained a product of interest, followed by extraction with chloroform. The organic layer was concentrated under a reduced pressure, so as to obtain the title compound (23 mg) in the form of a light yellow solid.

1H NMR (600 MHz, DMSO-d$_6$) δ ppm 3.83 (s, 3H) 4.49 (d, J=5.50 Hz, 2H) 6.79 (d, J=8.71 Hz, 2H) 6.96 (t, J=5.50 Hz, 1H) 7.35 (d, J=8.71 Hz, 2H) 7.39 (br. s, 2H) 7.56 (t, J=7.80 Hz, 1H) 7.63 (dt, J=7.79, 1.38 Hz, 1H) 7.66 (s, 1H) 7.76 (dt, J=7.79, 1.60 Hz, 1H) 7.89 (t, J=1.60 Hz, 1H). MS (ESI neg.) m/z: 433 [M−H]$^−$ Example 99

4-({5-[(4-Fluorophenoxy)methyl]-1-methyl-1H-pyrazol-4-yl}ethynyl)benzenesulfonamide

[Formula 38]

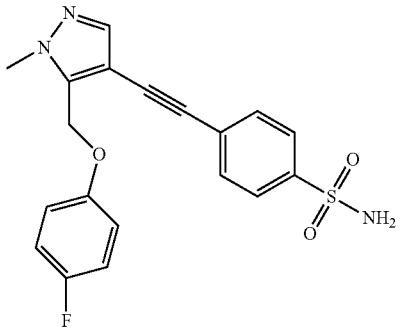

To a tetrahydrofuran (2.0 mL) solution that contained the 4-{[5-(hydroxymethyl)-1-methyl-1H-pyrazol-4-yl]ethynyl}benzenesulfonamide (30 mg) obtained in Production Example 29, 4-fluorophenol (23 mg) and triphenylphosphine (54 mg), 2 M diisopropyl azodicarboxylate (100 µL, toluene solution) was added at a room temperature, and the obtained solution was then stirred overnight. Thereafter, water and 2 M hydrochloric acid were added to the reaction solution, and the obtained mixture was then extracted with ethyl acetate. The organic layer was washed with water, and was then dried over anhydrous sodium sulfate, followed by vacuum concentration. The residue was purified by column chromatography (silica gel cartridge, chloroform to chloroform:methanol=90:1) and reverse-phase column chromatography (CAPCELL PAK, 0.1% trifluoroacetic acid/water:acetonitrile=90:10 to 10:90). Subsequently, a saturated sodium hydrogencarbonate aqueous solution was added to a fraction that contained a product of interest, and the obtained mixture was then extracted with chloroform. The organic layer was concentrated under a reduced pressure, so as to obtain the title compound (5 mg) in the form of a light yellow solid.

1H NMR (600 MHz, DMSO-d$_6$) δ ppm 3.87 (s, 3H) 5.26 (s, 2H) 7.09-7.14 (m, 4H) 7.38 (br. s., 2H) 7.65 (d, J=6.00 Hz, 2H) 7.71 (s, 1H) 7.79 (d, J=6.00 Hz, 2H). MS (ESI pos.) m/z: 386 [M+H]$^+$.

The compounds of Example 100 to Example 102, which are shown in Table 3 below, were obtained by the same method as that in Example 99.

TABLE 3

| Example | Structural formula | Instrumental data |
|---|---|---|
| 100 | 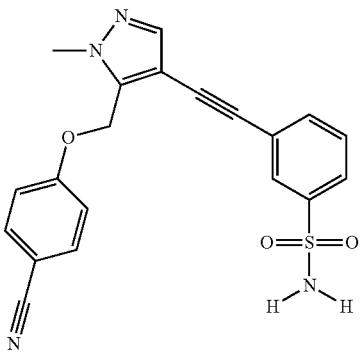 [SMILES: Cn1ncc(C#Cc2cccc(S(N)(=O)=O)c2)c1COc1ccc(C#N)cc1] | 1H NMR (600 MHz, CHLOROFORM-d) δ ppm 3.95 (s, 3H) 4.81 (br. s, 2H) 5.24 (s, 2H) 7.11 (d, J = 9.17 Hz, 2H) 7.51 (t, J = 7.79 Hz, 1H) 7.58-7.67 (m, 4H) 7.87 (d, J = 7.79 Hz, 1H) 8.02 (s, 1H); MS (ESI neg.) m/z: 391 [M − H]− |
| 101 | 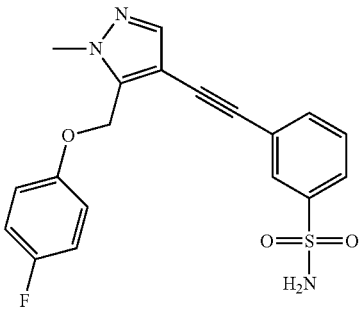 [SMILES: Cn1ncc(C#Cc2cccc(S(N)(=O)=O)c2)c1COc1ccc(F)cc1] | 1H NMR (600 MHz, CHLOROFORM-d) δ ppm 3.95 (s, 3H) 4.80 (br. s, 2H) 5.14 (s, 2H) 6.93-7.02 (m, 4H) 7.49 (t, J = 8.02 Hz, 1H) 7.62 (s, 1H) 7.64 (d, J = 7.80 Hz, 1H) 7.83-7.87 (m, 1H) 8.01 (s, 1H); MS (ESI neg.) m/z: 384 [M − H]− |

TABLE 3-continued

| Example | Structural formula | Instrumental data |
|---|---|---|
| 102 | | 1H NMR (600 MHz, CHLOROFORM-d) δ ppm 3.95 (s, 3H) 4.80 (br. s, 2H) 5.17 (s, 2H) 6.69-6.74 (m, 1H) 6.77-6.84 (m, 2H) 7.22-7.28 (m, 1H) 7.49 (t, J = 7.79 Hz, 1H) 7.63 (s, 1H) 7.67 (d, J = 7.79 Hz, 1H) 7.86 (d, J = 7.79 Hz, 1H) 8.04 (t, J = 1.60 Hz, 1H); MS (ESI neg.) m/z: 384 [M − H]− |

Example 100

3-({5-[(4-cyanophenoxy)methyl]-1-methyl-1H-pyrazol-4-yl}ethynyl)benzenesulfonamide    20

Example 101

3-({5-[(4-fluorophenoxy)methyl]-1-methyl-1H-pyrazol-4-yl}ethynyl)benzenesulfonamide    25

Example 102

3-({5-[(3-fluorophenoxy)methyl]-1-methyl-1H-pyrazol-4-yl}ethynyl)benzenesulfonamide    30

The compounds of Example 103 to Example 110, which are shown in Table 4 below, were obtained by the same method as that in Example 21.

TABLE 4-1

| Example | Structural formula | Instrumental data |
|---|---|---|
| 103 | | 1H NMR (600 MHz, DMSO-d6) δ ppm 0.85-0.95 (m, 2H) 1.05-1.26 (m, 4H) 1.43-1.50 (m, 2H) 1.55 (d, J = 9.17 Hz, 1H) 1.62 (d, J = 12.38 Hz, 2H) 1.77 (d, J - 11.92 Hz, 2H) 2.78 (t, J - 7.57 Hz, 2H) 3.76 (s, 3H) 7.40 (s, 2H) 7.54-7.63 (m, 3H) 7.75 (d, J = 7.79 Hz, 1H) 7.83 (s, 1H); MS (ESI pos.) m/z: 372 [M + H]+ |
| 104 | | 1H NMR (600 MHz, DMSO-d6) δ ppm 0.87-0.98 (m, 2H) 1.08-1.31 (m, 4H) 1.46-1.54 (m, 2H) 1.55-1.68 (m, 3H) 1.81 (d, J = 12.38 Hz, 2H) 2.81 (t, J = 7.79 Hz, 2H) 3.79 (s, 3H) 7.42 (s, 2H) 7.58-7.64 (m, 3H) 7.82 (d, J = 8.25 Hz, 2H); MS (ESI pos.) m/z: 372 [M + H]+ |

TABLE 4-1-continued

| Example | Structural formula | Instrumental data |
| --- | --- | --- |
| 105 | | 1H NMR (600 MHz, DMSO-d6) δ ppm 3.24-3.26 (m, 2H) 3.86 (s, 3H) 4.35 (t, J = 6.42 Hz, 2H) 7.10 (d, J = 8.71 Hz, 2H) 7.37 (br. s., 2H) 7.49-7.54 (m, 2H) 7.59 (d, J = 8.71 Hz, 2H) 7.63 (s, 1H) 7.72-7.77 (m, 2H); MS (ESI neg.) m/z: 448 [M − H]− |
| 106 | | 1H NMR (600 MHz, DMSO-d6) δ ppm 3.29-3.32 (m, 2H) 3.86 (s, 3H) 4.35 (t, J = 6.42 Hz, 2H) 7.09 (d, J = 8.71 Hz, 2H) 7.38 (br. s., 2H) 7.49-7.55 (m, 2H) 7.58 (d, J = 8.71 Hz, 2H) 7.64 (s, 1H) 7.72-7.76 (m, 1H) 7.83-7.86 (m, 1H): MS (ESI neg.) m/z: 448 [M − H]− |
| 107 | | 1H NMR (600 MHz, DMSO-d6) δ ppm 3.91 (s, 3H) 5.50 (s, 2H) 6.98 (dd, J = 9.08, 3.30 Hz, 1H) 7.43 (s, 2H) 7.55-7.62 (m, 1H) 7.64-7.69 (m, 1H) 7.69-7.82 (m, 3H) 7.84-7.93 (m, 1H) 8.20 (d, J = 3.30 Hz, 1H); MS (ESI pos.) m/z: 387 [M + H]+ |

TABLE 4-2
| 108 | 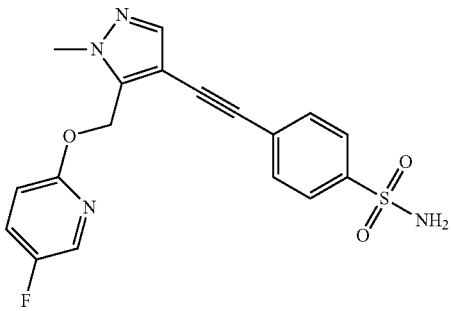 [SMILES: Cn1ncc(C#Cc2ccc(S(N)(=O)=O)cc2)c1COc1ccc(F)cn1] | 1H NMR (600 MHz, DMSO-d6) δ ppm 3.83 (s, 3H) 5.42 (s, 2H) 6.90 (dd, J = 9.08, 3.30 Hz, 1H) 7.34 (br. s., 2H) 7.55 (d, J = 8.26 Hz, 2H) 7.63-7.69 (m, 2H) 7.73 (d, J = 8.26 Hz, 2H) 8.13 (d, J = 2.89 Hz, 1H); MS (ESI pos.) m/z: 387 [M + H]+ |
|---|---|---|
| 109 | 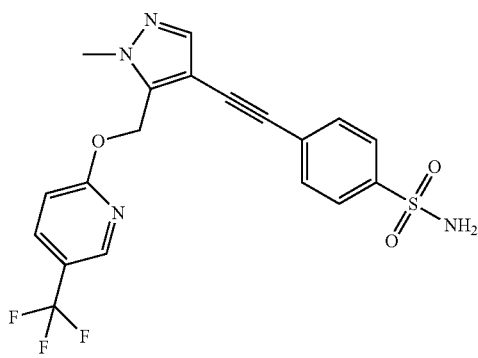 [SMILES: Cn1ncc(C#Cc2ccc(S(N)(=O)=O)cc2)c1COc1ccc(C(F)(F)F)cn1] | 1H NMR (600 MHz, DMSO-d6) δ ppm 3.89 (s, 3H) 5.59 (s, 2H) 7.09 (d, J = 8.67 Hz, 1H) 7.40 (s, 2H) 7.58 (d, J = 8.26 Hz, 2H) 7.72 (s, 1H) 7.77 (d, J = 8.26 Hz, 2H) 8.10 (dd, J = 8.67, 2.48 Hz, 1H) 8.62 (s, 1H); MS (ESI pos.) m/z: 437 [M + H]+ |
| 110 | 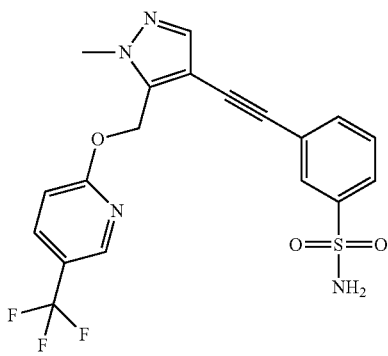 [SMILES: Cn1ncc(C#Cc2cccc(S(N)(=O)=O)c2)c1COc1ccc(C(F)(F)F)cn1] | 1H NMR (600 MHz, DMSO-d6) δ ppm 3.90 (s, 3H) 5.59 (s, 2H) 7.09 (d, J = 9.08 Hz, 1H) 7.39 (s, 2H) 7.53-7.57 (m, 1H) 7.62 (dt, J = 7.84, 1.24 Hz, 1H) 7.73 (s, 1H) 7.76 (d, J = 8.26 Hz, 1H) 7.86 (t, J = 1.65 Hz, 1H) 8.09 (dd, J = 8.88, 2.68 Hz, 1H) 8.61 (s, 1H); MS (ESI pos.) m/z: 437 [M + H]+ |

Example 103

3-{[5-(2-cyclohexylethyl)-1-methyl-1H-pyrazol-4-yl]ethynyl}benzenesulfonamide

Example 104

4-{[5-(2-cyclohexylethyl)-1-methyl-1H-pyrazol-4-yl]ethynyl}benzenesulfonamide

Example 105

4-[(1-methyl-5-{2-[4-(trifluoromethyl)phenoxy]ethyl}-1H-pyrazol-4-yl)ethynyl]benzenesulfonamide

Example 106

3-[(1-methyl-5-{2-[4-(trifluoromethyl)phenoxy]ethyl}-1H-pyrazol-4-yl)ethynyl]benzenesulfonamide

Example 107

3-[(5-{[(5-fluoropyridin-2-yl)oxy]methyl}-1-methyl-1H-pyrazol-4-yl)ethynyl]benzenesulfonamide

Example 108

4-[(5-{[(5-fluoropyridin-2-yl)oxy]methyl}-1-methyl-1H-pyrazol-4-yl)ethynyl]benzenesulfonamide

Example 109

4-{[1-methyl-5-({[5-(trifluoromethyl)pyridin-2-yl]oxy}methyl)-1H-pyrazol-4-yl]ethynyl}benzenesulfonamide

Example 110

3-{[1-methyl-5-({[5-(trifluoromethyl)pyridin-2-yl]oxy}methyl)-1H-pyrazol-4-yl]ethynyl}benzenesulfonamide

Test Example 1

[$^{35}$S]GTPγS Binding Test (1)

(Preparation of Crude Membrane Fraction of CHO Cells Stably Expressing the Rat Metabotropic Glutamate Receptor (mGlu2))

CHO cells stably expressing the rat mGlu2 were cultured in a 10% dialyzed fetal bovine serum-containing Dulbecco's Modified Eagle's Medium [1% proline, 50 units/mL penicillin, 50 μg/mL streptomycin, and 2 mM L-glutamine (to be added when used)] at 37° C. in 5% $CO_2$. Confluent cells were washed with PBS(−) twice, and were then harvested with a cell scraper. Then, the cells were centrifuged at 4° C. at 1000 rpm for 5 minutes to collect. The obtained precipitate was suspended in a 20 mM HEPES buffer (pH 7.4), and then homogenized with a Teflon (registered trademark) homogenizer. The resultant was centrifuged at 4° C. at 48,000×g for 20 minutes to obtain a precipitate again. The obtained precipitate was washed twice by centrifugation, and was then homogenized with the above-mentioned buffer, so as to obtain a crude membrane fraction. The obtained crude membrane fraction was preserved at −80° C.

[$^{35}$S]GTPγS Binding Test

The frozen membrane fraction as prepared above was thawed when used, and it was then diluted with a binding test buffer (final concentration: 20 mM HEPES, 100 mM NaCl, 10 mM $MgCl_2$, 8.4 μM GDP, 10 μg/mL saponin, and 0.1% BSA). The compound of the Example was added to a membrane fraction (10 μg protein/assay), and the obtained mixture was then incubated at 30° C. for 20 minutes. Thereafter, glutamic acid (final concentration: 20 μM; but it was 30 μM only in the compounds 1 and 40 of the Examples) and [$^{35}$S]GTPγS (final concentration: 0.15 nM) were added to the reaction mixture, and then incubated at 30° C. for 1 hour. After completion of the incubation, the reaction mixture was subjected to filtration over a Whatman GF/C filter that had previously been immersed in a 20 mM HEPES buffer (pH 7.4), and the filter was then washed three times with 300 μL of ice-cold 20 mM HEPES buffer (pH 7.4). A scintillation cocktail was added to the resulting filter, and membrane-bound radioactivity was then measured with a liquid scintillation counter.

The amount of [$^{35}$S]GTPγS bound in the case of carrying out the above described reaction in the absence of glutamic acid was defined as non-specific binding. The difference between such non-specific bound and the amount of [$^{35}$S]GTPγS bound in the presence of glutamic acid was defined as specific binding. Using non-linear analysis, a concentration-inhibition curve was produced. The concentration of the compound of each Example that caused 50% inhibition ($IC_{50}$ value) of specific binding was determined from each concentration-inhibition curve.

As a result of the above described test, the $IC_{50}$ value of the compound of the present invention was found to be 10 μM or less. The $IC_{50}$ values of the compounds of the present invention are shown in Table 5 below.

TABLE 5

| Example No. | $IC_{50}$ (nM) |
| --- | --- |
| 1 | 158 |
| 40 | 24.2 |
| 50 | 76.4 |
| 58 | 13.8 |
| 64 | 9.77 |
| 73 | 2.10 |
| 81 | 14.6 |
| 83 | 22.0 |
| 84 | 2.72 |
| 87 | 3.43 |
| 89 | 55.1 |
| 94 | 18.2 |
| 98 | 42.8 |
| 100 | 61.8 |
| 106 | 7.88 |

Test Example 2

[$^{35}$S]GTPγS Binding Test (2)

(Preparation of Crude Membrane Fraction of CHO Cells Stably Expressing the Human Metabotropic Glutamate Receptor (mGlu2))

CHO cells stably expressing the human mGlu2 receptor were cultured in a 10% dialyzed fetal bovine serum-containing Dulbecco's Modified Eagle's Medium [1% proline, 50 units/mL penicillin, 50 μg/mL streptomycin, 400 μg/mL hygromycin B, and 2 mM L-glutamine (to be added when used)] at 37° C. in 5% $CO_2$. Confluent cells were washed with PBS(−) twice, and were then harvested with a cell scraper. Then, the cells were centrifuged at 4° C. at 1000 rpm for 5 minutes to collect. The obtained precipitate was suspended in a 20 mM HEPES buffer (pH 7.4), and then homogenized with a Teflon (registered trademark) homogenizer. The resultant was centrifuged at 4° C. at 48,000×g for 20 minutes to obtain a precipitate again. The obtained precipitate was washed twice by centrifugation, and was then homogenized with the above-mentioned buffer, so as to obtain a crude membrane fraction. The obtained crude membrane fraction was preserved at −80° C.

[$^{35}$S]GTPγS Binding Test

The frozen membrane fraction as prepared above was thawed when used, and it was then diluted with a binding test buffer (final concentration: 20 mM HEPES, 100 mM NaCl, 10 mM MgCl$_2$, 8.4 μM GDP, 10 μg/mL saponin, and 0.1% BSA). The compound of the Example was added to a membrane fraction (10 μg protein/assay), and the obtained mixture was then incubated at 30° C. for 20 minutes. Thereafter, glutamic acid (final concentration: 20 μM) and [$^{35}$S]GTPγS (final concentration: 0.15 nM) were added to the reaction mixture, and then incubated at 30° C. for 1 hour. After completion of the incubation, the reaction mixture was subjected to filtration over a Whatman GF/C filter that had previously been immersed in a 20 mM HEPES buffer (pH 7.4), and the filter was then washed three times with 300 μL of ice-cold 20 mM HEPES buffer (pH 7.4). A scintillation cocktail was added to the resulting filter, and membrane-bound radioactivity was then measured with a liquid scintillation counter.

The amount of [$^{35}$S]GTPγS bound in the case of carrying out the above described reaction in the absence of glutamic acid was defined as non-specific binding. The difference between such non-specific bound and the amount of [$^{35}$S]GTPγS bound in the presence of glutamic acid was defined as specific binding. Using non-linear analysis, a concentration-inhibition curve was produced. The concentration of the compound of each Example that caused 50% inhibition (IC$_{50}$ value) of specific binding was determined from each concentration-inhibition curve.

As a result of the above described test, the IC$_{50}$ value of the compound of the present invention was found to be 10 μM or less. The IC$_{50}$ values of the compounds of the present invention are shown in Table 6 below.

TABLE 6

| Example No. | IC$_{50}$ (nM) |
|---|---|
| 108 | 9.22 |
| 109 | 1.22 |

INDUSTRIAL APPLICABILITY

The compound of the present invention has an antagonistic effect on group II mGlu receptors, and it can be used as an agent for preventing and treating diseases associated with the group II mGlu receptors, and specifically as an agent for preventing or treating mood disorder (depressive disorder, bipolar disorder, etc.), anxiety disorder (generalized anxiety disorder, panic disorder, obsessive-compulsive disorder, social anxiety disorder, posttraumatic stress disorder, specific phobic disorder, acute stress disorder, etc.), schizophrenia, Alzheimer's disease, cognitive impairment, dementia, drug dependence, convulsion, tremor, pain, sleep disorder and the like.

The invention claimed is:
1. A compound represented by the formula [I], or a pharmaceutically acceptable salt thereof:

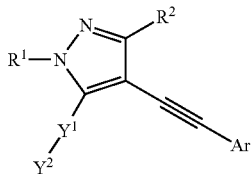

wherein
R$^1$ represents a hydrogen atom or a C$_{1-6}$ alkyl group (wherein the C$_{1-6}$ alkyl group may be substituted with 1 to 3 halogen atoms),
R$^2$ represents a hydrogen atom or a C$_{1-6}$ alkyl group (wherein the C$_{1-6}$ alkyl group may be substituted with 1 to 3 halogen atoms),
Ar represents a phenyl group or a heteroaryl group (wherein the phenyl group or the heteroaryl group is substituted with 1 to 3 substituents selected from the group consisting of —SO$_2$NR$^a$R$^b$, —SO$_2$R$^c$, —NR$^d$SO$_2$R$^e$, a C$_{1-6}$ alkyl group, an amino group, and a halogen atom),
R$^a$ and R$^b$, which may be the same or different, each represent a hydrogen atom or a C$_{1-6}$ alkyl group (wherein the C$_{1-6}$ alkyl group may be substituted with one or two substituents selected from the group consisting of an amino group, a C$_{1-6}$ alkylamino group, a di-C$_{1-6}$ alkylamino group, and a hydroxyl group) or
R$^a$ and R$^b$ may form a saturated or unsaturated 5- or 6-membered ring, which is formed together with a nitrogen atom to which they bind, and which may further contain one or more nitrogen atoms, oxygen atoms or sulfur atoms,
R$^c$ represents a hydroxyl group, a C$_{1-6}$ alkyl group, or a C$_{1-6}$ alkoxy group,
R$^d$ represents a hydrogen atom or a C$_{1-6}$ alkyl group,
R$^e$ represents a C$_{1-6}$ alkyl group or an amino group,
Y$^1$ represents —(CH$_2$)$_{n1}$—, —(CH$_2$)$_{n2}$—NR$^f$—(CH$_2$)$_{n3}$—, —(CH$_2$)$_{n4}$—O—(CH$_2$)$_{n5}$—, —(CH$_2$)$_{n6}$—NHC(=O)—(CH$_2$)$_{n7}$—, —(CH$_2$)$_{n8}$—C(=O)NH—(CH$_2$)$_{n9}$—, ethynylene, piperazin-1,4-yl, phenylene, or heteroarylene,
R$^f$ represents a hydrogen atom or a C$_{1-6}$ alkyl group,
n1 to n5 each represent an integer from 0 to 6, provided that the sum of n2 and n3 is 6 or less, and the sum of n4 and n5 is 6 or less,
n6 to n9 each represent an integer from 0 to 5, provided that the sum of n6 and n7 is 5 or less, and the sum of n8 and n9 is 5 or less, and
Y$^2$ represents an aryl group, a heteroaryl group, a partially saturated condensed polycyclic heteroaryl group {wherein the aryl group, heteroaryl group, or partially saturated condensed polycyclic heteroaryl group may be substituted with 1 to 3 substituents selected from the group consisting of a C$_{1-6}$ alkyl group, a C$_{3-6}$ cycloalkyl group, a C$_{1-6}$ alkoxy group (wherein the C$_{1-6}$ alkyl group, C$_{3-6}$ cycloalkyl group, or C$_{1-6}$ alkoxy group may be substituted with 1 to 3 halogen atoms), a cyano group, and a halogen atom} or a C$_{3-6}$ cycloalkyl group.
2. The compound or a pharmaceutically acceptable salt thereof according to claim 1, wherein in the formula [I], Ar represents a phenyl group or a 6-membered heteroaryl group, wherein the phenyl group or 6-membered heteroaryl group may be substituted with 1 to 3 substituents selected from the group consisting of —SO$_2$NR$^a$R$^b$, —SO$_2$R$^c$, —NR$^d$SO$_2$R$^e$, a C$_{1-6}$ alkyl group, an amino group, and a halogen atom, and R$^a$, R$^b$, R$^c$, R$^d$ and R$^e$ are as defined in claim 1.

3. The compound or a pharmaceutically acceptable salt thereof according to claim 1, wherein Y$^1$ represents —(CH$_2$)$_{n1}$—, —(CH$_2$)$_{n2}$—NR$^f$—(CH$_2$)$_{n3}$—, —(CH$_2$)$_{n4}$—O—(CH$_2$)$_{n5}$—, —(CH$_2$)$_{n6}$—NHC(=O)—(CH$_2$)$_{n7}$—, —(CH$_2$)$_{n8}$—C(=O)NH—(CH$_2$)$_{n9}$—, ethynylene, piperazin-1,4-yl, phenylene, pyridylene, or 5-membered heteroarylene wherein R$^f$ and n1 to n9 are as defined in claim 1, and Y$^2$ represents a phenyl group, a naphthyl group, a pyridyl group, a quinolinyl group, a partially saturated condensed polycyclic heteroaryl group {wherein the phenyl group, naphthyl group, pyridyl group, quinolinyl group, or partially saturated condensed polycyclic heteroaryl group may be substituted with 1 to 3 substituents selected from the group consisting of a C$_{1-6}$ alkyl group, a C$_{3-6}$ cycloalkyl group, a C$_{1-6}$ alkoxy group (wherein the C$_{1-6}$ alkyl group, C$_{3-6}$ cycloalkyl group, or C$_{1-6}$ alkoxy group may be substituted with 1 to 3 halogen atoms), a cyano group, and a halogen atom} or a C$_{3-6}$ cycloalkyl group.

4. A medicament comprising, as an active ingredient, a compound or a pharmaceutically acceptable salt thereof according to claim 1.

5. The medicament according to claim 4, wherein the active ingredient is a group II metabotropic glutamate receptor antagonist.

* * * * *